(12) United States Patent
Domon et al.

(10) Patent No.: US 11,548,844 B2
(45) Date of Patent: *Jan. 10, 2023

(54) MONOMER, POLYMER, NEGATIVE RESIST COMPOSITION, PHOTOMASK BLANK, AND RESIST PATTERN FORMING PROCESS

(71) Applicant: Shin-Etsu Chemical Co., Ltd., Tokyo (JP)

(72) Inventors: Daisuke Domon, Joetsu (JP); Masayoshi Sagehashi, Joetsu (JP); Masaaki Kotake, Joetsu (JP); Naoya Inoue, Joetsu (JP); Keiichi Masunaga, Joetsu (JP); Satoshi Watanabe, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 545 days.

This patent is subject to a terminal disclaimer.

(21) Appl. No.: 16/417,909

(22) Filed: May 21, 2019

(65) Prior Publication Data

US 2019/0361347 A1 Nov. 28, 2019

(30) Foreign Application Priority Data

May 25, 2018 (JP) .............................. JP2018-100615

(51) Int. Cl.
| | | |
|---|---|---|
| *G03F 7/038* | (2006.01) | |
| *G03F 7/20* | (2006.01) | |
| *G03F 7/16* | (2006.01) | |
| *G03F 7/32* | (2006.01) | |
| *G03F 7/38* | (2006.01) | |

(Continued)

(52) U.S. Cl.
CPC .............. *C07C 33/30* (2013.01); *C07C 69/54* (2013.01); *C08F 212/24* (2020.02); *G03F 1/20* (2013.01); *G03F 1/22* (2013.01); *G03F 1/60* (2013.01); *G03F 7/0382* (2013.01); *G03F 7/2004* (2013.01); *G03F 7/2037* (2013.01); *C08F 220/283* (2020.02); *C08F 220/301* (2020.02); *C08F 220/303* (2020.02);

(Continued)

(58) Field of Classification Search
None
See application file for complete search history.

(56) References Cited

U.S. PATENT DOCUMENTS

| | | |
|---|---|---|
| 5,286,600 A | 2/1994 | Ochiai et al. |
| 5,618,892 A | 4/1997 | Furihata et al. |

(Continued)

FOREIGN PATENT DOCUMENTS

| | | |
|---|---|---|
| EP | 0 208 353 A1 | 1/1987 |
| EP | 1 158 363 A1 | 11/2001 |

(Continued)

OTHER PUBLICATIONS

Machine translation of JP 2003-337414 (2003).*

(Continued)

*Primary Examiner* — Martin J Angebranndt
(74) *Attorney, Agent, or Firm* — WHDA, LLP

(57) ABSTRACT

A negative resist composition comprising a polymer comprising recurring units having at least two acid-eliminatable hydroxyl or alkoxy groups in the molecule is effective for forming a resist pattern having a high resolution and minimal LER while minimizing defects.

10 Claims, 1 Drawing Sheet

(51) Int. Cl.

| | | |
|---|---|---|
| G03F 1/20 | (2012.01) | |
| G03F 1/22 | (2012.01) | |
| C07C 33/30 | (2006.01) | |
| C07C 69/54 | (2006.01) | |
| C08F 220/30 | (2006.01) | |
| G03F 1/60 | (2012.01) | |
| C08F 212/14 | (2006.01) | |
| C08F 220/28 | (2006.01) | |

(52) U.S. Cl.
CPC .............. G03F 7/162 (2013.01); G03F 7/168 (2013.01); G03F 7/322 (2013.01); G03F 7/38 (2013.01)

(56) References Cited

U.S. PATENT DOCUMENTS

| | | | |
|---|---|---|---|
| 6,479,210 B2 | 11/2002 | Kinoshita et al. | |
| 6,485,883 B2 | 11/2002 | Kodama et al. | |
| 6,492,091 B2 | 12/2002 | Kodama et al. | |
| 6,506,534 B1 | 1/2003 | Nozaki et al. | |
| 6,605,409 B2 | 8/2003 | Kodama et al. | |
| 7,214,467 B2 | 5/2007 | Kanna et al. | |
| 7,300,739 B2 | 11/2007 | Allen et al. | |
| 7,393,624 B2 | 7/2008 | Allen et al. | |
| 7,563,558 B2 | 7/2009 | Allen et al. | |
| 8,168,367 B2 | 5/2012 | Watanabe et al. | |
| 8,361,692 B2 | 1/2013 | Tanaka et al. | |
| 8,361,693 B2 | 1/2013 | Masunaga et al. | |
| 8,637,222 B2 | 1/2014 | Tsuchihashi et al. | |
| 8,685,616 B2 | 4/2014 | Gonsalves et al. | |
| 8,900,791 B2 | 12/2014 | Tsuchimura et al. | |
| 9,023,581 B2 | 5/2015 | Kawaue et al. | |
| 9,023,587 B2 | 5/2015 | Hatakeyama et al. | |
| 9,075,306 B2 | 7/2015 | Takeda et al. | |
| 9,551,928 B2 | 1/2017 | Yamaguchi et al. | |
| 9,599,897 B2 | 3/2017 | Nishimura et al. | |
| 9,604,921 B2 | 3/2017 | Domon et al. | |
| 9,645,493 B2 | 5/2017 | Domon et al. | |
| 9,703,193 B2 | 7/2017 | Fujiwara et al. | |
| 9,904,169 B2* | 2/2018 | Adachi | G03F 7/0045 |
| 9,904,172 B2* | 2/2018 | Kumaki | C08F 220/26 |
| 9,958,775 B2 | 5/2018 | Tsuruta et al. | |
| 9,969,829 B2* | 5/2018 | Domon | G03F 7/0045 |
| 10,054,853 B2 | 8/2018 | Fujiwara | |
| 10,120,279 B2* | 11/2018 | Masunaga | C08F 228/02 |
| 10,310,375 B2 | 6/2019 | Gonsalves et al. | |
| 10,466,588 B2 | 11/2019 | Liu et al. | |
| 10,606,172 B2 | 3/2020 | Hatakeyama et al. | |
| 10,725,377 B2* | 7/2020 | Kotake | G03F 7/2059 |
| 11,231,650 B2* | 1/2022 | Kotake | C09D 125/18 |
| 2006/0166133 A1 | 7/2006 | Koitabashi et al. | |
| 2009/0226843 A1 | 9/2009 | Hatakeyama et al. | |
| 2010/0323305 A1 | 12/2010 | Tsubaki et al. | |
| 2012/0321855 A1 | 12/2012 | Iwato et al. | |
| 2012/0322007 A1 | 12/2012 | Kato et al. | |
| 2013/0017377 A1 | 1/2013 | Kataoka et al. | |
| 2013/0089819 A1 | 4/2013 | Kawaue et al. | |
| 2013/0209922 A1 | 8/2013 | Masunaga et al. | |
| 2014/0212810 A1* | 7/2014 | Hatakeyama | G03F 7/0046 430/285.1 |
| 2015/0086912 A1 | 3/2015 | Kawabata et al. | |
| 2015/0234278 A1 | 8/2015 | Hatakeyama et al. | |
| 2015/0268556 A1* | 9/2015 | Domon | G03F 7/0382 430/5 |
| 2016/0090355 A1* | 3/2016 | Domon | G03F 7/0045 430/5 |
| 2016/0229940 A1* | 8/2016 | Hatakeyama | G03F 7/0397 |
| 2016/0299428 A1* | 10/2016 | Masunaga | G03F 1/22 |
| 2016/0299430 A1* | 10/2016 | Domon | C08F 220/24 |
| 2016/0299431 A1* | 10/2016 | Adachi | G03F 7/09 |
| 2016/0320698 A1 | 11/2016 | Fujiwara et al. | |
| 2016/0342086 A1* | 11/2016 | Sagehashi | G03F 7/0046 |
| 2016/0349612 A1 | 12/2016 | Fujiwara et al. | |
| 2017/0210836 A1 | 7/2017 | Domon et al. | |
| 2017/0355795 A1 | 12/2017 | Hatakeyama et al. | |
| 2018/0039175 A1 | 2/2018 | Masunaga et al. | |
| 2018/0039185 A1* | 2/2018 | Ebihara | B82Y 10/00 |
| 2018/0180998 A1 | 6/2018 | Kotake et al. | |
| 2018/0210338 A1* | 7/2018 | Yahagi | G03F 7/0382 |
| 2019/0018319 A1* | 1/2019 | Yamazaki | G03F 7/38 |
| 2019/0361348 A1* | 11/2019 | Kotake | C09D 125/18 |
| 2020/0133121 A1* | 4/2020 | Domon | C07C 311/49 |
| 2020/0301274 A1* | 9/2020 | Taniguchi | C08L 25/06 |
| 2020/0301275 A1* | 9/2020 | Taniguchi | C09D 125/18 |

FOREIGN PATENT DOCUMENTS

| | | | |
|---|---|---|---|
| EP | 1684118 A1 | 7/2006 | |
| EP | 1975711 A1 | 10/2008 | |
| EP | 2264525 A2 | 12/2010 | |
| EP | 2328864 A1 | 6/2011 | |
| EP | 2626743 A1 | 8/2013 | |
| EP | 3 032 333 A2 | 6/2016 | |
| JP | 5-232702 A | 9/1993 | |
| JP | 8-202037 A | 8/1996 | |
| JP | 11-327143 A | 11/1999 | |
| JP | 2001-154357 A | 6/2001 | |
| JP | 2001-226430 A | 8/2001 | |
| JP | 2001-330947 A | 11/2001 | |
| JP | 2002-060361 A | 2/2002 | |
| JP | 2003-337414 A | 11/2003 | |
| JP | 2006-201532 A | 8/2006 | |
| JP | 2006-215180 A | 8/2006 | |
| JP | 3955384 B2 | 8/2007 | |
| JP | 4116340 B2 | 7/2008 | |
| JP | 2008-249762 A | 10/2008 | |
| JP | 2008-249951 A | 10/2008 | |
| JP | 1226803 B2 | 2/2009 | |
| JP | 2009-53518 A | 3/2009 | |
| JP | 4231622 B2 | 3/2009 | |
| JP | 2009-251037 A | 10/2009 | |
| JP | 2010-100604 A | 5/2010 | |
| JP | 2010-164933 A | 7/2010 | |
| JP | 2010-276910 A | 12/2010 | |
| JP | 2011-22564 A | 2/2011 | |
| JP | 2011-203644 A | 10/2011 | |
| JP | 5083528 B2 | 11/2012 | |
| JP | 2013-164588 A | 8/2013 | |
| JP | 5376847 B2 | 12/2013 | |
| JP | 2016-200651 A | 12/2016 | |
| JP | 2016-210761 A | 12/2016 | |
| JP | 2017-16068 A | 1/2017 | |
| JP | 2017-132827 A | 8/2017 | |
| JP | 6248882 B2 | 12/2017 | |
| JP | 6658204 B2 | 3/2020 | |
| KR | 10-2016-0140460 A | 12/2016 | |
| KR | 10-2018-0077073 A | 7/2018 | |
| TW | 201617313 A | 5/2016 | |
| TW | 201642042 A | 12/2016 | |
| TW | 201812450 A | 4/2018 | |
| WO | 2016/038476 A1 | 3/2016 | |

OTHER PUBLICATIONS

Ito et al., "Negative Resist Compositions," IBM Technical Disclosure Bulletin vol. 35, No. 1B, Jun. 1992, p. 397.

Ito et al., "Acid-Catalyzed Dehydration, A New Mechanism for Chemically Amplified Lithographic Imaging," ACS Symposium Series 537, Chapter 5, 1994, p. 64-87.

Yoshida et al., "Cationic chemistry and chemically amplified resist materials for microlithography; synthesis and applcations of copolymers of 4-(1-hydroxy-1-methylethyl) styrene and styrene or 4-hydroxystyrene," Polymer, vol. 35, No. 1, 1994, p. 5-13.

Office Action dated Apr. 13, 2021, issued in counterpart JP Application No. 2018-100615, with English translation. (5 pages).

European Search Report dated Oct. 28, 2019, issued in counterpart application No. 19173980.4 (10 pages).

Office Action dated May 29, 2020, issued in TW Application No. 108137972. (counterpart to U.S. Appl. No. 16/655,571.) (7 pages).

Office Action dated Jan. 25, 2021, issued in KR Application No. 10-2019-0133672 (counterpart to U.S. Appl. No. 16/655,571.) (6 pages).

(56) References Cited

OTHER PUBLICATIONS

Office Action dated Aug. 17, 2021, issued in JP application No. 2018-200797, with English translation. (counterpart to U.S. Appl. No. 16/655,571.) (6 pages).
Office Action dated Jul. 9, 2020, issued in counterpart TW Application No. 108117419 (counterpart to U.S. Appl. No. 16/419,331.) (11 pages).
Non-Final Action dated Jun. 9, 2021, issued in U.S. Appl. No. 16/419,331 (25 pages).
Non-Final Action dated Nov. 19, 2021, issued in U.S. Appl. No. 16/655,571 (34 pages).

* cited by examiner

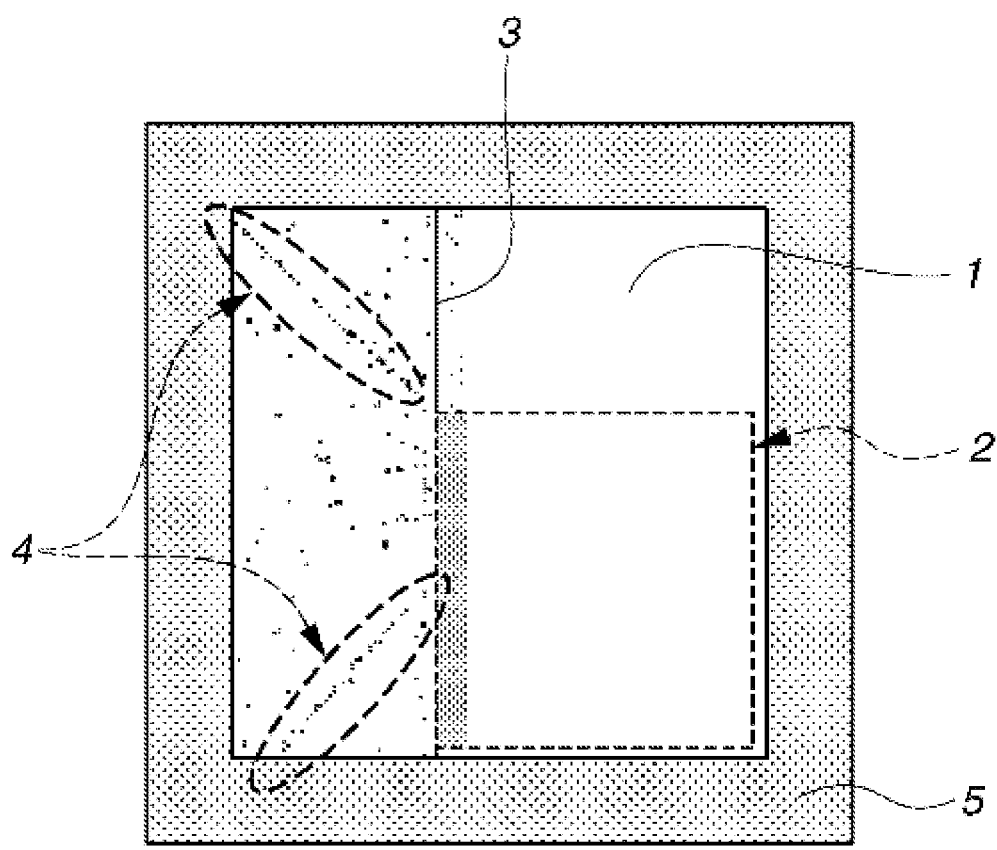

MONOMER, POLYMER, NEGATIVE RESIST COMPOSITION, PHOTOMASK BLANK, AND RESIST PATTERN FORMING PROCESS

CROSS-REFERENCE TO RELATED APPLICATION

This non-provisional application claims priority under 35 U.S.C. § 119(a) on Patent Application No. 2018-100615 filed in Japan on May 25, 2018, the entire contents of which are hereby incorporated by reference.

TECHNICAL FIELD

This invention relates to a monomer, polymer, negative resist composition, photomask blank, and pattern forming process.

BACKGROUND ART

As is well known in the art, it is required to reduce the pattern rule so as to comply with the recent demand for higher integration densities and operating speeds in LSI devices. Accordingly the exposure method and resist composition have noticeably changed. Particularly in the lithography process of forming patterns with a feature size of 0.2 µm or less, the exposure light is switched to KrF or ArF excimer laser radiation or electron beam, and the photoresist composition is changed to a chemically amplified resist composition having a good sensitivity to such high-energy radiation and a high resolution.

Resist compositions include positive tone compositions wherein the exposed region is dissolved and negative tone compositions wherein the exposed region is left as a pattern. Either one is selected in accordance with the desired resist pattern, depending on ease of processing. The chemically amplified negative resist composition generally comprises a polymer which is soluble in aqueous alkaline developer, an acid generator which is decomposed to generate an acid upon exposure to radiation, and a crosslinker which forms crosslinks between polymer molecules under the catalysis of the acid to turn the polymer insoluble in the developer (sometimes, the polymer and the crosslinker are integrated together). Further a basic compound for controlling diffusion of the acid generated upon exposure is added.

Among negative resist compositions comprising the polymer which is soluble in aqueous alkaline developer, a number of negative resist compositions based on polymers using phenol units as the alkali-soluble unit were developed as best suited for the KrF excimer laser lithography. These compositions were not used in the ArF excimer laser lithography because phenol units have little or no transmittance to exposure light having a wavelength of 150 to 220 nm. Recently a highlight is drawn to these compositions again as the negative resist for the EB or EUV lithography capable of forming finer size patterns. For example, Patent Documents 1 to 3 disclose resist compositions which exhibit a very high resolution even when used in thin film form.

Beside the above-mentioned compositions, many other chemically amplified negative resist compositions have been developed. These negative working resist compositions use a crosslinker for insolubilizing the alkali-soluble polymer under the action of an acid generated upon exposure to high-energy radiation. Many crosslinkers including those disclosed in Patent Documents 1 to 3 have been developed. On the other hand, an attempt has been made to endow the polymer with the function of crosslinker. For example, it was proposed to introduce styrene units having an alkoxymethoxy group substituted thereon (Patent Document 4), recurring units having an alkoxymethylamino group (Patent Document 5), recurring units having an epoxy group (Patent Document 6), recurring units of styrene having an acid-eliminatable group (Patent Document 7), recurring units of adamantyl having an acid-eliminatable hydroxyl group (Patent Document 8), and recurring units of aliphatic hydrocarbon and alicyclic hydrocarbon having an acid-eliminatable hydroxyl group (Patent Documents 9 to 11). Materials having an acid-eliminatable hydroxyl group are also disclosed in Non-Patent Documents 1 to 3.

CITATION LIST

Patent Document 1: JP-A 2010-276910
Patent Document 2: JP-A 2010-164933
Patent Document 3: JP-A 2008-249762
Patent Document 4: JP-A H05-232702
Patent Document 5: JP-A H08-202037
Patent Document 6: JP-A 2001-226430
Patent Document 7: JP-A 2003-337414
Patent Document 8: JP-A 2001-154357
Patent Document 9: U.S. Pat. No. 7,300,739
Patent Document 10: U.S. Pat. No. 7,393,624
Patent Document 11: U.S. Pat. No. 7,563,558
Patent Document 12: JP-A 2013-164588 (US 20130209922, EP 2626743)
Non-Patent Document 1: H. Ito and R. Sooriyakumaran, IBM Technical Disclosure Bulletin Vol. 35, No. 1B, 397 (1992)
Non-Patent Document 2: H. Ito, Y. Maekawa, R. Sooriyakumaran, and E. A. Mash, ACS Symposium Series 537, Chapter 5, pp64-87 (1994)
Non-Patent Document 3: M. Yoshida and J. M. J. Frechet, Polymer, 35 (1), 5 (1994)

DISCLOSURE OF INVENTION

While there exists the demand for a resist composition which is improved in maximum resolution, LER and temperature dependence, it is very important to minimize defect formation. Particularly, the elimination of defects is requisite for EB lithography resist compositions which are frequently used in the processing of photomask blanks. Specifically, semiconductor devices are manufactured by applying an EB lithography resist composition to a mask, processing the resist to form a pattern on the mask, and transferring the pattern on the mask onto a wafer. If defects are formed during the step of patterning the resist composition and retained on the mask, the defects are also transferred onto the wafer. This leads to a substantial drop of the manufacture yield of semiconductor devices.

An object of the invention is to provide a negative tone resist composition which forms a resist film having a high resolution corresponding to a sub-50 nm size, a low LER, and minimal defect formation; a polymer for use in the resist composition; and a resist pattern forming process using the resist composition.

Although the resist composition described in Patent Document 12 exhibits improved resolution and overcomes pattern density dependence, it still fails to meet the defect performance. For example, when the resist composition is patterned and developed, there are formed many defects distributed radially from the pattern features.

Continuing trial-and-error experiments to address the defect problem, the inventors have found that a resist composition comprising a polymer comprising recurring units having at least two acid-eliminatable hydroxyl or alkoxy groups in the molecule is effective for forming a resist pattern while minimizing defects.

In one aspect, the invention provides a monomer having the formula (1).

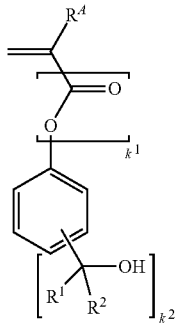

(1)

Herein $R^A$ is hydrogen or methyl, $R^1$ and $R^2$ are each independently hydrogen or a $C_1$-$C_{15}$ primary or secondary alkyl group in which some hydrogen may be substituted by a hydroxyl or $C_1$-$C_6$ alkoxy moiety, or $R^1$ and $R^2$ may bond together to form a ring with the carbon atom to which they are attached, $k^1$ is 0 or 1, and $k^2$ is an integer of 2 to 4.

In a second aspect, the invention provides a polymer comprising recurring units having the formula (a).

(a)

Herein $R^A$, $R^1$, $R^2$, $k^1$, and $k^2$ are as defined above.

The polymer may further comprise recurring units of at least one type selected from recurring units having the formulae (b1) to (b6).

(b1)

(b2)

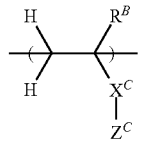

(b3)

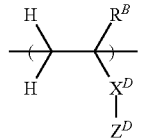

(b4)

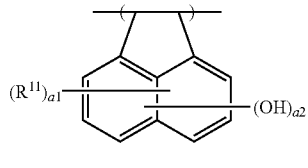

(b5)

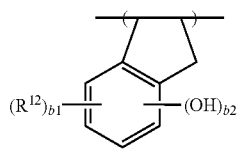

(b6)

Herein $R^B$ is hydrogen, fluorine, methyl or trifluoromethyl; $Z^A$ is a $C_1$-$C_{20}$ phenolic hydroxyl-containing group; $Z^B$ is a $C_1$-$C_{20}$ fluoroalcohol-containing group which is free of a structure capable of polarity switch under the action of acid; $Z^C$ is a $C_1$-$C_{20}$ carboxyl-containing group; $Z^D$ is a group containing a lactone, sultone, carbonate, cyclic ether or acid anhydride skeleton, alcoholic hydroxyl, alkoxycarbonyl, sulfonamide or carbamoyl moiety; $X^A$ to $X^D$ are each independently a single bond, methylene, ethylene, phenylene, fluorinated phenylene, naphthylene, —O—$X^E$—, —C(=O)—O—$X^E$— or —C(=O)—NH—$X^E$—, $X^E$ is a $C_1$-$C_6$ alkanediyl, $C_2$-$C_6$ alkenediyl, phenylene, or naphthylene group which may contain a carbonyl, ester bond, ether bond or hydroxyl moiety; $R^{11}$ and $R^{12}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group; a1 and a2 each are an integer satisfying $0 \leq a1 \leq 5$, $1 \leq a2 \leq 3$, and $1 \leq a1+a2 \leq 6$, b1 and b2 each are an integer satisfying $0 \leq b1 \leq 3$, $1 \leq b2 \leq 3$, and $1 \leq b1+b2 \leq 4$.

The polymer may further comprise recurring units of at least one type selected from recurring units having the formula (b1') and recurring units having the formula (b2').

(b1')

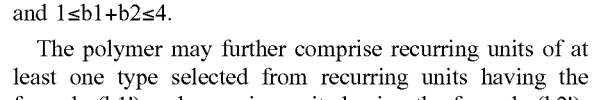

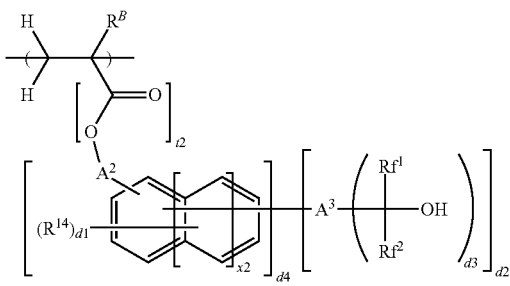

Herein $R^B$ is hydrogen, fluorine, methyl or trifluoromethyl; $A^1$ is a single bond or a $C_1$-$C_{10}$ alkanediyl group which may contain an ether bond; $A^2$ is a single bond or a $C_1$-$C_{10}$ alkanediyl group which may contain an ether bond, with the proviso that $A^2$ is a single bond in case of d4=0; $A^3$ is a single bond or a $C_1$-$C_{10}$ (d3+1)-valent aliphatic hydrocarbon group which may contain fluorine, ether bond, carbonyl moiety or carbonyloxy moiety; $Rf^1$ and $Rf^2$ are each independently a $C_1$-$C_6$ alkyl group having at least one fluorine, $Rf^1$ may bond with $A^3$ to form a ring with the atom intervening therebetween; $R^{13}$ and $R^{14}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group; t1 is 0 or 1, x1 and x2 are each independently an integer of 0 to 2, c1 is an integer satisfying $0 \leq c1 \leq 5+2(x1)-c2$, c2 is an integer of 1 to 3, d1 is an integer satisfying $0 \leq d1 \leq 5+2(x2)-d2$, d2 is 1 or 2, d3 is 1 or 2, d4 is 0 or 1, t2 is 0 or 1, t2 being 1 in case of d4=0.

The polymer may further comprise recurring units of at least one type selected from recurring units having the formula (c), recurring units having the formula (d), and recurring units having the formula (e).

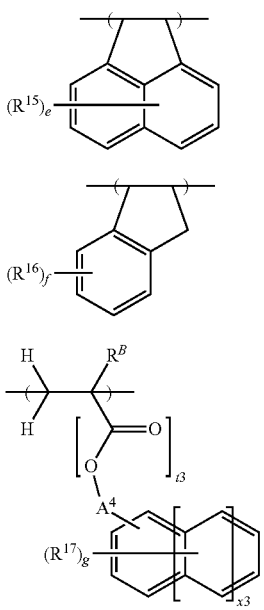

Herein $R^B$ is hydrogen, fluorine, methyl or trifluoromethyl; $R^{15}$ and $R^{16}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group; $R^{17}$ is an acetyl, acetoxy, $C_1$-$C_{20}$ alkyl, $C_1$-$C_{20}$ primary alkoxy, $C_2$-$C_{20}$ secondary alkoxy, $C_2$-$C_{20}$ acyloxy, $C_2$-$C_{20}$ alkoxyalkyl, $C_2$-$C_{20}$ alkylthioalkyl, halogen, nitro or cyano group; $A^4$ is a single bond or a $C_1$-$C_{10}$ alkanediyl group which may contain an ether bond; e is an integer of 0 to 5, f is an integer of 0 to 3, g is an integer of 0 to 5, t3 is 0 or 1, and x3 is an integer of 0 to 2.

The polymer may further comprise recurring units of at least one type selected from recurring units having the formula (f1), recurring units having the formula (f2), and recurring units having the formula (f3).

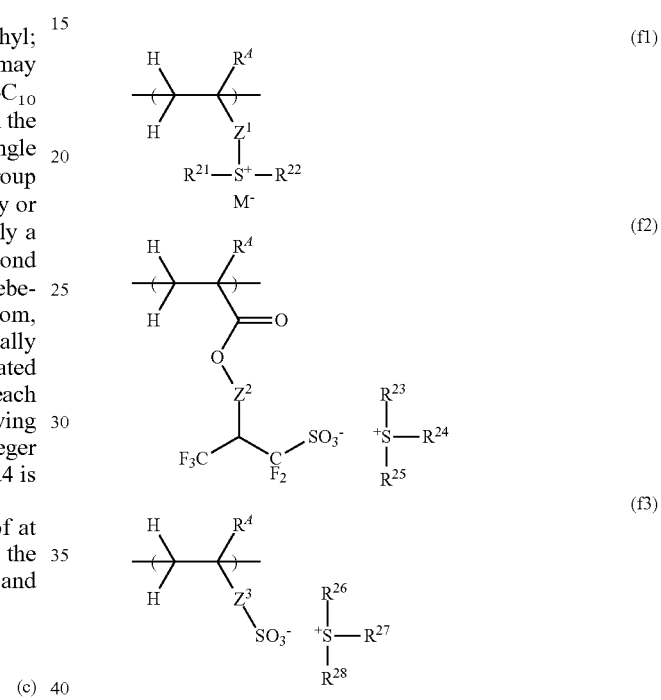

Herein $R^A$ is hydrogen or methyl; $Z^1$ is a single bond, phenylene group, —O—$Z^{11}$—, —C(=O)—O—$Z^{11}$—, or —C(=O)—NH—$Z^{11}$—, $Z^{11}$ is a $C_1$-$C_6$ alkanediyl, $C_2$-$C_6$ alkenediyl or phenylene group which may contain a carbonyl, ester bond, ether bond or hydroxyl moiety; $Z^2$ is a single bond or —$Z^{21}$—C(=O)—O—, $Z^{21}$ is a $C_1$-$C_{20}$ divalent hydrocarbon group which may contain a heteroatom; $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl, $C_2$-$C_6$ alkenediyl or phenylene group which may contain a carbonyl, ester bond, ether bond or hydroxyl moiety; $R^{21}$ to $R^{28}$ are each independently a $C_1$-$C_{20}$ monovalent hydrocarbon group which may contain a heteroatom, $R^{21}$ and $R^{22}$ may bond together to form a ring with the sulfur atom to which they are attached, any two of $R^{23}$, $R^{24}$ and $R^{25}$ may bond together to form a ring with the sulfur atom to which they are attached, any two of $R^{26}$, $R^{27}$ and $R^{28}$ may bond together to form a ring with the sulfur atom to which they are attached; and $M^-$ is a non-nucleophilic counter ion.

In a third aspect, the invention provides a negative resist composition comprising a base polymer containing the polymer defined herein.

The negative resist composition may further comprise an acid generator and/or a quencher.

In a fourth aspect, the invention provides a photomask blank comprising a resist film formed of the negative resist composition defined herein.

In a fifth aspect, the invention provides a resist pattern forming process comprising the steps of applying the negative resist composition defined herein onto a substrate to form a resist film thereon, exposing patternwise the resist film to high-energy radiation, and developing the resist film in an alkaline developer to form a resist pattern.

In a preferred embodiment, the high-energy radiation is EUV or EB.

Most often, the substrate has an outermost surface formed of a chromium-containing material. Typically, the substrate is a photomask blank.

Advantageous Effects of Invention

The negative tone resist composition comprising the inventive polymer forms a resist film having a high resolution corresponding to a sub-50 nm size, a low LER, and minimal defect formation. When the negative resist composition is processed by the micropatterning technology, especially EB lithography, a resist pattern with a very high resolution and low LER is obtained. The negative resist composition using a polymer comprising recurring units having a specific partial structure is useful in the processing of photomask blanks because the occurrence of defects is minimized. Also, the resist pattern forming process is successful in forming a resist pattern with a high resolution corresponding to a sub-50 nm size, a low LER, and minimal defect occurrence.

BRIEF DESCRIPTION OF DRAWINGS

The only figure, FIG. 1 illustrates defects which are distributed radially from a pattern feature.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group.

The acronym "PAG" stands for photoacid generator, "PEB" for post-exposure bake, "LER" for line edge roughness, "GPC" for gel permeation chromatography, "Mw" for weight average molecular weight, and "Mw/Mn" for molecular weight dispersity. In the chemical formulae, the broken line designates a valence bond, Me stands for methyl, and Ac for acetyl.

The term "high-energy radiation" is intended to encompass ultraviolet (UV) radiation, deep UV, extreme ultraviolet (EUV), electron beam (EB), x-ray, excimer laser, γ-ray and synchrotron radiation.

Monomer

One embodiment of the invention is a monomer having the formula (1).

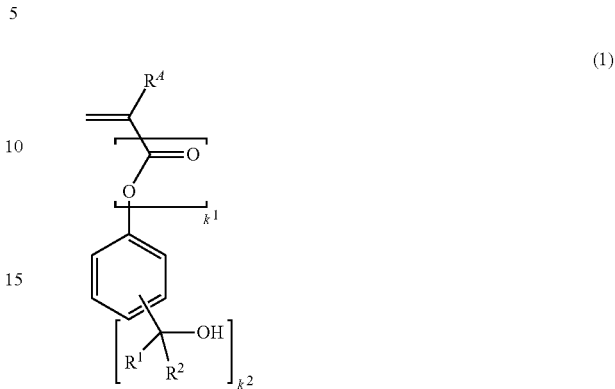

In formula (1), $R^A$ is hydrogen or methyl. $R^1$ and $R^2$ are each independently hydrogen or a $C_1$-$C_{15}$ primary or secondary alkyl group in which some hydrogen may be substituted by a hydroxyl or $C_1$-$C_6$ alkoxy moiety.

The primary or secondary alkyl group may be straight, branched or cyclic. Examples include methyl, ethyl, n-propyl, isopropyl, cyclopropyl, n-butyl, isobutyl, sec-butyl, cyclobutyl, n-pentyl, isopentyl, sec-pentyl, 1-ethylpropyl, 2,2-dimethylpropyl, cyclopentyl, n-hexyl, and cyclohexyl. The primary or secondary alkyl groups preferably have 1 to 8 carbon atoms, more preferably 1 to 6 carbon atoms, even more preferably 1 to 4 carbon atoms.

Also, $R^1$ and $R^2$ may bond together to form a ring with the carbon atom to which they are attached. The ring thus formed is preferably a 3 to 6-membered ring, more preferably 5 or 6-membered ring.

Preferably, at least one of $R^1$ and $R^2$ is a $C_1$-$C_{15}$ primary or secondary alkyl group. Also preferably, both $R^1$ and $R^2$ are $C_1$-$C_{15}$ primary or secondary alkyl groups.

In formula (1), $k^1$ is 0 or 1, and $k^2$ is an integer of 2 to 4, with $k^2$=2 being preferred for ease of synthesis of the compound.

Examples of the compound having formula (1) are shown below, but not limited thereto.

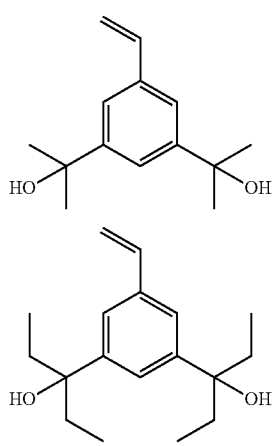

-continued
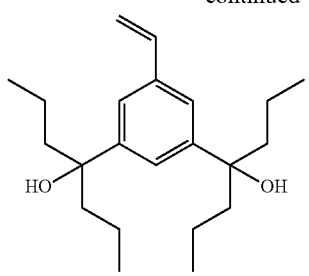
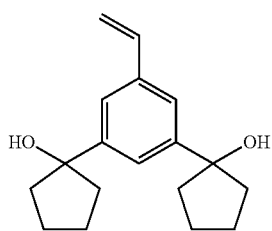
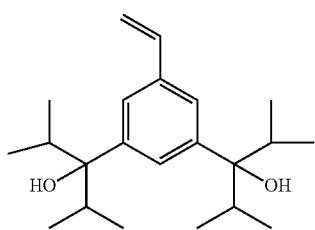
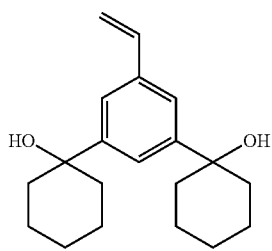
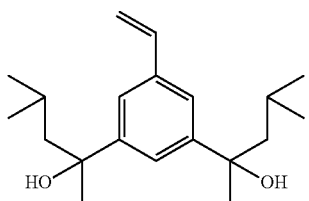
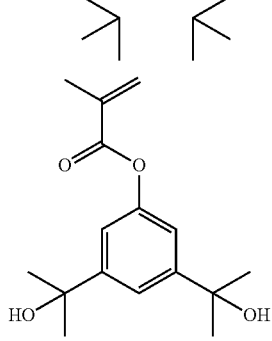
-continued
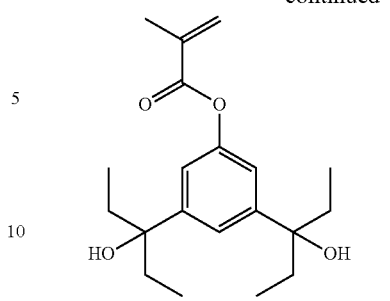
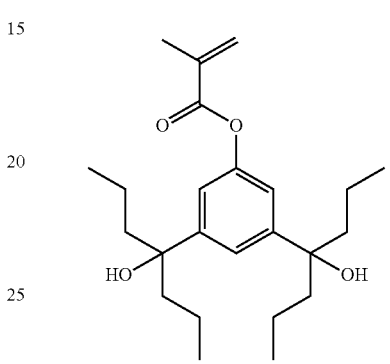
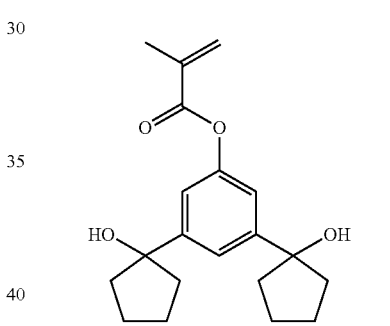
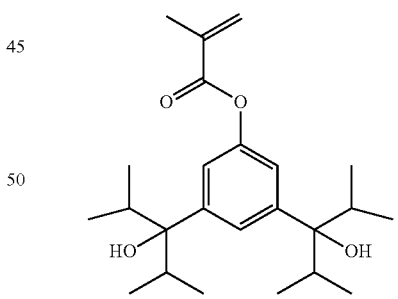
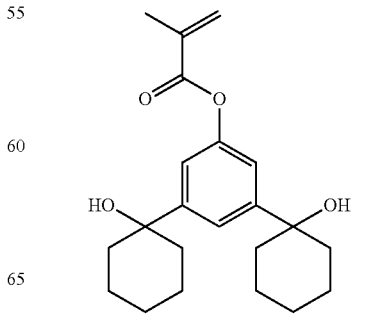

-continued

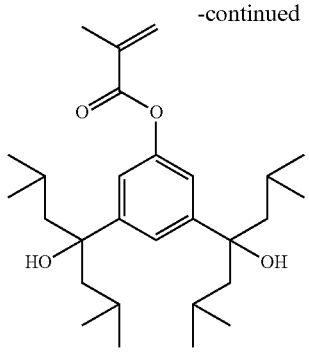

A method for synthesizing the compound having formula (1), for example, formula (1) wherein $R^A$ is hydrogen, $k^1=0$, $k^2=2$, $R^1$ and $R^2$ are methyl is exemplified by the following Scheme A, but not limited thereto.

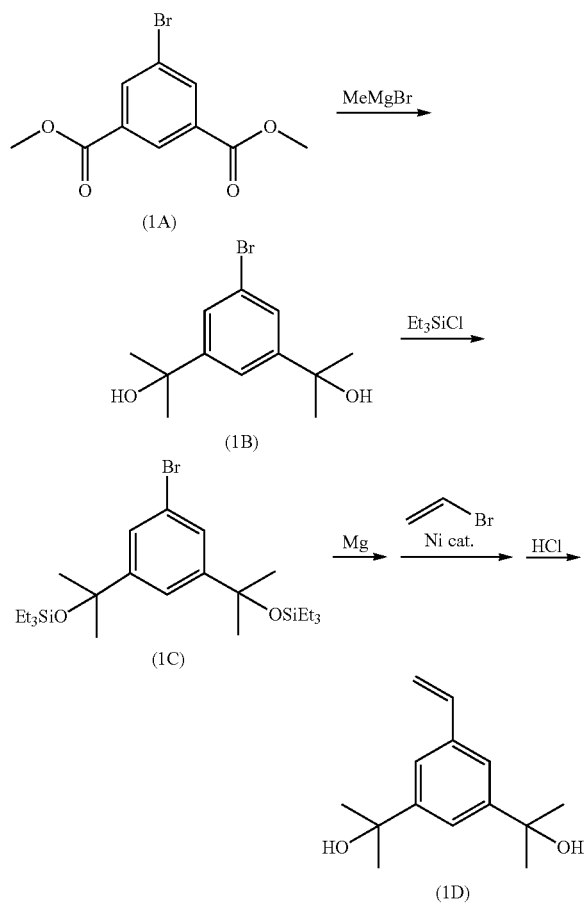

In the reaction according to Scheme A, first dimethyl 3-bromoisophthalate (1A) at its ester site is reduced with Grignard reagent, and purification is carried out, if necessary, by a standard technique such as distillation, re-crystallization or chromatography, obtaining alcohol (1B). Subsequently, the hydroxyl group on alcohol (1B) is protected with a silyl group, and purification is carried out, if necessary, by a standard technique such as distillation, re-crystallization or chromatography, obtaining compound (1C).

Once the compound (1C) is converted to a Grignard reagent with the assistance of magnesium, it is reacted with vinyl bromide in the presence of a nickel catalyst. Finally, deprotection of silyl group is carried out in hydrochloric acid, yielding monomer (1D).

Another method for synthesizing the compound having formula (1), for example, formula (1) wherein $R^A$ is methyl, $k^1 0=1$, $k^2=2$, $R^1$ and $R^2$ are methyl is exemplified by the following Scheme B, but not limited thereto.

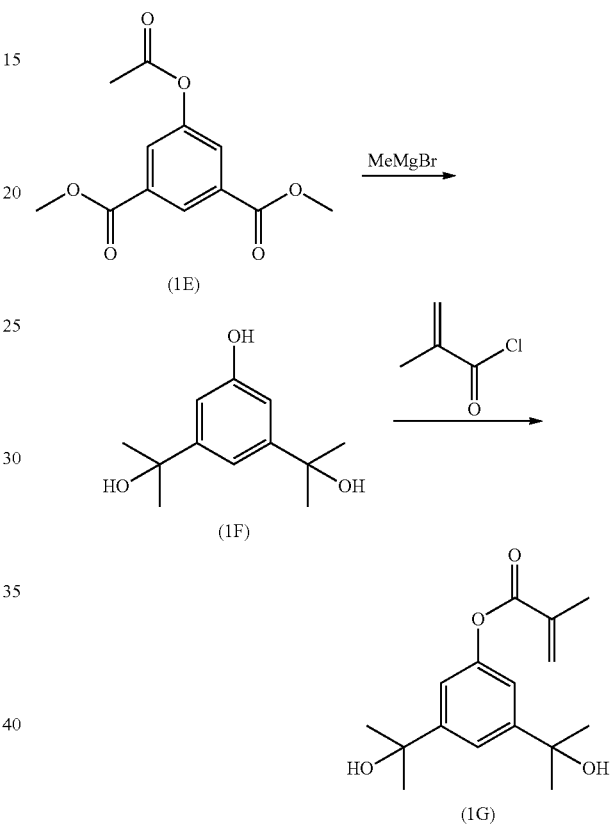

In the reaction according to Scheme B, first dimethyl 3-acetoxyisophthalate (1E) at its ester site is reduced with Grignard reagent, and purification is carried out, if necessary, by a standard technique such as distillation, re-crystallization or chromatography, obtaining phenol compound (1F). Subsequently phenol compound (1F) is reacted with an acylating agent, obtaining monomer (1G). The reaction readily takes place in a well-known way. Preferably, the reaction is conducted in a solventless system or in a solvent (e.g., methylene chloride, toluene, hexane, diethyl ether, THF or acetonitrile) by sequentially or simultaneously adding phenol compound (1F), the acylating agent, and a base (e.g., triethylamine, pyridine or 4-dimethylaminopyridine) and allowing the reaction to take place while cooling or heating if necessary. The product may be purified by a standard technique such as distillation, re-crystallization or chromatography, if necessary.

Polymer

A second embodiment of the invention is a polymer comprising recurring units having the formula (a), which are also referred to as recurring units (a). The recurring units (a) are derived from the monomer having formula (1).

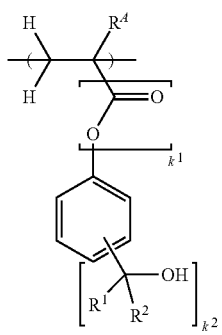

(a)

Herein $R^A$, $R^1$, $R^2$, $k^1$, and $k^2$ are as defined above.

The mechanism that a polymer comprising recurring units (a) turns negative working is described below with reference to the recurring unit having formula (a) wherein $R^A$ is hydrogen, $k^1=0$, $k^2=2$, $R^1$ and $R^2$ are methyl, that is, recurring unit A in Scheme C, shown below. Upon exposure to high-energy radiation, the recurring unit A functions such that the hydroxyl group undergoes elimination reaction under the action of an acid which is generated by the acid generator, forming a cation. Since two eliminatable hydroxyl groups are included as shown in Scheme C, there are formed two cations: cation A and cation AA. These cations undergo nucleophilic attack from another polymer (designated Nu) and crosslink therewith, forming crosslinked polymer A or crosslinked polymer AA. Since the crosslinked polymer has an increased molecular weight, it is insoluble in the developer, with the result of negative working. It is believed that dehydrated polymer A and dehydrated polymer AA are also formed as a result of proton being eliminated from cation A and cation AA. The dehydrated polymer has a reduced solubility in the developer due to the loss of hydroxyl groups, with the result of negative working.

Scheme C

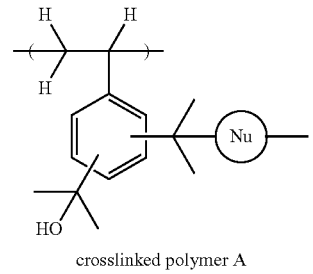

crosslinked polymer A

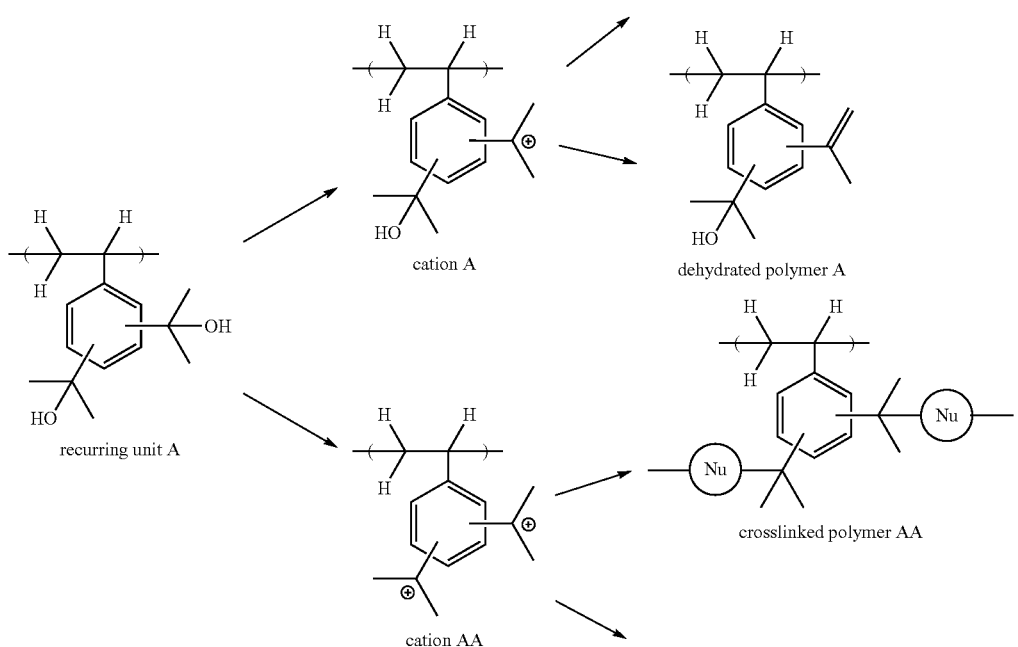

-continued

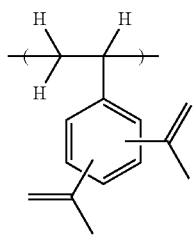

dehydrated polymer AA

With reference to Scheme D shown below, it is believed that the polymer comprising 4-(2-hydroxy-2-propyl)styrene unit (recurring unit B in Scheme D) described in Patent Document 12 also turns negative working through the same mechanism as recurring unit A.

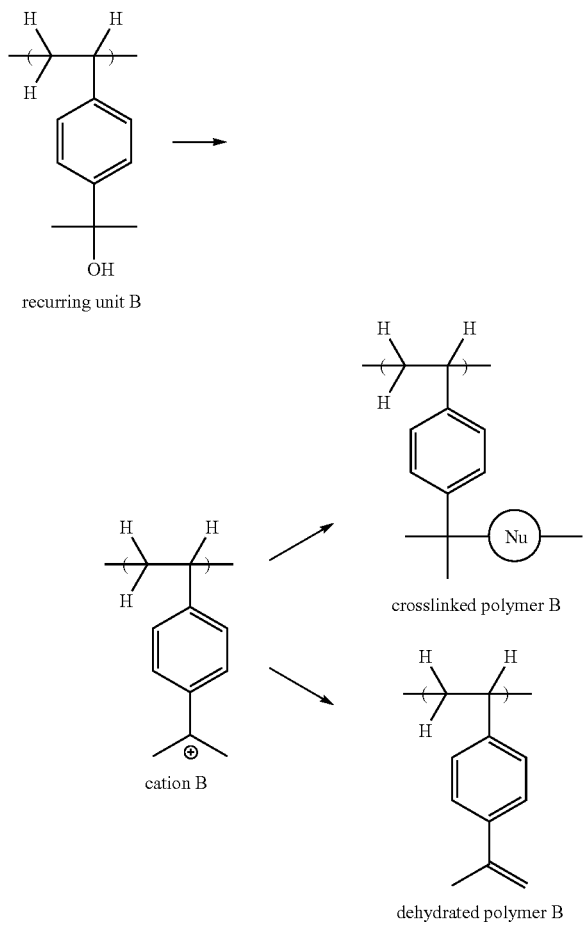

In an experiment where a negative resist composition comprising the polymer comprising 4-(2-hydroxy-2-propyl) styrene unit (recurring unit B in Scheme D) described in Patent Document 12 is exposed imagewise and developed by lithography, radially distributed defects are observed as shown in FIG. 1. In FIG. 1, there are illustrated a photomask blank substrate 1, a region 2 on the substrate where a line-and-space pattern is written, the position 3 within which the number of defects is detectable, radial defects 4, and a background 5. The reason why radial defects are formed is presumed as follows.

The dehydrated polymer B has a reduced solubility in alkaline developer due to the loss of hydroxyl groups as compared with the polymer prior to dehydration reaction, but still retains a slight solubility. Then during development, the dehydrated polymer is slightly dissolved out from the exposed region, but at a very slow rate. In general, development is carried out by feeding the developer to the substrate while spinning the substrate. Since the dehydrated polymer has a very low dissolution rate, it is not completely removed by the developer, but is rather faintly left on the substrate at the end of development. Such residual polymer manifests itself as defects distributed radially from the center of the substrate.

Although it is forecast that a resist composition comprising a polymer comprising recurring units according to the invention manifests similar defects, quite unexpectedly no defects are found. It is believed that since the dehydrated polymer A which is regarded the cause of defects has hydroxyl groups, it has a relatively high water solubility so that it is clearly removed away by the developer. Although the dehydrated polymer AA is presumed to become the cause of defects, the amount of dehydrated polymer created is so small that the dehydrated polymer may not manifest itself as defects.

Preferred examples of the recurring units (a) are shown below, but not limited thereto.

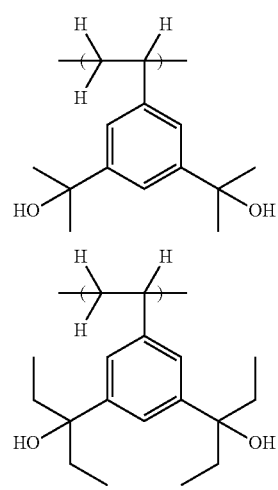

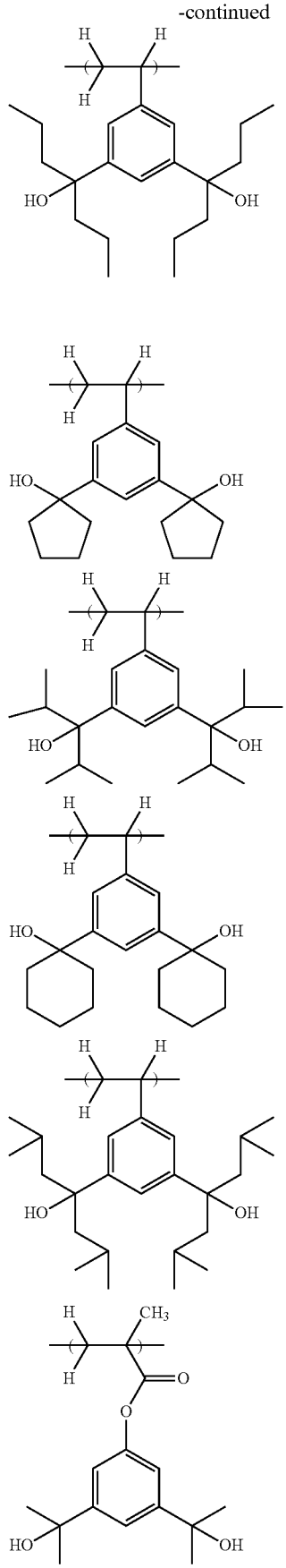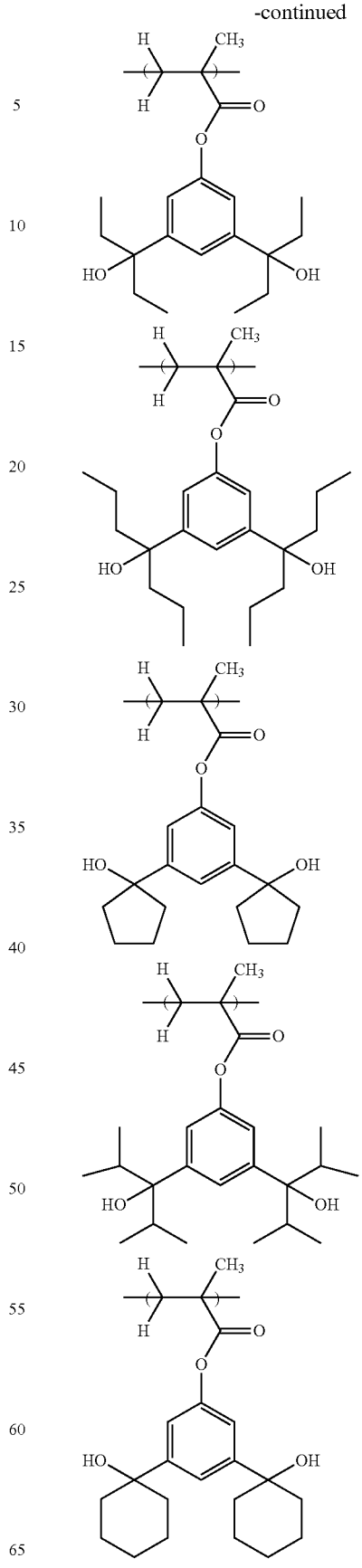

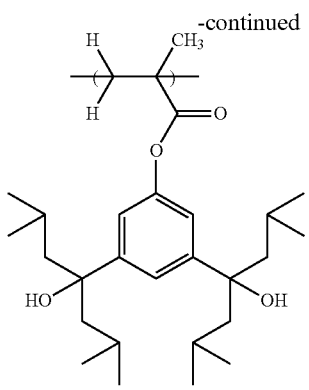

The negative resist composition comprising the inventive polymer turns to be negative working through the mechanism that a benzyl cation formed as a result of elimination reaction taking place under the action of acid is utilized to induce crosslinking between polymer molecules and also through the polarity switch of the polymer triggered by dehydration reaction. For obtaining these effects, the amount of recurring units (a) incorporated is preferably 1 to 90 mol %, more preferably 10 to 80 mol %, even more preferably 15 to 70 mol %, based on the overall recurring units of the polymer. As long as the amount of recurring units (a) incorporated is in the range, the benefits of the invention are obtained because a sufficient change of alkali solubility occurs due to acid-catalyzed reaction. The recurring units (a) may be of one type or a combination of two or more types.

For the purposes of controlling the solubility in alkaline developer and improving the adhesion to substrates, the polymer may further comprise recurring units of at least one type selected from recurring units having the formulae (b1) to (b6). The recurring units having the formulae (b1) to (b6) are also referred to as recurring units (b1) to (b6), respectively.

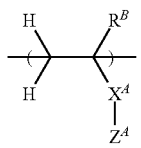 (b1)

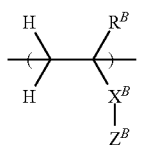 (b2)

(b3)

(b4)

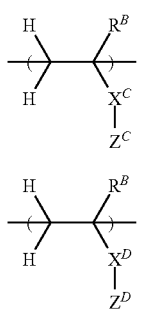

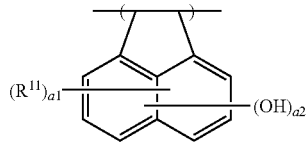 (b5)

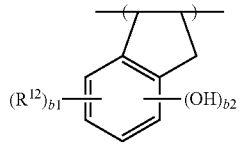 (b6)

In formulae (b1) to (b4), $R^B$ is hydrogen, fluorine, methyl or trifluoromethyl, with hydrogen or methyl being preferred.

In formulae (b1) to (b4), $Z^A$ is a $C_1$-$C_{20}$ phenolic hydroxyl-containing group. $Z^B$ is a $C_1$-$C_{20}$ fluoroalcohol-containing group which is free of a structure capable of polarity switch under the action of acid. $Z^C$ is a $C_1$-$C_{20}$ carboxyl-containing group. $Z^D$ is a group containing a lactone skeleton, sultone skeleton, carbonate skeleton, cyclic ether skeleton or acid anhydride skeleton, alcoholic hydroxyl moiety, alkoxycarbonyl moiety, sulfonamide moiety or carbamoyl moiety.

In formulae (b1) to (b4), $X^A$ to $X^D$ are each independently a single bond, methylene, ethylene, phenylene, fluorinated phenylene, naphthylene, —O—$X^E$—, —C(=O)—O—$X^E$— or —C(=O)—NH—$X^E$—, wherein $X^E$ is a $C_1$-$C_6$ alkanediyl, $C_2$-$C_6$ alkenediyl, phenylene, or naphthylene group which may contain a carbonyl moiety, ester bond, ether bond or hydroxyl moiety.

In formulae (b5) and (b6), $R^{11}$ and $R^{12}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group. Examples of the hydrocarbon moiety in the acyloxy, alkyl and alkoxy groups represented by $R^{11}$ and $R^{12}$ include methyl, ethyl, propyl, isopropyl, butyl, pentyl, hexyl, and structural isomers of the carbon skeleton having a branched or cyclic structure. A carbon count in the range ensures good solubility in alkaline developer.

In formulae (b5) and (b6), a1 and a2 each are an integer satisfying 0≤a1≤5, 1≤a2≤3, and 1≤a1+a2≤6, b1 and b2 each are an integer satisfying 0≤b1≤3, 1≤b2≤3, and 1≤b1+b2≤4.

Examples of the recurring units (b1) are shown below, but not limited thereto. Herein $R^B$ is as defined above.

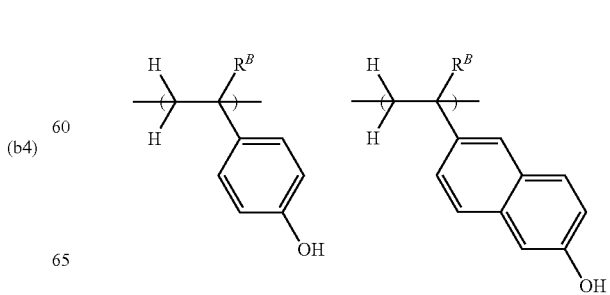

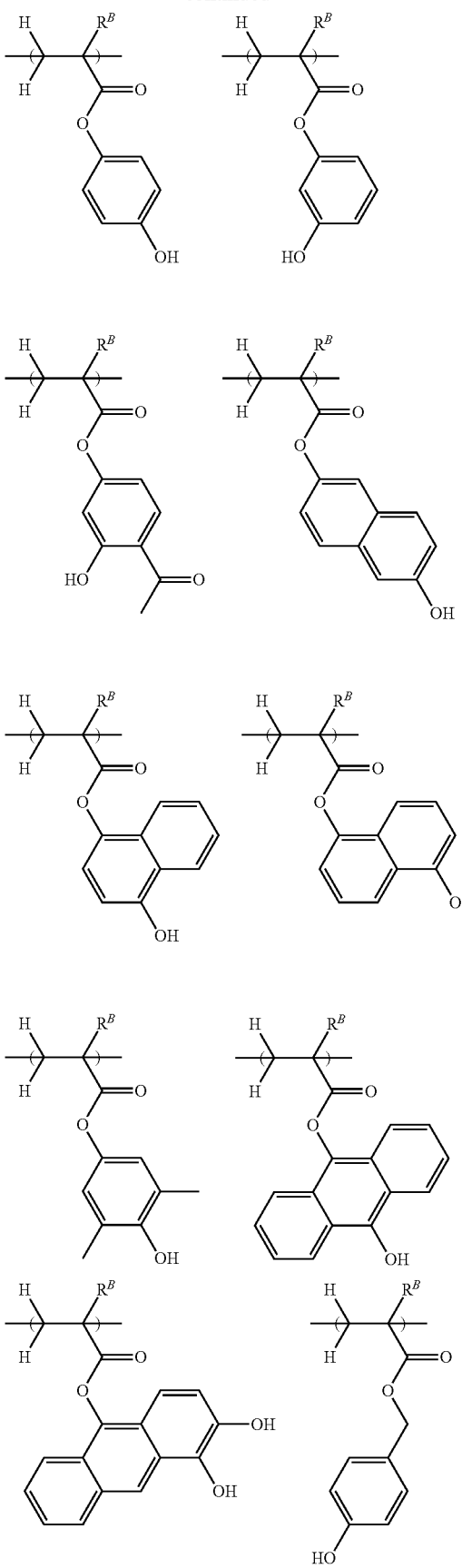
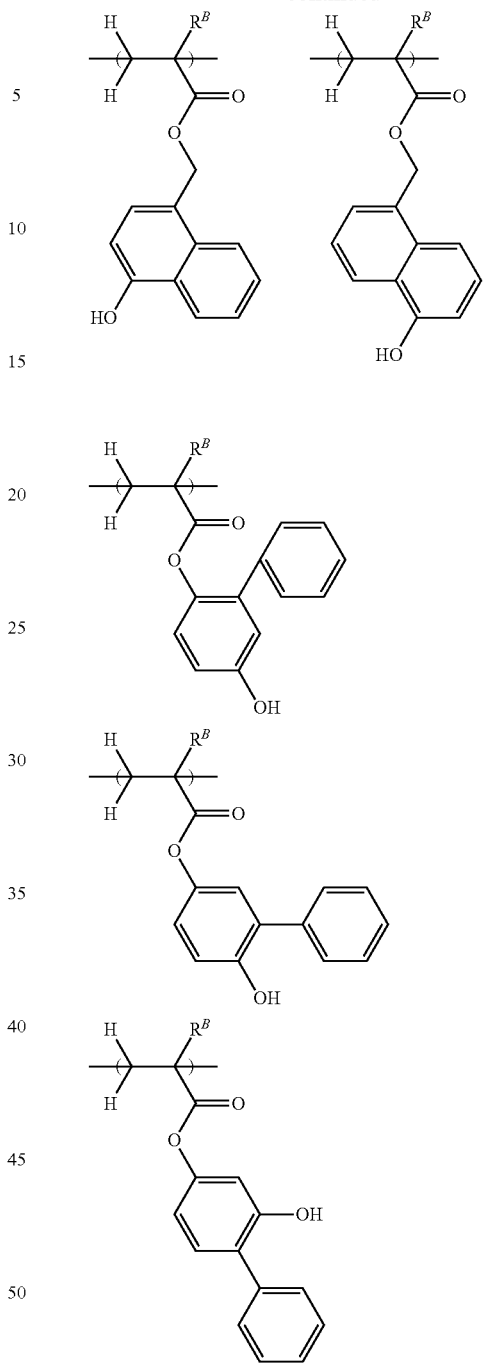

The recurring unit (b2) has a fluoroalcohol-containing group having a high affinity to alkaline aqueous solution. Suitable fluoroalcohol-containing units include recurring units containing a 1,1,1,3,3,3-hexafluoro-2-propanol residue or 2-hydroxy-2-trifluoromethyloxolane structure, as described in JP-A 2007-297590, JP-A 2008-111103, JP-A 2008-122932, and JP-A 2012-128067. Although these units have a tertiary alcoholic hydroxyl group or hemiacetal structure, they have no reactivity to acid because of fluorine substitution.

Examples of the recurring units (b2) are shown below, but not limited thereto. Herein $R^B$ is as defined above.

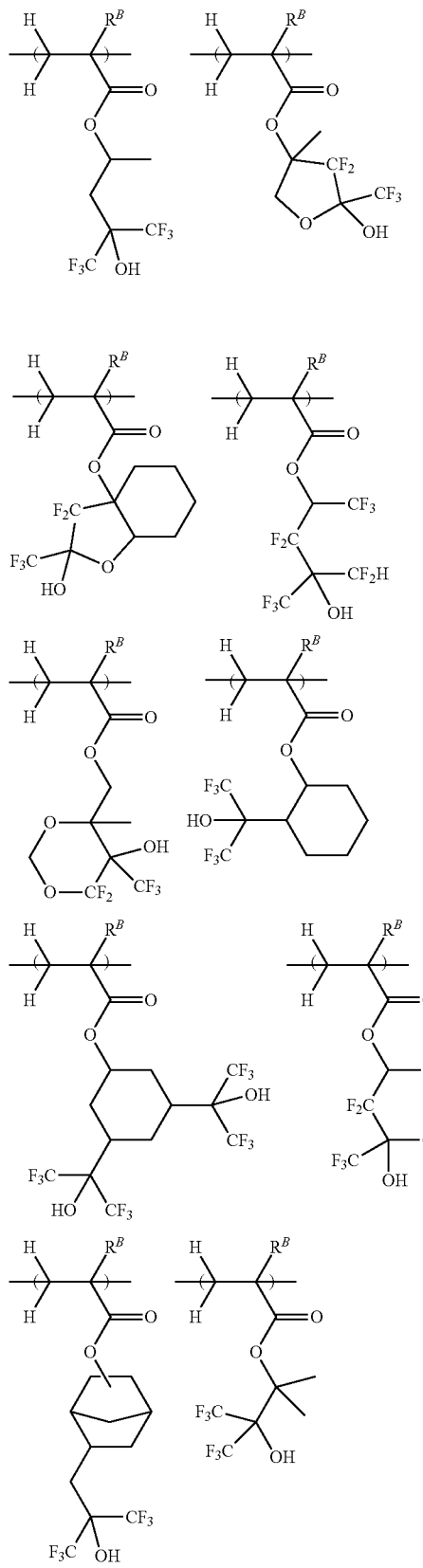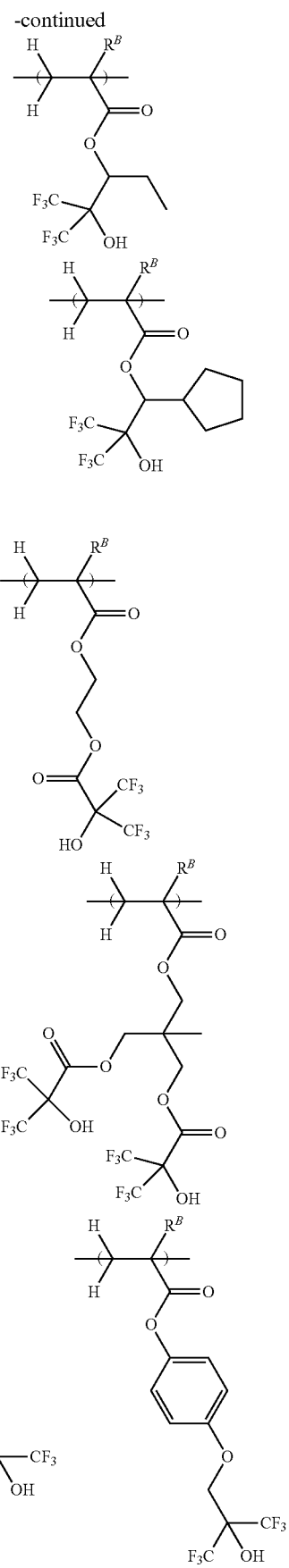

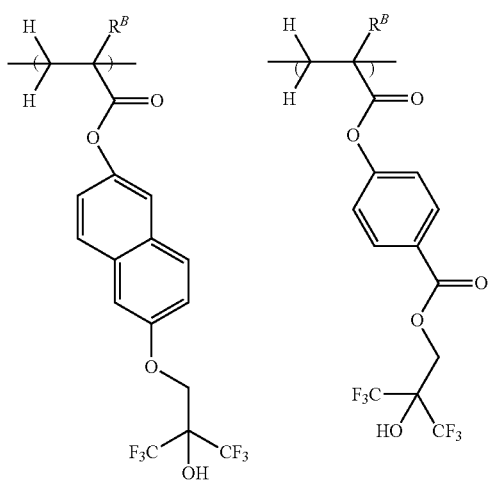
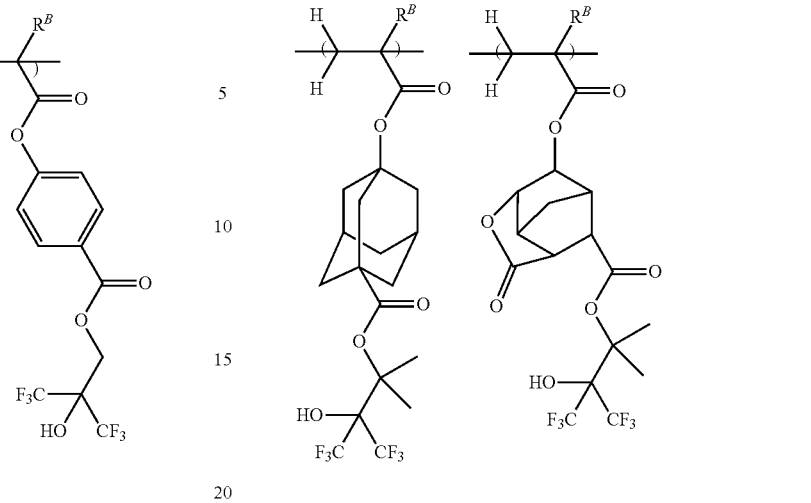
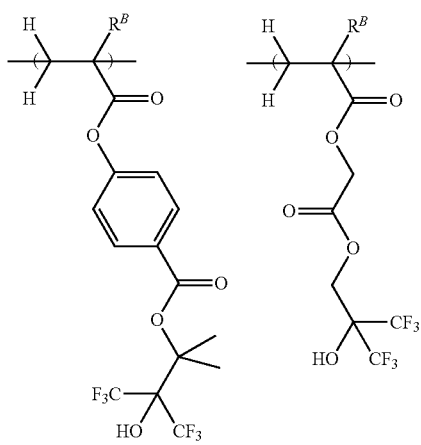
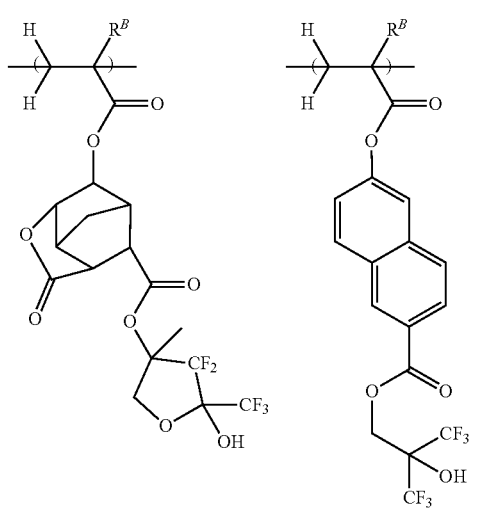
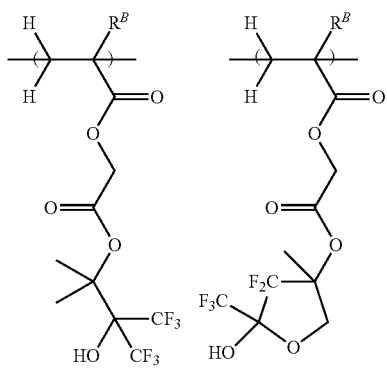
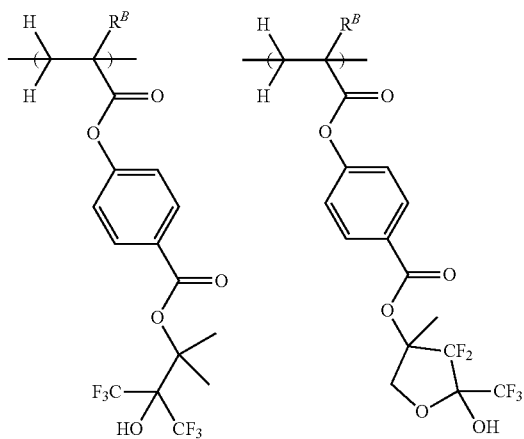

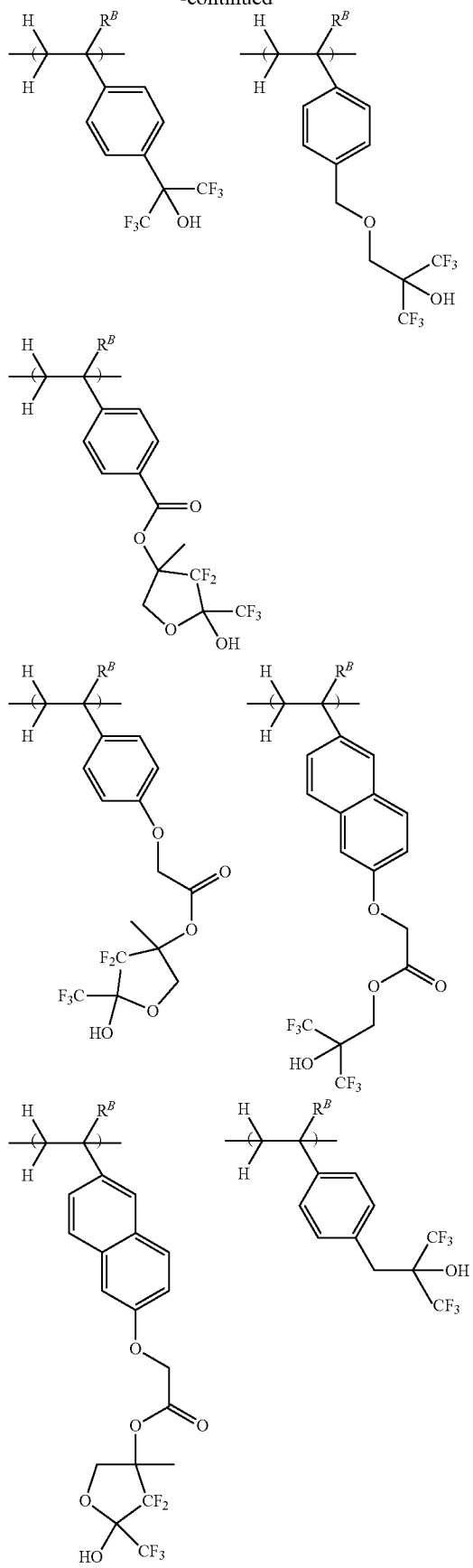
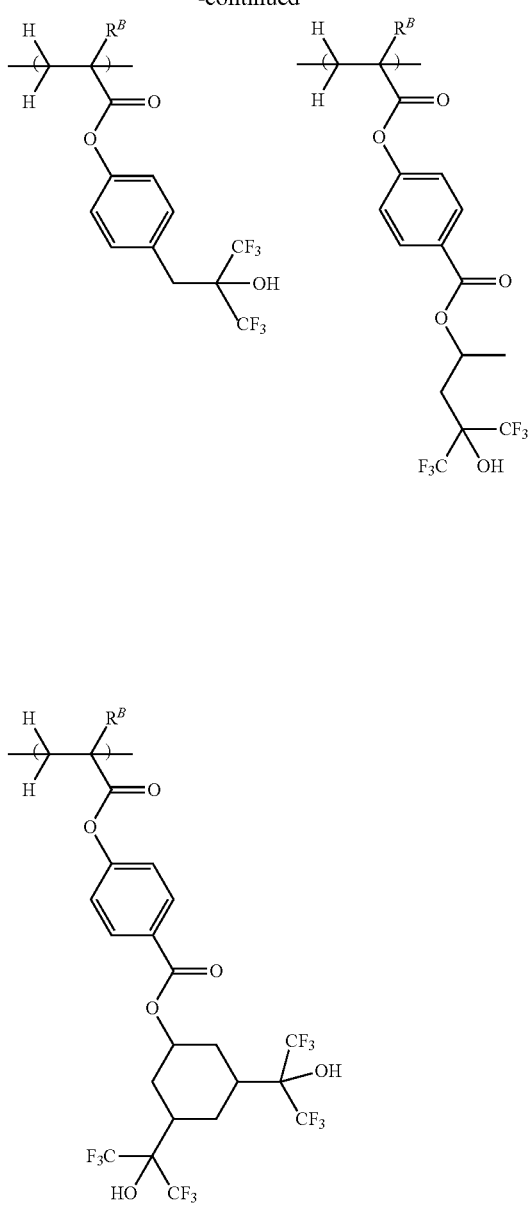

It is also possible that once the fluoroalcohol group is protected with an acyl group or acid labile group, fluoroalcohol-containing units corresponding to formula (b2) are generated through hydrolysis in alkaline developer or deprotection with the aid of acid after exposure. Such preferred recurring units include those described in paragraphs [0036]-[0040] and those having formula (2a), (2b) or (20 in paragraph [0041] of JP-A 2012-128067 (U.S. Pat. No. 8,916,331, EP 2466379).

Examples of the recurring units (b3) are shown below, but not limited thereto. Herein $R^B$ is as defined above.

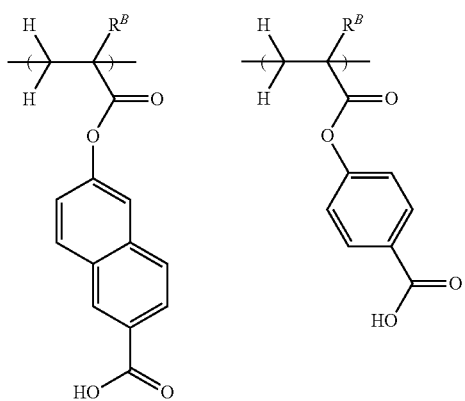
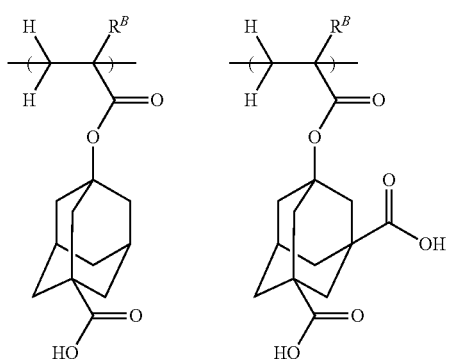
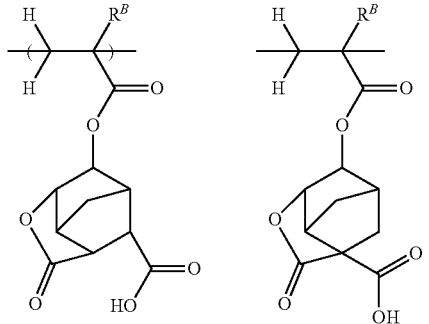
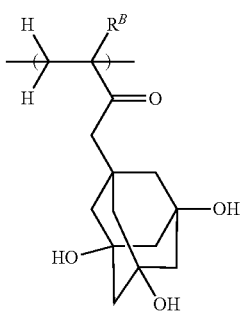
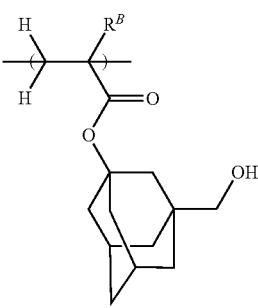
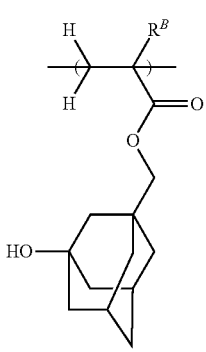
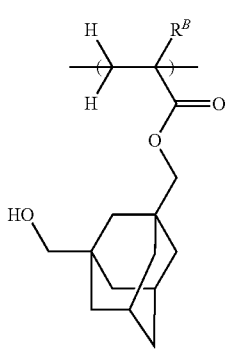
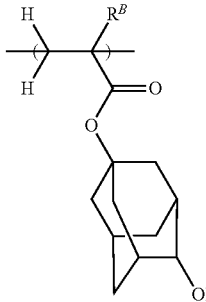
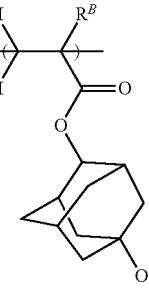
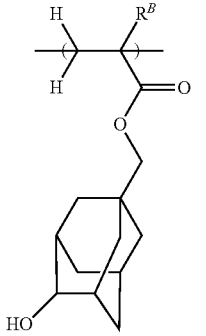
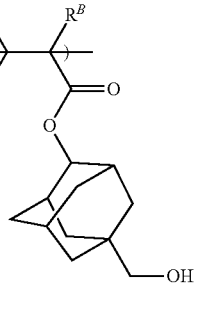
Examples of the recurring units (b4) are shown below, but not limited thereto. Herein $R^B$ is as defined above.
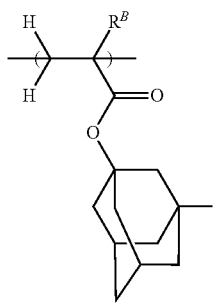
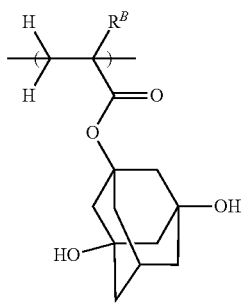
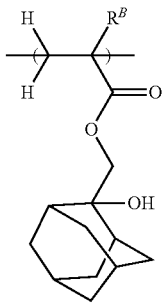
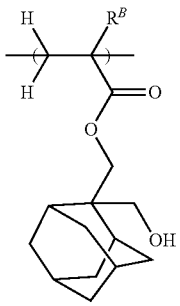

-continued

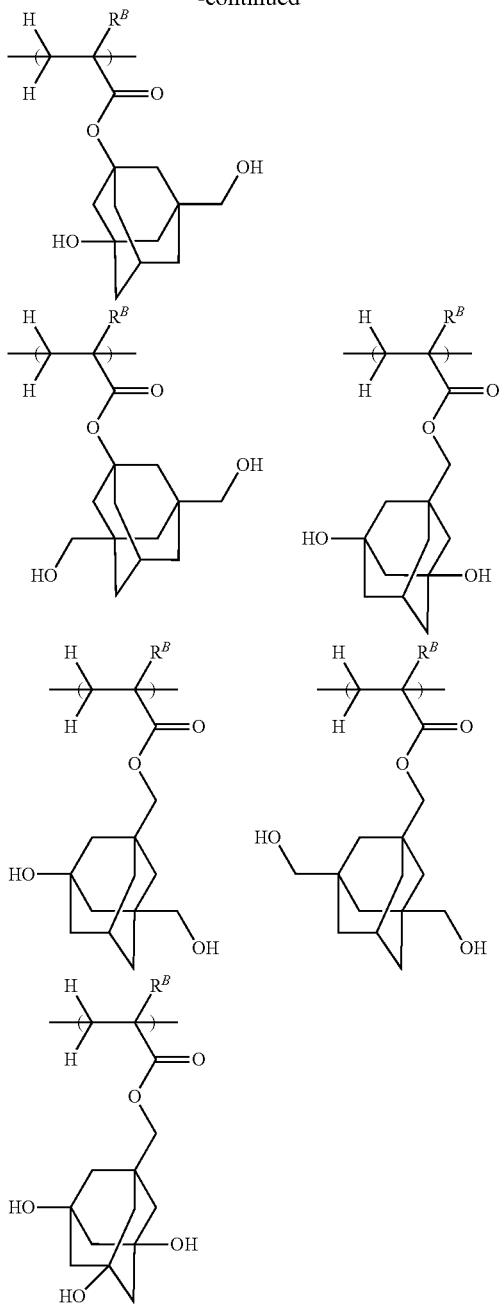

Examples of the recurring units (b5) and (b6) are shown below, but not limited thereto.

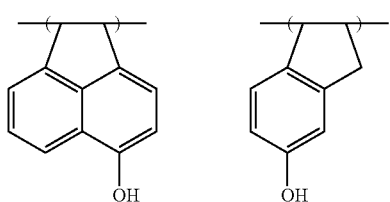

Among the recurring units (b1) to (b6), the inventive polymer preferably comprises recurring units of at least one type selected from recurring units (b1) and (b2). Of the recurring units (b1) and (b2), preference is given to recurring units having the formula (b1') and recurring units having the formula (b2'), which are also referred to as recurring units (b1') and (b2'), respectively. These recurring units function to effectively promote the insolubilizing reaction associated with elimination of the acid-eliminatable group in the recurring unit (a) and to allow for appropriate thermal motion of the polymer. Using such a polymer, a negative resist composition having high resolution is obtainable.

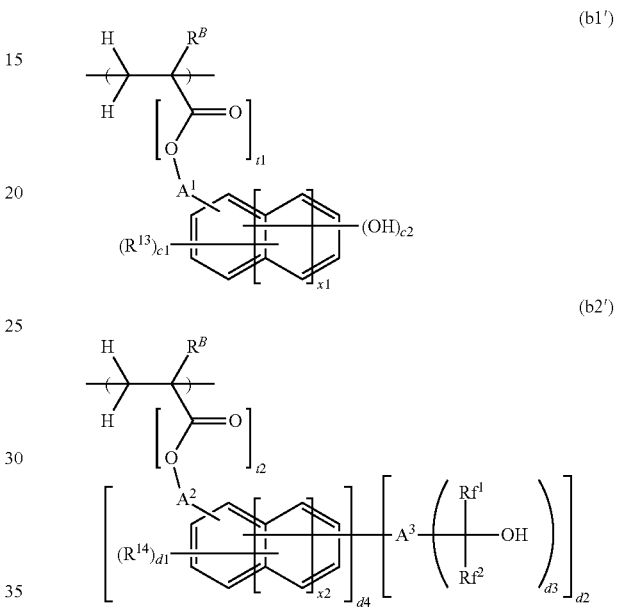

In formulae (b1') and (b2'), $R^B$ is hydrogen, fluorine, methyl or trifluoromethyl, with hydrogen or methyl being preferred.

In formulae (b1') and (b2'), $A^1$ and $A^2$ are each independently a single bond or a $C_1$-$C_{10}$ alkanediyl group which may contain an ether bond. Examples of the alkanediyl group represented by $A^1$ and $A^2$ include methylene, ethylene, propylene, butylene, pentylene, hexylene, and structural isomers of the carbon skeleton having a branched or cyclic structure. When an ether bond is contained in $A^1$, in case t1=1 in formula (b1'), it may be at any position excluding between the α- and β-position carbons relative to the ester oxygen. In case t1=0 in formula (b1'), the atom bonding to the main chain is an ethereal oxygen atom, and a second ether bond may be contained at any position excluding between the α- and β-position carbons relative to that ethereal oxygen. As long as the carbon count of the alkanediyl group is up to 10, good solubility in alkaline developer is ensured.

In formula (b2'), $A^3$ is a single bond or a $C_1$-$C_{10}$ (d3+1)-valent aliphatic hydrocarbon group which may contain fluorine, ether bond, carbonyl moiety or carbonyloxy moiety. Suitable groups include aliphatic hydrocarbons such as methane, ethane, propane, butane, pentane, hexane and structural isomers, with the number (d3+1) of hydrogen atoms being eliminated.

In formula (b2'), $Rf^1$ and $Rf^2$ are each independently a $C_1$-$C_6$ alkyl having at least one fluorine, $Rf^1$ may bond with $A^3$ to form a ring with the atom intervening therebetween. Suitable groups include fluoromethyl, difluoromethyl, trifluoromethyl, 2,2,2-trifluoroethyl, pentafluoroethyl, and 1,1,1,3,3,3-hexafluoro-2-propyl.

In formulae (b1') and (b2'), $R^{13}$ and $R^{14}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group. Examples of the hydrocarbon moiety in the acyloxy, alkyl and alkoxy groups represented by $R^{13}$ and $R^{14}$ include methyl, ethyl, propyl, isopropyl, butyl, pentyl, hexyl, and structural isomers of the carbon skeleton having a branched or cyclic structure. A carbon count in the range ensures good solubility in alkaline developer.

In formulae (b1') and (b2'), t1 is 0 or 1. The subscripts x1 and x2 are each independently an integer of 0 to 2. The relevant structure represents a benzene skeleton when x1=x2=0, a naphthalene skeleton when x1=x2=1, or an anthracene skeleton when x1=x2=2. The subscript c1 is an integer satisfying 0≤c1≤5+2(x1)−c2, c2 is an integer of 1 to 3, d1 is an integer satisfying 0≤d1≤5+2(x2)-d2, and d2 is 1 or 2, with d2 being 1 in case of d4=0. The subscript d3 is 1 or 2, d4 is 0 or 1, and t2 is 0 or 1, t2 being 1 in case of d4=0.

Where the recurring units (b1') are free of a linker (—CO—$A^1$-), that is, have formula (b1') wherein t1=0 and $A^1$ is a single bond, indicating that aromatic ring is directly bonded to the polymer backbone, suitable recurring units (b1') include those derived from 3-hydroxystyrene, 4-hydroxystyrene, 5-hydroxy-2-vinylnaphthalene, and 6-hydroxy-2-vinylnaphthalene. Of these, recurring units having the formula (b1'-1) are more preferred.

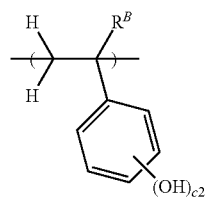

(b1'-1)

Herein $R^B$ and c2 are as defined above.

Where the recurring units (b1') have a linker (—CO—O—$A^1$-), that is, have formula (b 1') wherein t1=1, preferred examples of the recurring units (b1') are given below, but not limited thereto. Herein $R^B$ is as defined above.

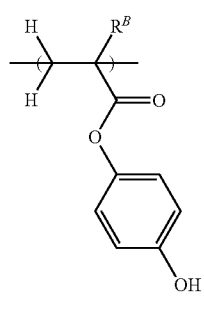 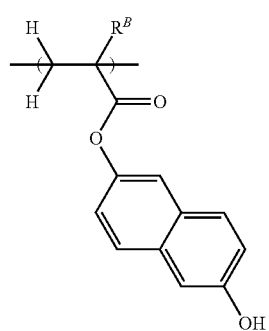

-continued

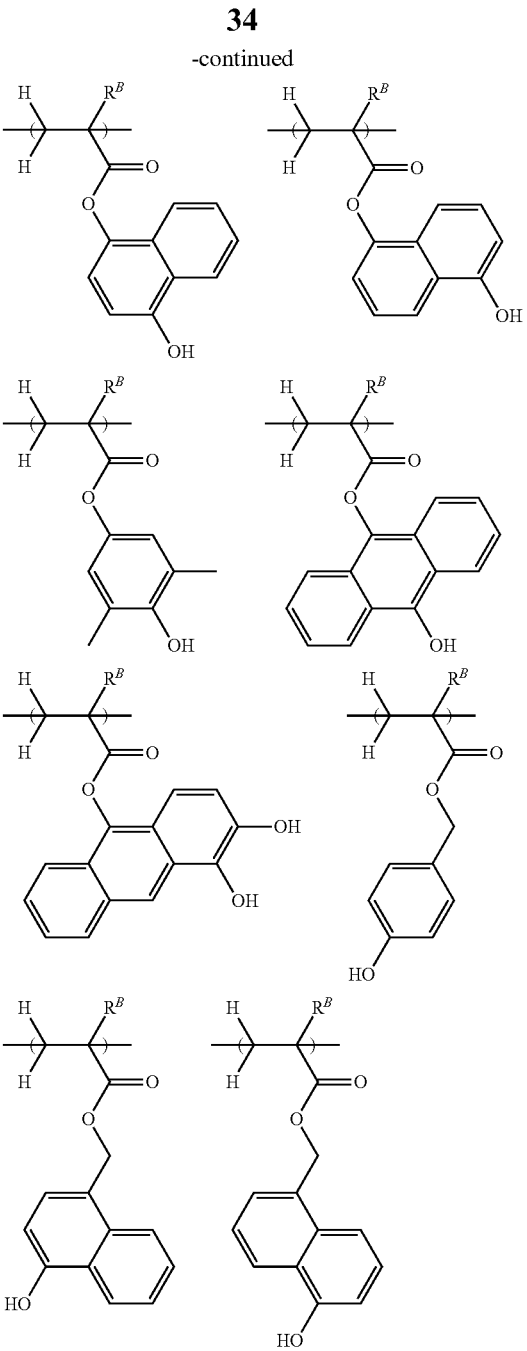

Preferred examples of the recurring unit (b2') are shown below, but not limited thereto. Herein $R^B$ is as defined above.

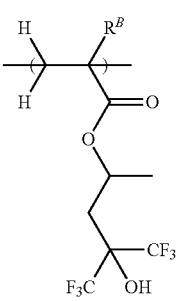 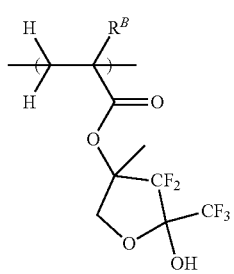

-continued
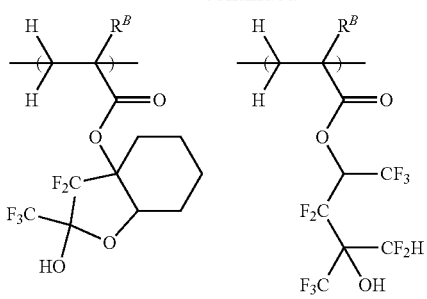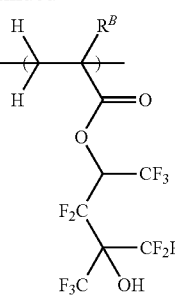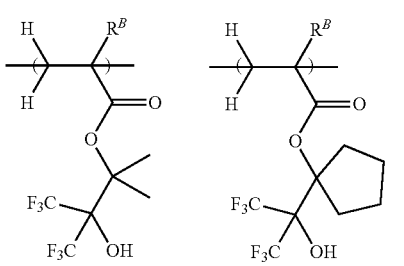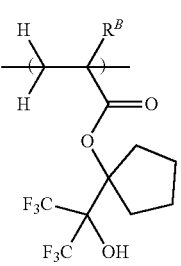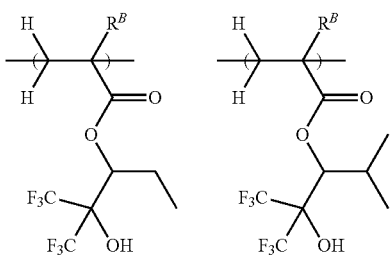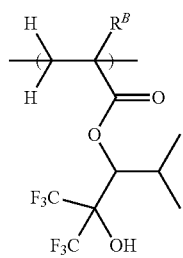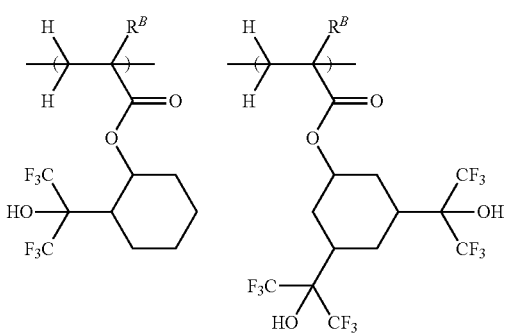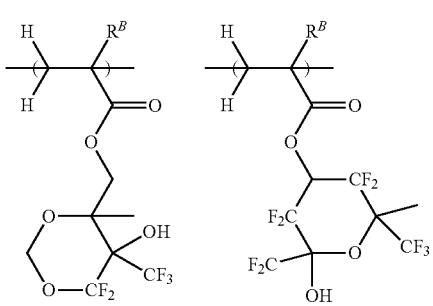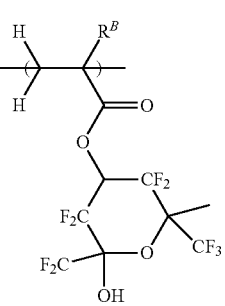
-continued
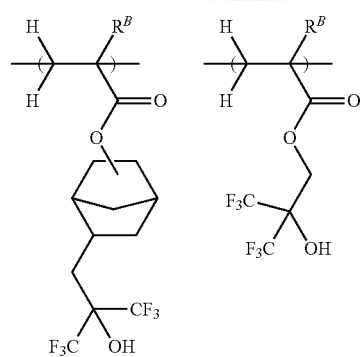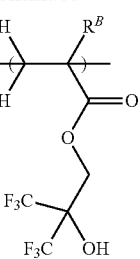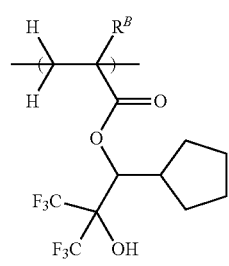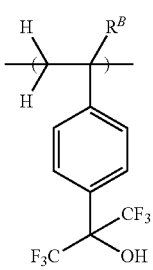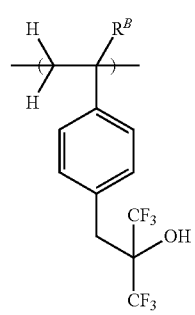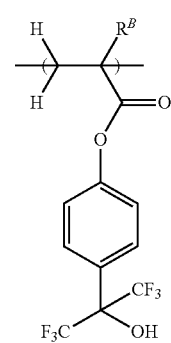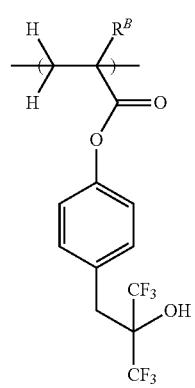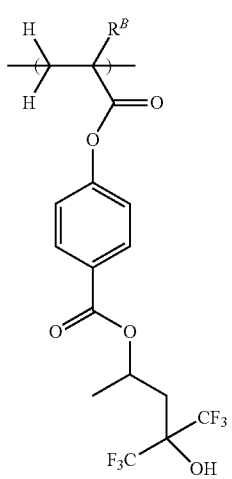

-continued

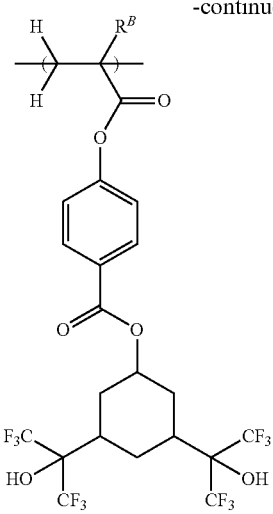

The amount of recurring units (b1) to (b6) incorporated is preferably 10 to 99 mol %, more preferably 20 to 90 mol %, even more preferably 30 to 85 mol %, based on the overall recurring units of the polymer. Any of recurring units (b1) to (b6) may be of one type or a combination of two or more types.

In a preferred embodiment, the polymer further comprises recurring units of at least one type selected from recurring units having the formula (c), recurring units having the formula (d), and recurring units having the formula (e). These units are also referred to as recurring units (c), (d) and (e).

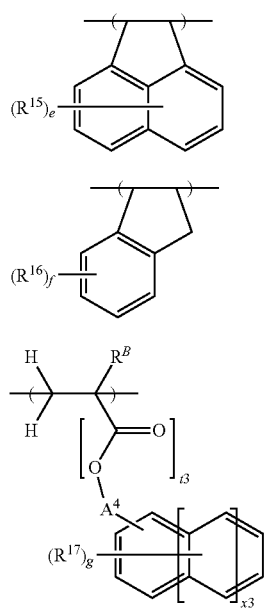

Herein $R^B$ is as defined above. $R^{15}$ and $R^{16}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group. $R^{17}$ is an acetyl, acetoxy, $C_1$-$C_{20}$ alkyl, $C_1$-$C_{20}$ primary alkoxy, $C_2$-$C_{20}$ secondary alkoxy, $C_2$-$C_{20}$ acyloxy, $C_2$-$C_{20}$ alkoxyalkyl, $C_2$-$C_{20}$ alkylthioalkyl, halogen, nitro or cyano group. $A^4$ is a single bond or a $C_1$-$C_{10}$ alkanediyl group which may contain an ether bond, e is an integer of 0 to 5, f is an integer of 0 to 3, g is an integer of 0 to 5, t3 is 0 or 1, and x3 is an integer of 0 to 2.

Examples of the alkanediyl group represented by $A^4$ include methylene, ethylene, propylene, butylene, pentylene, hexylene, and structural isomers of the carbon skeleton having a branched or cyclic structure. When an ether bond is contained in the alkanediyl group, in case t3=1 in formula (e), it may be at any position excluding between the α- and β-position carbons relative to the ester oxygen. In case t3=0 in formula (e), the atom bonding to the main chain is an ethereal oxygen atom, and a second ether bond may be contained at any position excluding between the α- and β-position carbons relative to that ethereal oxygen. As long as the carbon count of the alkanediyl group is up to 10, good solubility in alkaline developer is ensured.

Examples of the hydrocarbon moiety in the acyloxy, alkyl and alkoxy groups represented by $R^{15}$ and $R^{16}$ include methyl, ethyl, propyl, isopropyl, butyl, pentyl, hexyl, and structural isomers of the carbon skeleton having a branched or cyclic structure. A carbon count in the range ensures good solubility in alkaline developer.

$R^{17}$ is preferably selected from chlorine, bromine, iodine, methyl, ethyl, propyl, butyl, pentyl, hexyl and structural isomers thereof, cyclopentyl, cyclohexyl, methoxy, ethoxy, propoxy, butoxy, pentyloxy, hexyloxy and structural isomers of its hydrocarbon moiety, cyclopentyloxy, and cyclohexyloxy. Inter alia, methoxy and ethoxy are preferred. Also, an acyloxy group may be readily introduced into a polymer even at the end of polymerization by the chemical modification method and is thus advantageously used for fine adjustment of solubility of a base polymer in alkaline developer. Suitable acyloxy groups include methylcarbonyloxy, ethylcarbonyloxy, propylcarbonyloxy, butylcarbonyloxy, pentylcarbonyloxy, hexylcarbonyloxy and structural isomers thereof, cyclopentylcarbonyloxy, cyclohexylcarbonyloxy, and benzoyloxy groups. As long as the carbon count is not more than 20, the group is effective for appropriately controlling and adjusting (typically reducing) the solubility of a base polymer in alkaline developer and for preventing scum or development defects from forming. Of the preferred substituent groups mentioned above, chlorine, bromine, iodine, methyl, ethyl, and methoxy are especially useful because corresponding monomers are readily furnished.

In formula (e), x3 is an integer of 0 to 2. The relevant skeleton is a benzene skeleton in case of x3=0, a naphthalene skeleton in case of x3=1, and an anthracene skeleton in case of x3=2. In case of x3=0, preferably g is an integer of 0 to 3. In case of x3=1 or 2, preferably g is an integer of 0 to 4.

Where the recurring units (e) are free of a linker (—CO—O-$A^4$-), that is, have formula (e) wherein t3=0 and $A^4$ is a single bond, indicating that aromatic ring is directly bonded to the polymer backbone, suitable recurring units (e) include those derived from styrene, 4-chlorostyrene, 4-methylstyrene, 4-methoxystyrene, 4-bromostyrene, 4-acetoxystyrene, 2-hydroxypropylstyrene, 2-vinylnaphthalene, 3-vinylnaphthalene, 1-vinylanthracene, 2-vinylanthracene, and 9-vinylanthracene.

Where the recurring units (e) have a linker (—CO—O-$A^4$-), that is, have formula (e) wherein t3=1, preferred examples of the recurring units (e) are given below, but not limited thereto. Herein $R^B$ is as defined above.

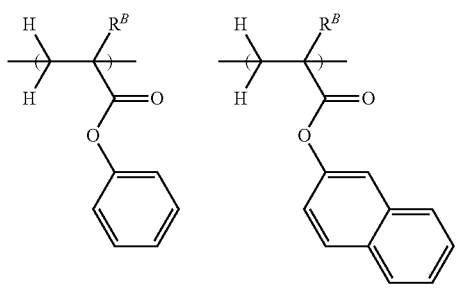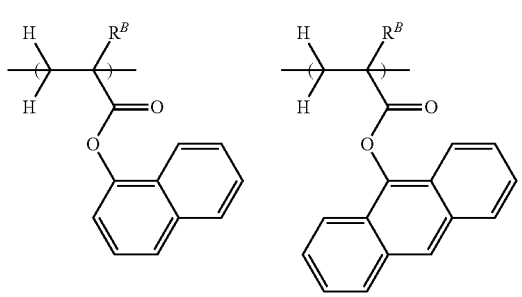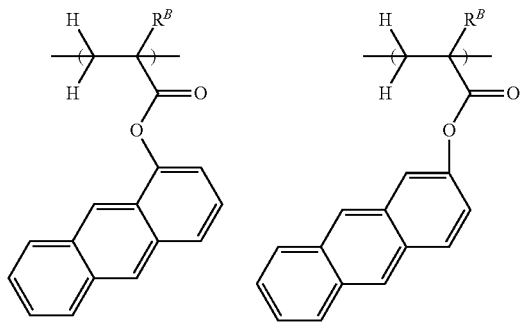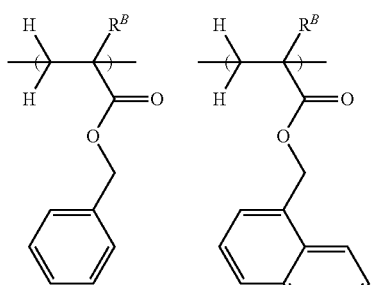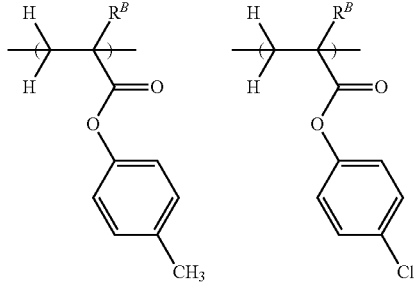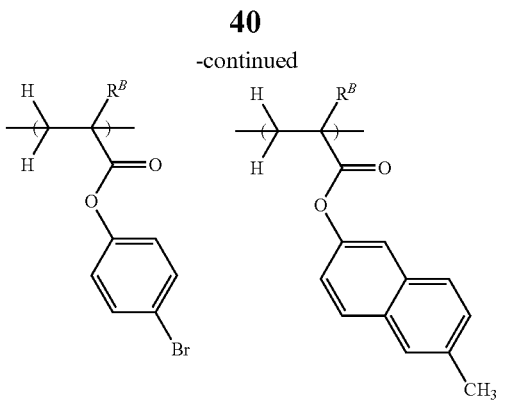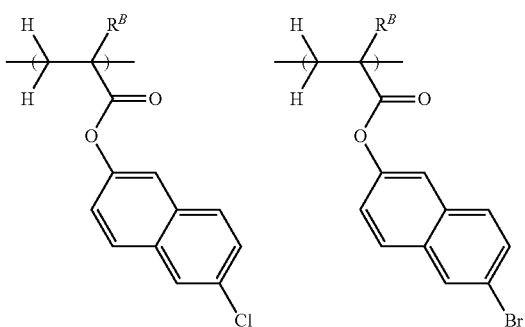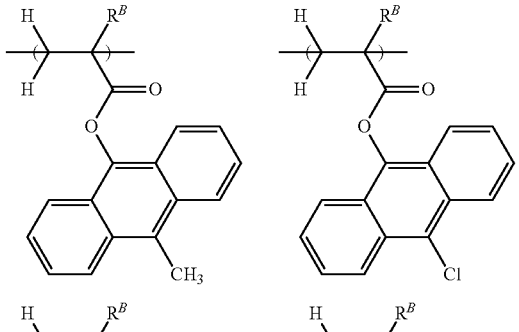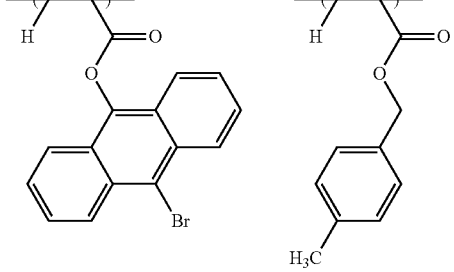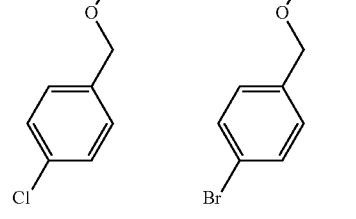

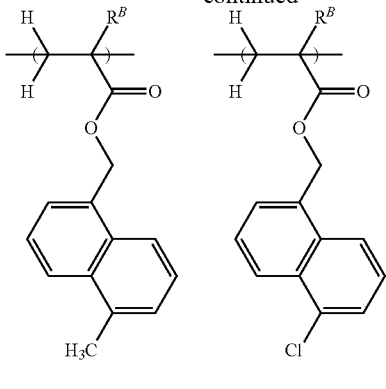

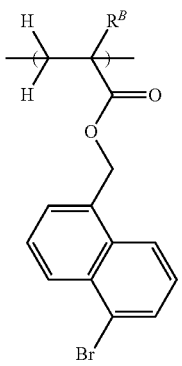

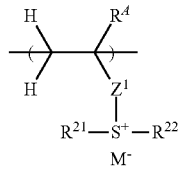

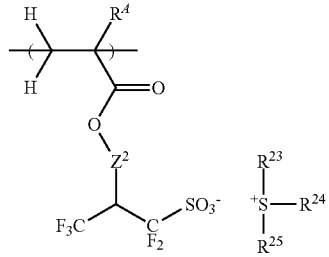

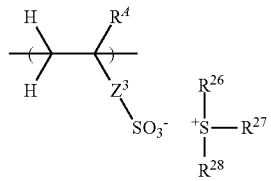

When recurring units of at least one type selected from recurring units (c) to (e) are incorporated in the polymer, better performance is obtained because not only the aromatic ring possesses etching resistance, but the cyclic structure incorporated into the main chain also exerts the effect of improving resistance to etching and EB irradiation during pattern inspection steps.

In an embodiment wherein a negative resist composition comprises a polymer containing recurring units (a), recurring units of at least one type selected from recurring units (b1) to (b6), and recurring units of at least one type selected from recurring units (c) to (e) at the same time, when a resist film of the resist composition is exposed to EB or EUV through a mask pattern including both an isolated line pattern and an isolated space pattern, it is possible to strongly suppress the pattern density dependence and to achieve a high resolution at the same time.

For the effect of improving etch resistance, the content of recurring units (c) to (e) is preferably at least 2 mol %, more preferably at least 5 mol % and up to 35 mol % and more preferably up to 20 mol %, based on the overall recurring units of the polymer. The recurring units (c) to (e) may be of one type or a combination of two or more.

In a preferred embodiment, the polymer further comprises recurring units of at least one type selected from recurring units having the formula (f1), recurring units having the formula (f2), and recurring units having the formula (f3). These units are also referred to as recurring units (f1), (f2) and (f3).

In formulae (f1) to (f3), $R^A$ is as defined above. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl, $C_2$-$C_6$ alkenediyl or phenylene group which may contain a carbonyl, ester bond, ether bond or hydroxyl moiety. $Z^2$ is a single bond or —$Z^{21}$—C(=O)—O, wherein $Z^{21}$ is a $C_1$-$C_{20}$ divalent hydrocarbon group which may contain a heteroatom. $Z^3$ is a single bond, methylene, ethylene, phenylene, fluorinated phenylene, —O—$Z^{31}$—, —C(=O)—O—$Z^{31}$— or —C(=O)—NH—$Z^{31}$—, wherein $Z^{31}$ is a $C_1$-$C_6$ alkanediyl, $C_2$-$C_6$ alkenediyl or phenylene group which may contain a carbonyl, ester bond, ether bond or hydroxyl moiety.

In formulae (f1) to (f3), $R^{21}$ to $R^{28}$ are each independently a $C_1$-$C_{20}$ monovalent hydrocarbon group which may contain a heteroatom. In the hydrocarbon group, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain a hydroxyl moiety, cyano moiety, carbonyl moiety, ether bond, ester bond, sulfonic acid ester bond, carbonate bond, lactone ring, sultone ring, carboxylic anhydride or haloalkyl moiety. Also, $R^{21}$ and $R^{22}$ may bond together to form a ring with the sulfur atom to which they are attached, any two of $R^{23}$, $R^{24}$ and $R^{25}$ may bond together to form a ring with the sulfur atom to which they are attached, any two of $R^{26}$, $R^{27}$ and $R^{28}$ may bond together to form a ring with the sulfur atom to which they are attached. M⁻ is a non-nucleophilic counter ion.

In formula (f2), $Z^2$ may be —$Z^{21}$—C(=O)—O— wherein $Z^{21}$ is an optionally heteroatom-containing divalent hydrocarbon group. Examples of the hydrocarbon group $Z^{21}$ are given below, but not limited thereto.

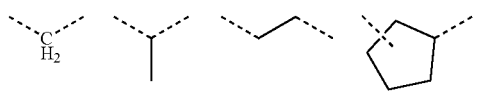

-continued

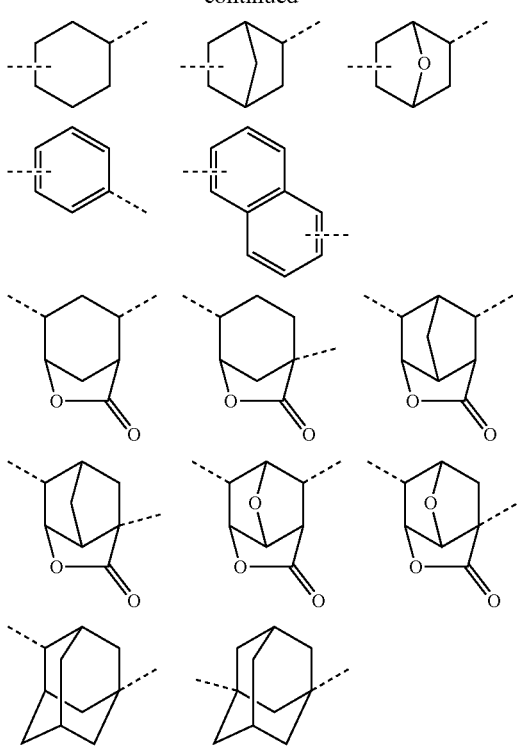

Where any two of $R^{23}$, $R^{24}$ and $R^{25}$ or any two of $R^{26}$, $R^{27}$ and $R^{28}$ in formulae (f2) and (f3) bond together to form a ring with the sulfur atom to which they are attached, examples of the thus formed sulfonium cation are given below.

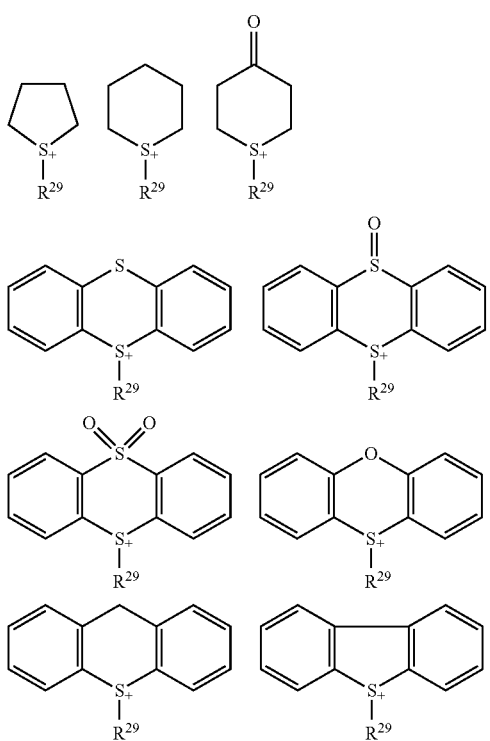

-continued

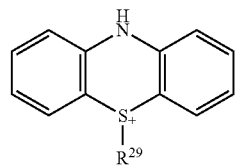

It is noted that $R^{29}$ is the same as defined and exemplified for $R^{21}$ to $R^{28}$.

Exemplary structures of the sulfonium cation in formulae (f2) and (f3) are shown below, but not limited thereto.

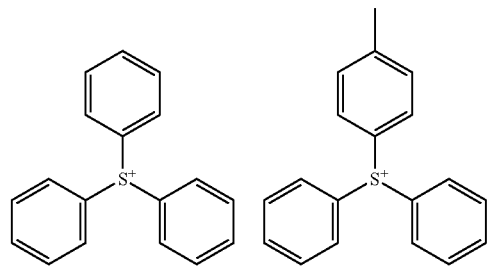

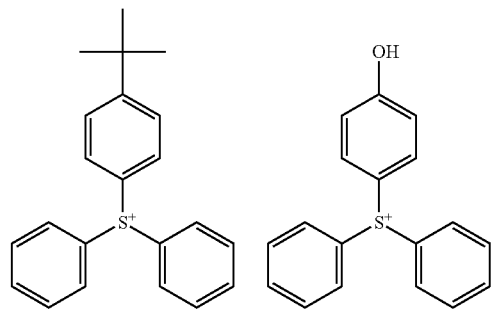

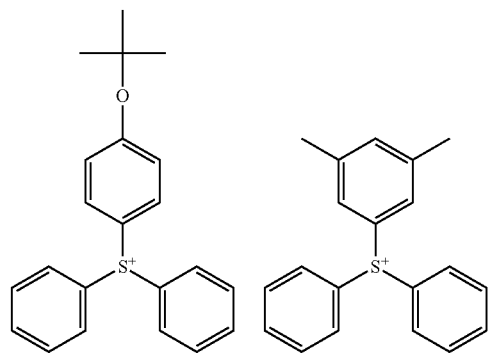

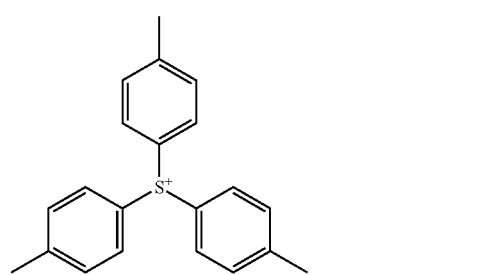

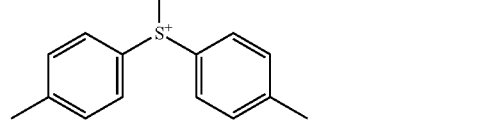

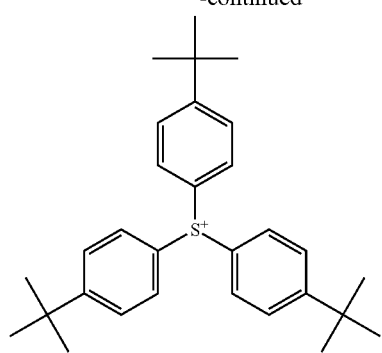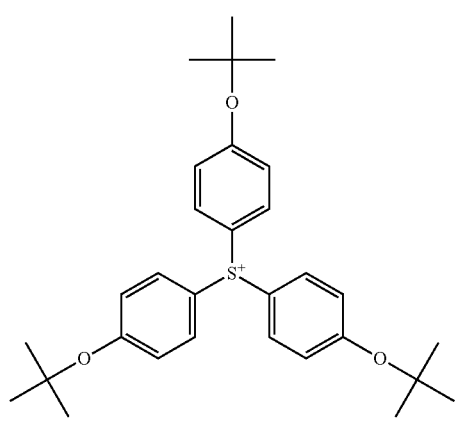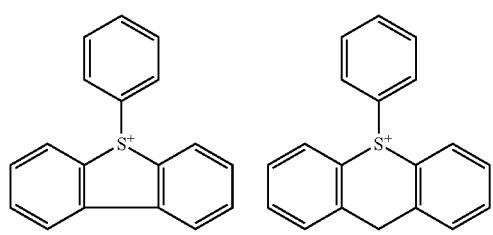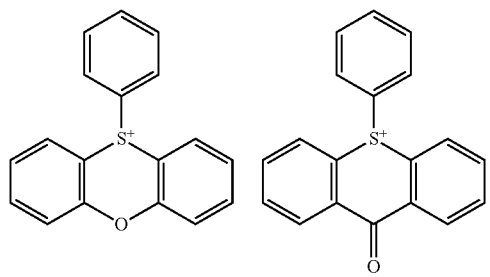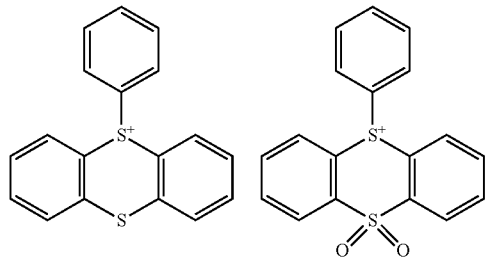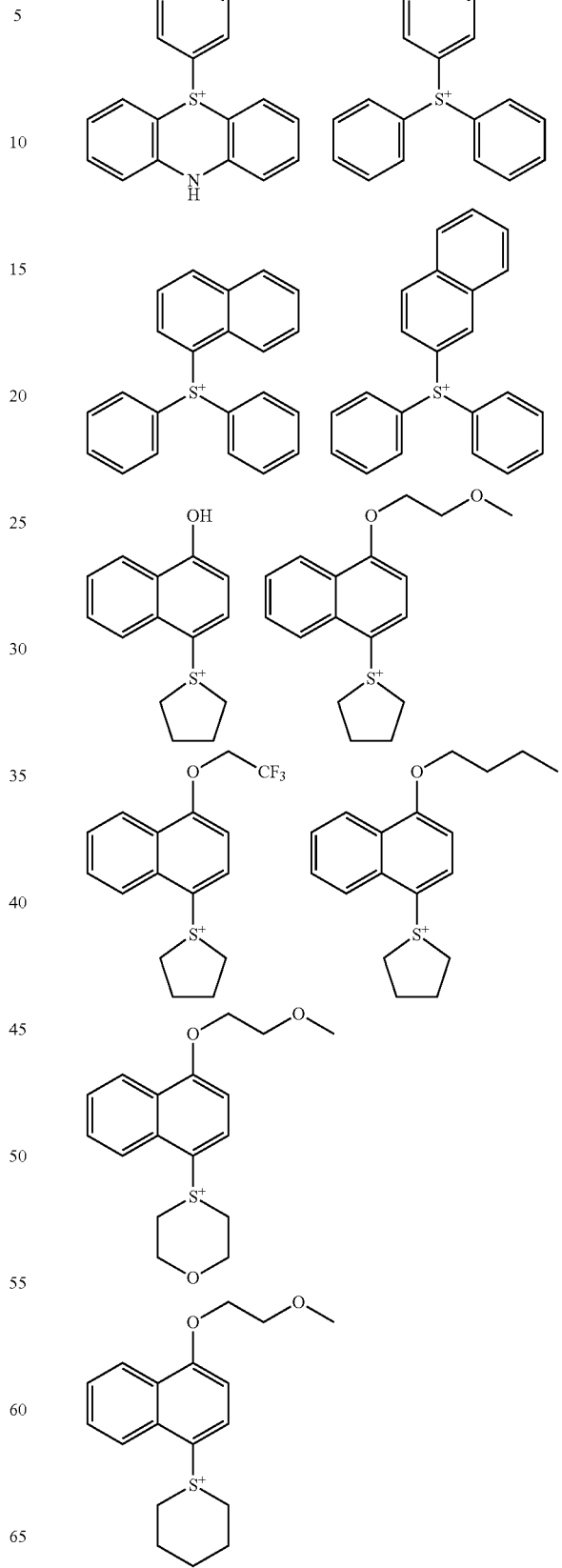

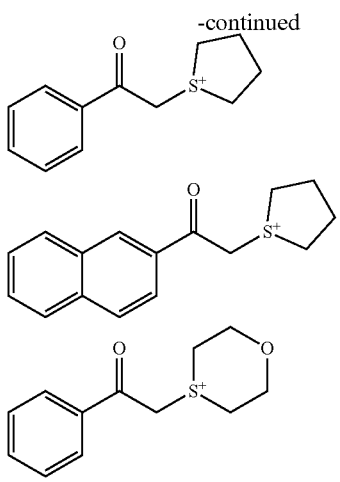

The recurring units (f1) to (f3) are units capable of generating an acid upon receipt of high-energy radiation. These units incorporated into a polymer ensure appropriate control of acid diffusion and formation of a pattern with minimal LER. Since the acid-generating unit is bound to a polymer, the chemical flare phenomenon that the acid volatilizes from the exposed region and re-deposits on the unexposed region during bake in vacuum is suppressed. This is effective for reducing LER and for suppressing unwanted negative-toning reaction in the unexposed region for thereby reducing defects.

When the polymer contains recurring units (f1) to (f3), the content of recurring units (f1) to (f3) is preferably 0.5 to 20 mol %, more preferably 1 to 10 mol %, based on the overall recurring units of the polymer. A content in the range prevents any drop of solubility of the polymer in resist solvent and avoids the risk of defect formation.

The polymer should preferably have a weight average molecular weight (Mw) of 1,000 to 50,000, and more preferably 1,000 to 10,000, as measured by GPC versus polystyrene standards.

The polymer preferably has a narrow molecular weight distribution or dispersity (Mw/Mn) of 1.0 to 2.0, more preferably 1.0 to 1.8. A polymer with such a narrow dispersity eliminates any foreign particles left on the pattern or profile degradation of the pattern after development.

Negative Resist Composition

A further embodiment of the invention is a negative resist composition comprising a base polymer containing the polymer defined above. The polymer may be a single polymer or a mixture of two or more.

Preferably, the negative resist composition further comprises an acid generator or compound capable of generating an acid upon exposure to high-energy radiation. The negative resist composition containing an acid generator functions as a chemically amplified negative resist composition. The acid generator may be selected from well-known ones, depending on the desired physical properties to be adjusted. Suitable acid generators include sulfonium salts, iodonium salts, sulfonyldiazomethane, N-sulfonyloxyimide, and oxime-O-sulfonate acid generators. These acid generators may be used alone or in admixture of two or more. Examples of the acid generator are described in JP-A 2008-111103, paragraphs [0122]-[0142] (U.S. Pat. No. 7,537,880).

Of the acid generators, an acid generator of arene sulfonate type is preferred because it generates an acid having a sufficient strength to generate a benzyl cation from recurring unit (a) to induce crosslinking or dehydration reaction.

The preferred acid generator is a compound having a sulfonate anion of the structure shown below and a pairing cation which is as exemplified above as the sulfonium cation in formulae (f2) and (f3).

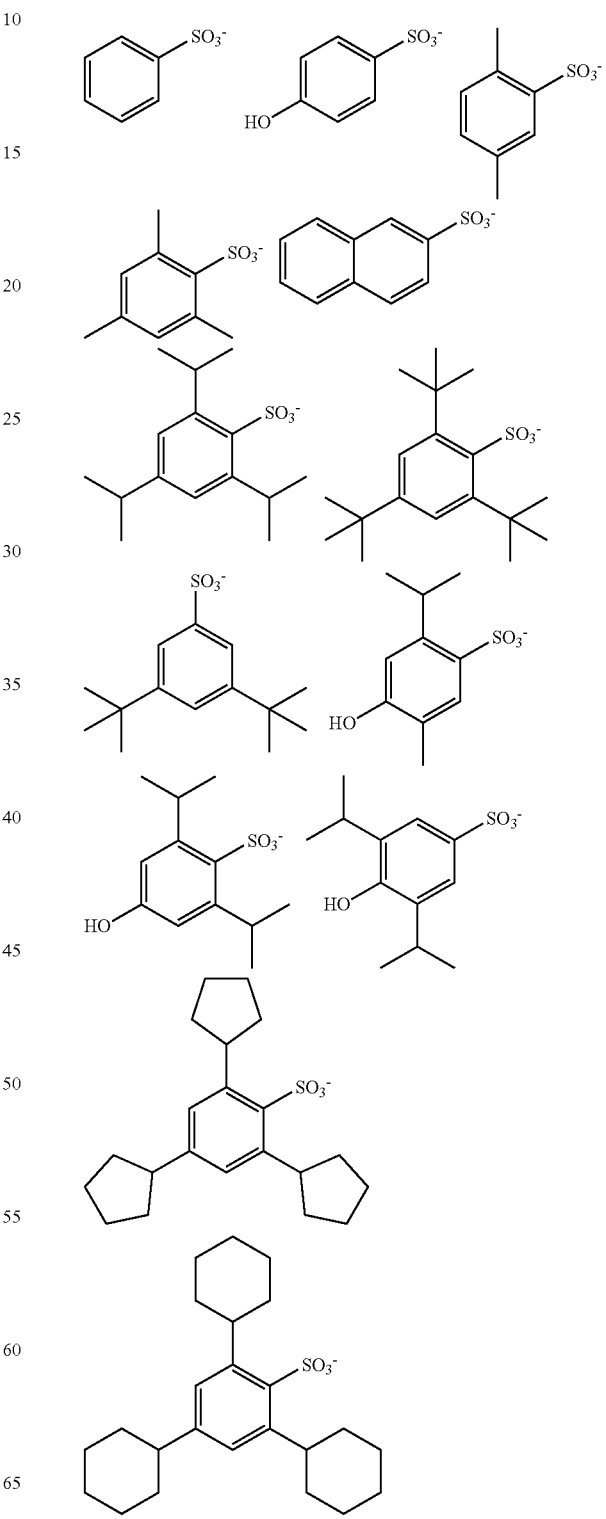

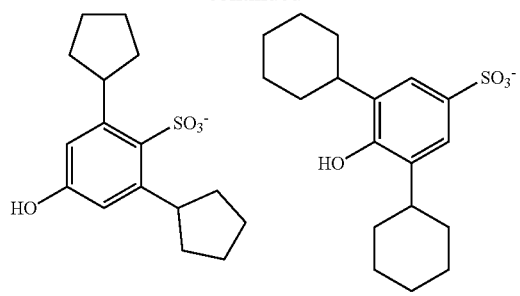
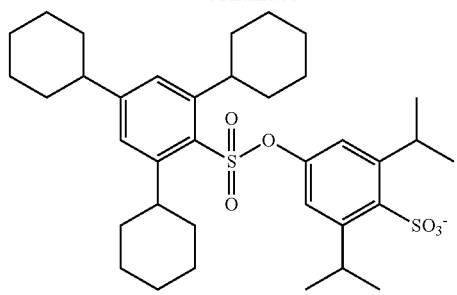
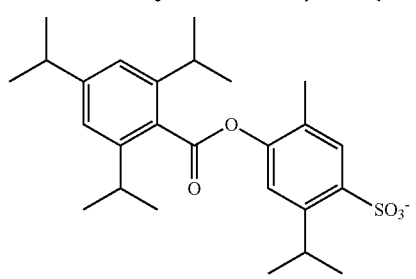
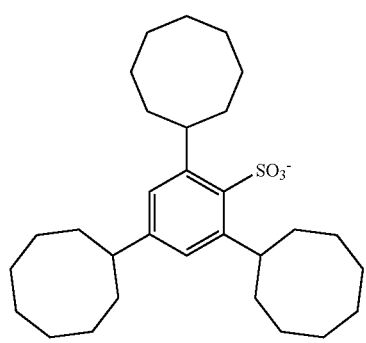
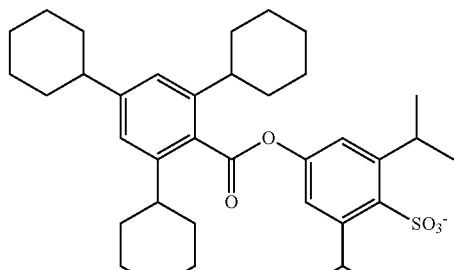
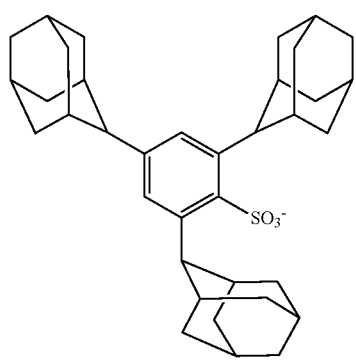
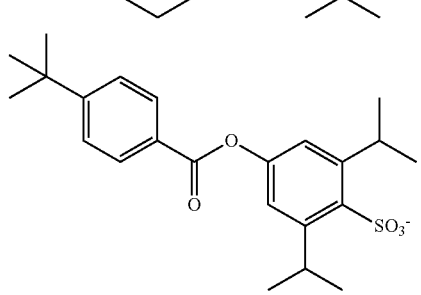
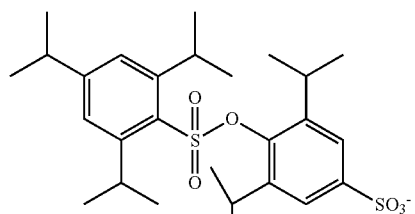
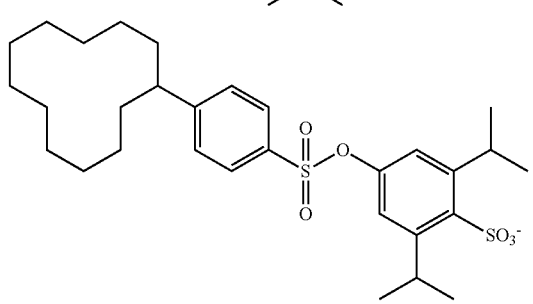
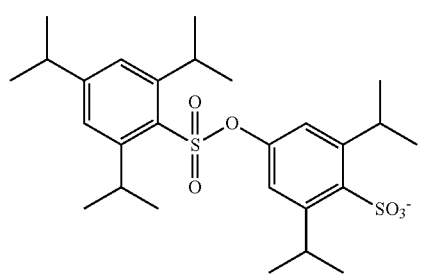
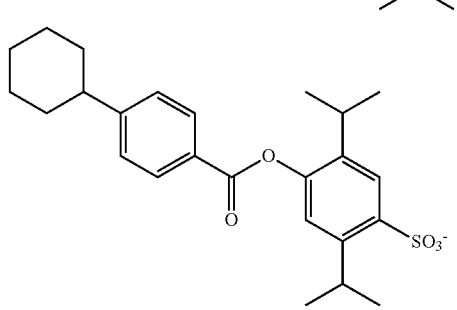

51
-continued
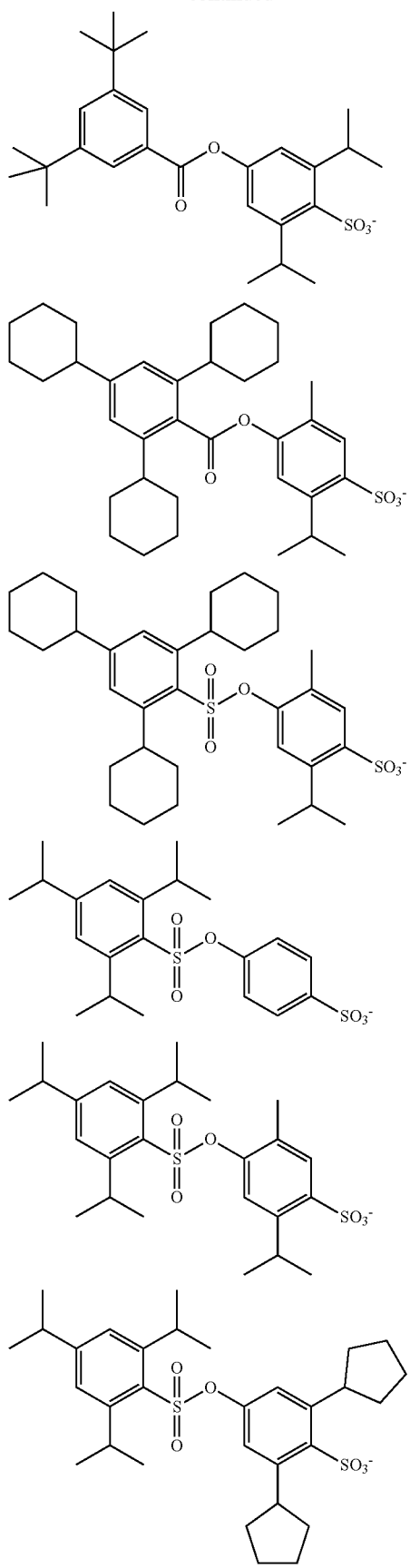
52
-continued
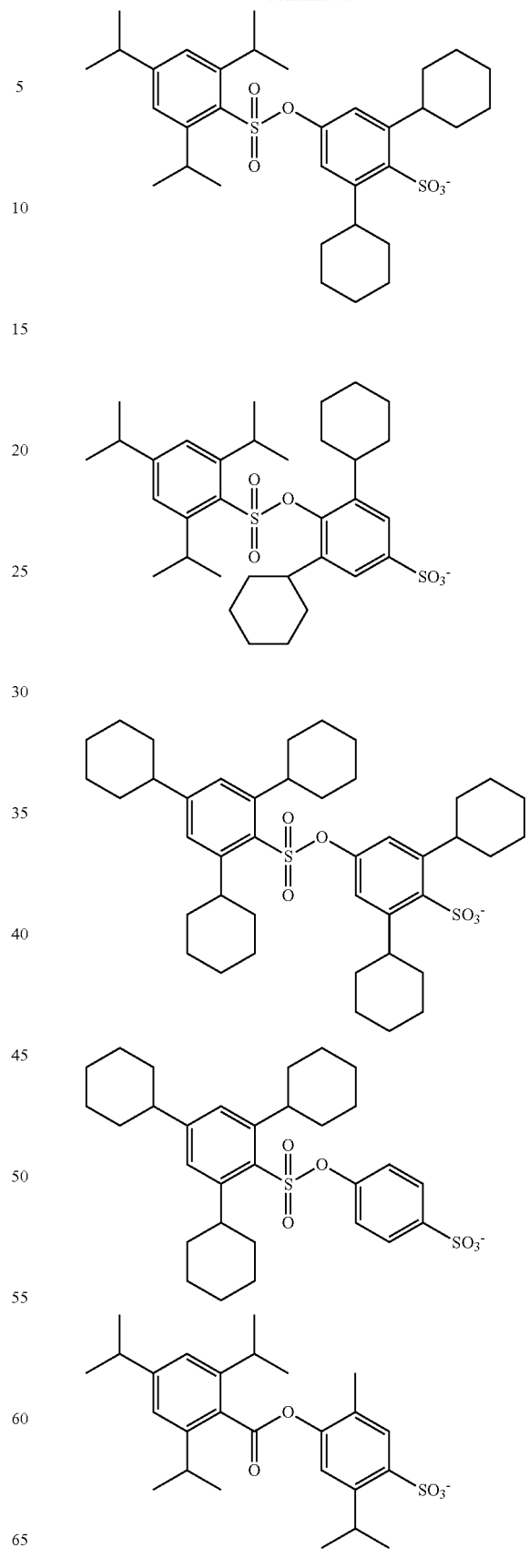

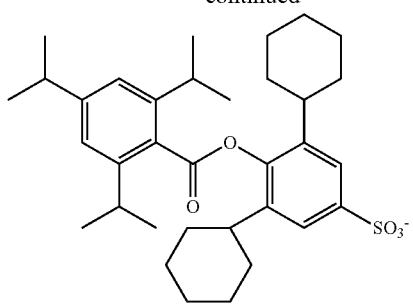
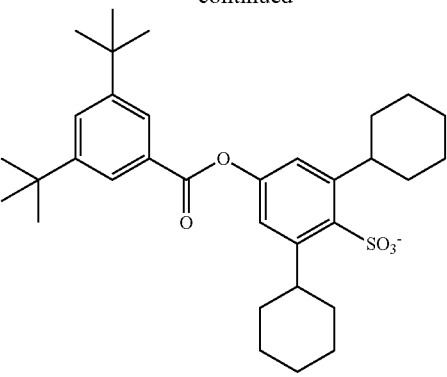
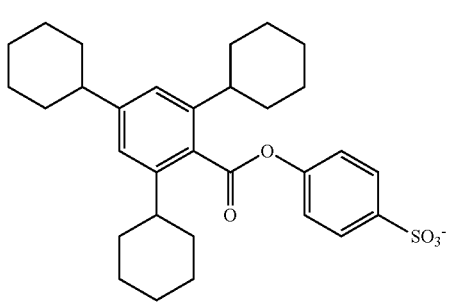
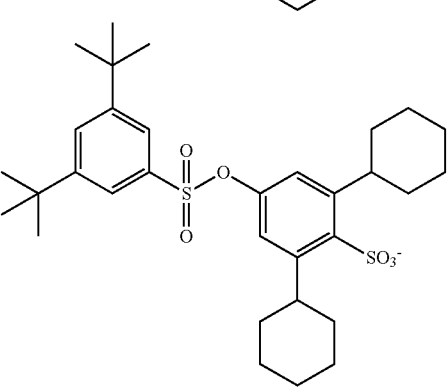
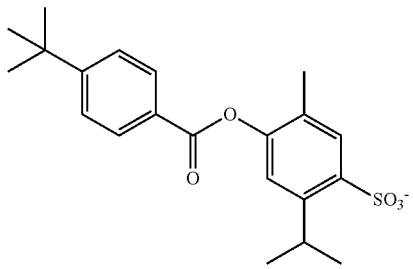
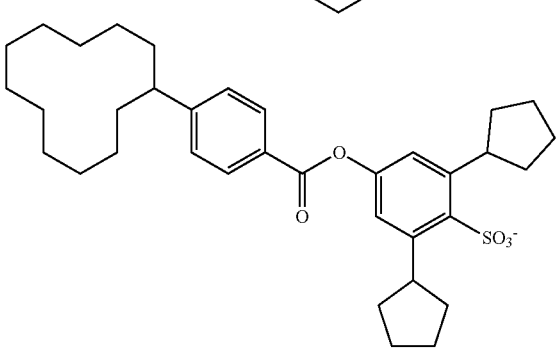
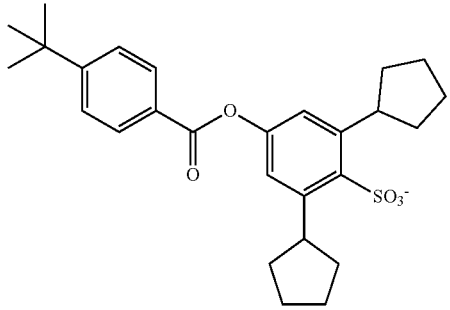
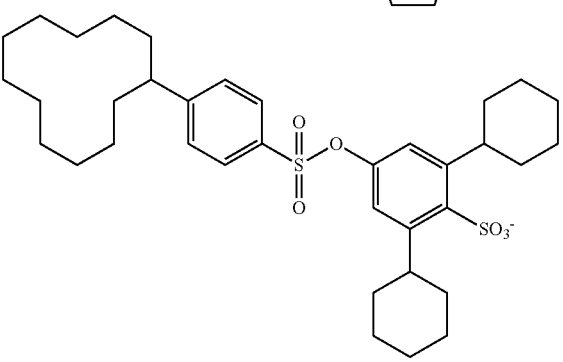
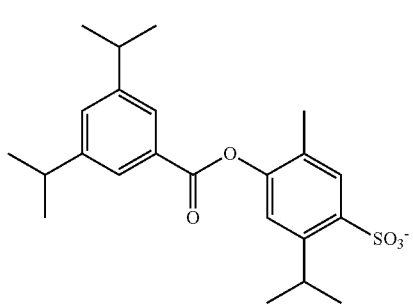
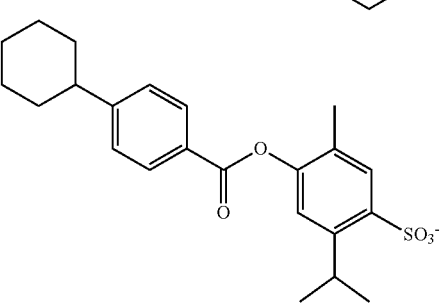

55
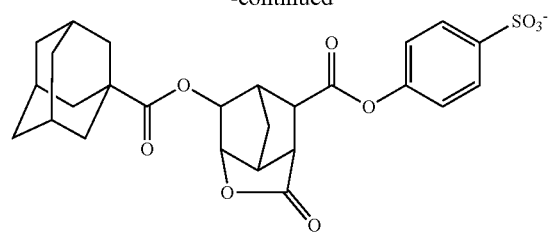
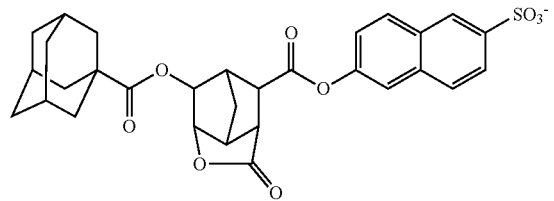
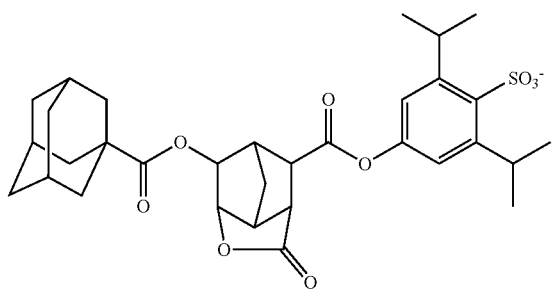
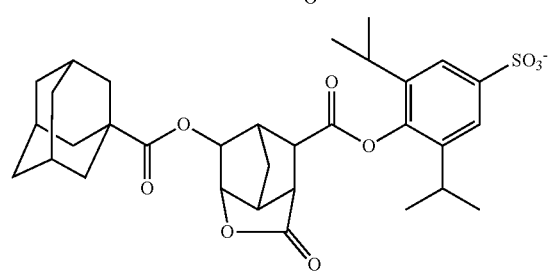
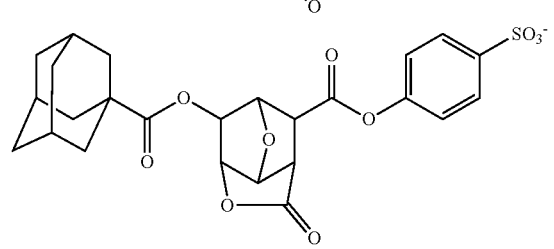
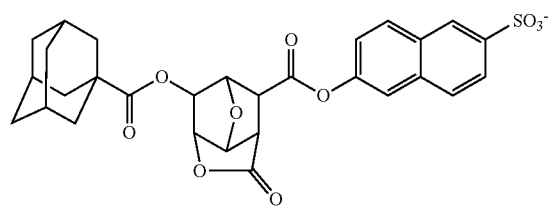
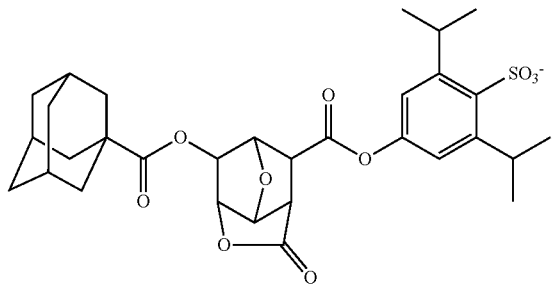
56
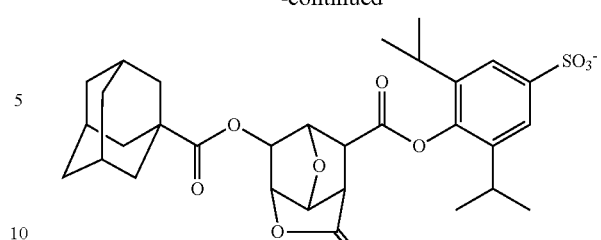
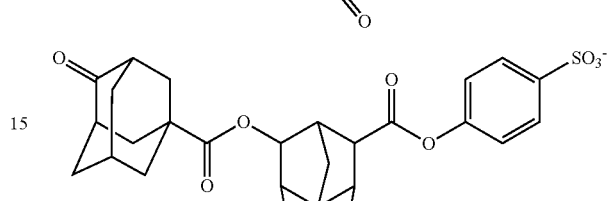
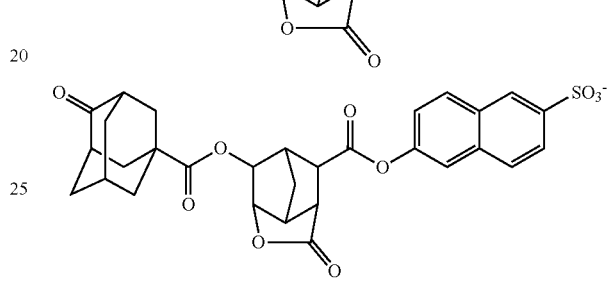
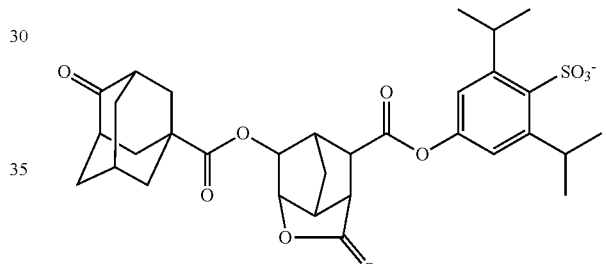
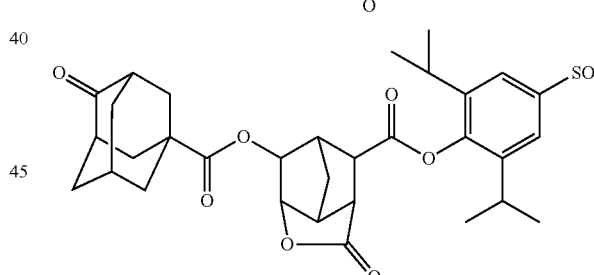
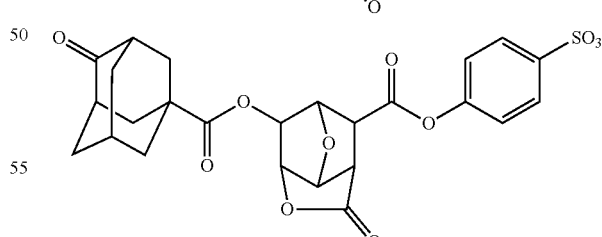
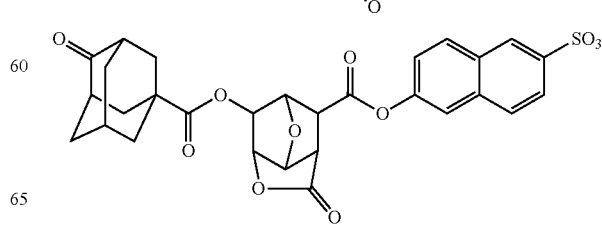

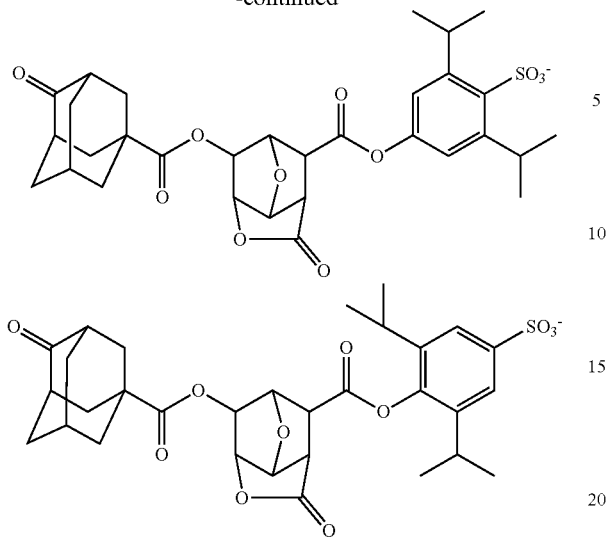

In the resist composition, the acid generator is preferably present in an amount of 1 to 20 parts by weight, more preferably 2 to 15 parts by weight per 100 parts by weight of the base polymer. The acid generator may be used alone or in admixture.

For the purposes of adjusting a sensitivity and obtaining a high resolution, the negative resist composition preferably contains a quencher or acid diffusion inhibitor. Suitable quenchers include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, ammonium salts, and carboxylic acid salts. While many exemplary compounds are described in Patent Document 2, JP-A 2008-111103, paragraphs [0146]-[0164], and JP 3790649, any of these compounds may be used herein.

A salt having the formula (2) is also preferred as the quencher.

In formula (2), $R^{101}$ is a $C_1$-$C_{20}$ alkyl, $C_2$-$C_{20}$ alkenyl and $C_6$-$C_{36}$ aryl groups, which may contain fluorine, nitrogen, ether bond, ester bond, lactone ring, lactam ring, carbonyl moiety or hydroxyl moiety. The alkyl and alkenyl group may be straight, branched or cyclic. $Q^+$ is a sulfonium, iodonium or ammonium cation.

The salt having formula (2) functions as a quencher because it undergoes exchange reaction with the acid generated upon exposure. Since the salt is an ionic compound, it will not volatilize by heat. By contrast, amine compounds commonly used as the quencher will volatilize by the heat generated during bake or imaging. A resist composition containing an ionic compound as the quencher is advantageous in that it is not affected by the heat generated during bake or imaging and the temperature dependence of pattern feature size is minimized.

Examples of the anion in the salt having formula (2) are shown below, but not limited thereto.

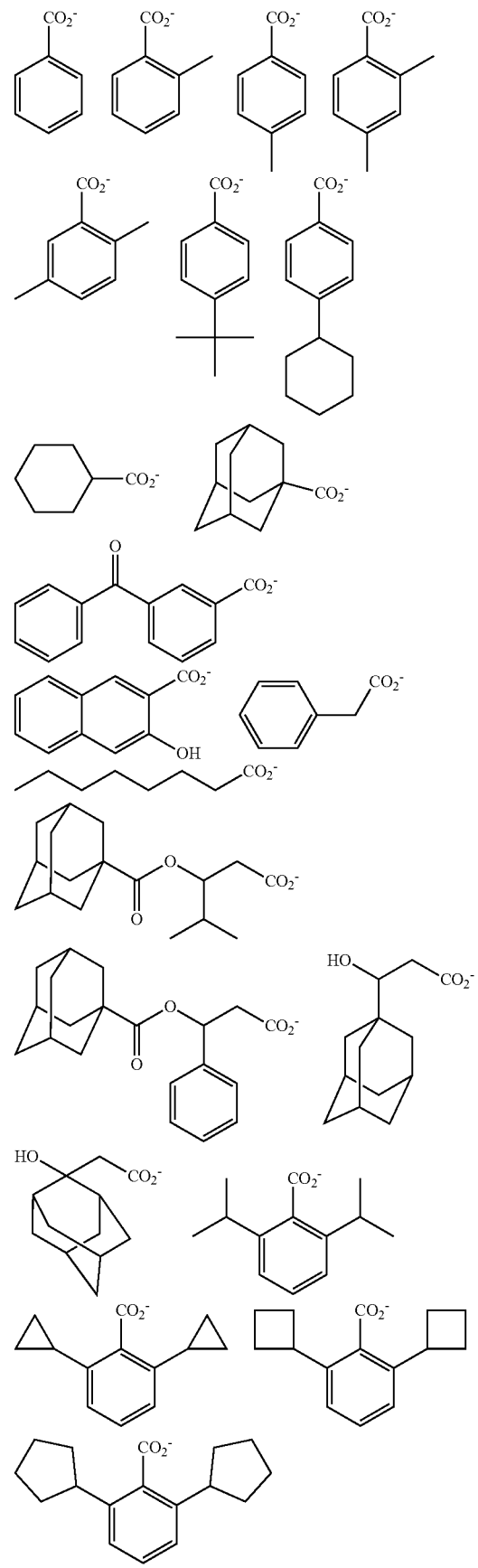

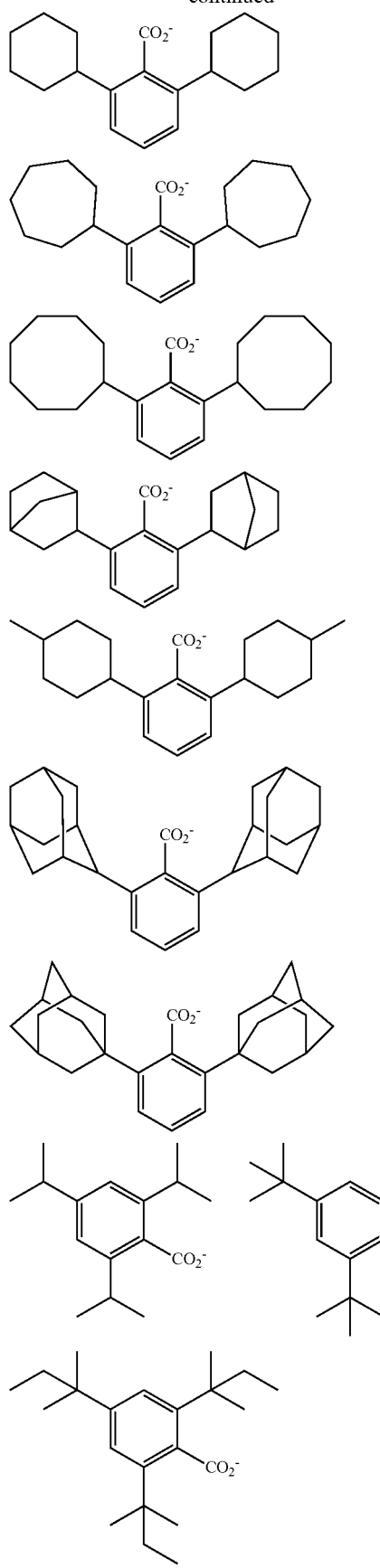
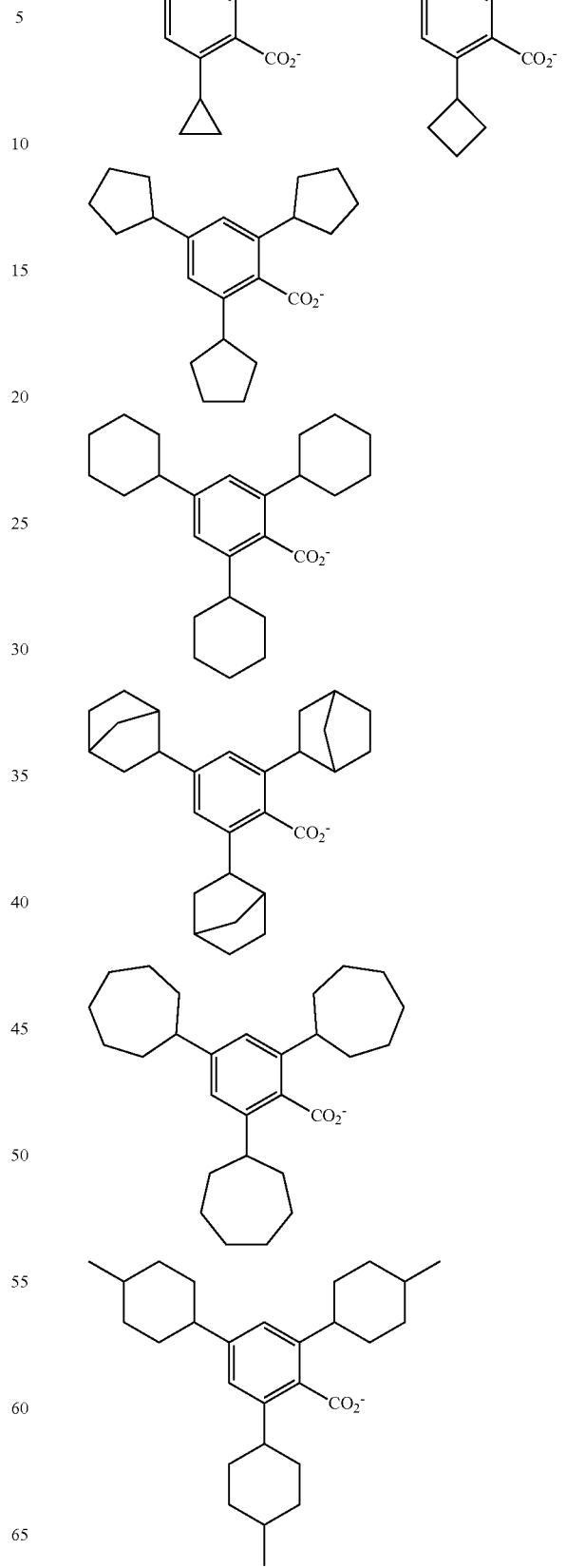

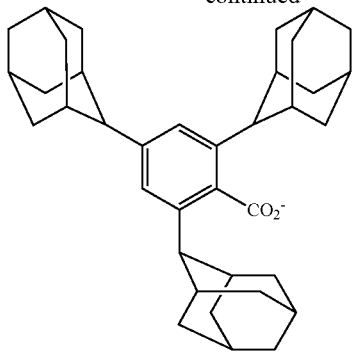

A salt having the formula (3) is also preferred as the quencher.

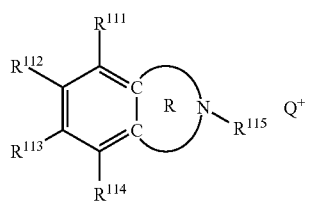

(3)

In formula (3), $R^{111}$ to $R^{114}$ are each independently hydrogen, $-L^A-CO_2^-$ or a $C_1-C_{20}$ monovalent hydrocarbon group which may contain a heteroatom. A pair of $R^{111}$ and $R^{112}$, $R^{112}$ and $R^{113}$, or $R^{113}$ and $R^{114}$ may bond together to form a ring with the carbon atoms to which they are attached. $L^A$ is a single bond or a $C_1-C_{20}$ divalent hydrocarbon group which may contain a heteroatom. $R^{115}$ is hydrogen or a $C_1-C_{20}$ monovalent hydrocarbon group which may contain a heteroatom.

In formula (3), the ring R is a ring of 2 to 6 carbon atoms including the carbon and nitrogen atoms depicted in the formula, in which some or all carbon-bonded hydrogen may be substituted by a $C_1-C_{20}$ monovalent hydrocarbon moiety or $-L^A-CO_2^-$, or some carbon may be replaced by sulfur, oxygen or nitrogen. The ring may be alicyclic or aromatic and is preferably a 5- or 6-membered ring. Examples include pyridine, pyrrole, pyrrolidine, piperidine, pyrazole, imidazoline, pyridazine, pyrimidine, pyrazine, imidazoline, oxazole, thiazole, morpholine, thiazine, and triazole rings.

The carboxylic onium salt having formula (3) has at least one $-L^A-CO_2^-$ group.

Examples of the anion in the salt having formula (3) are shown below, but not limited thereto.

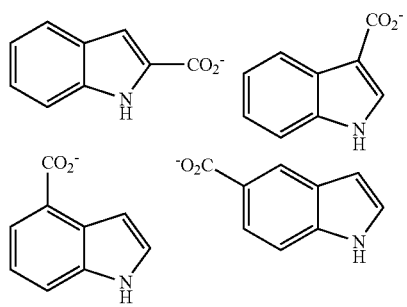

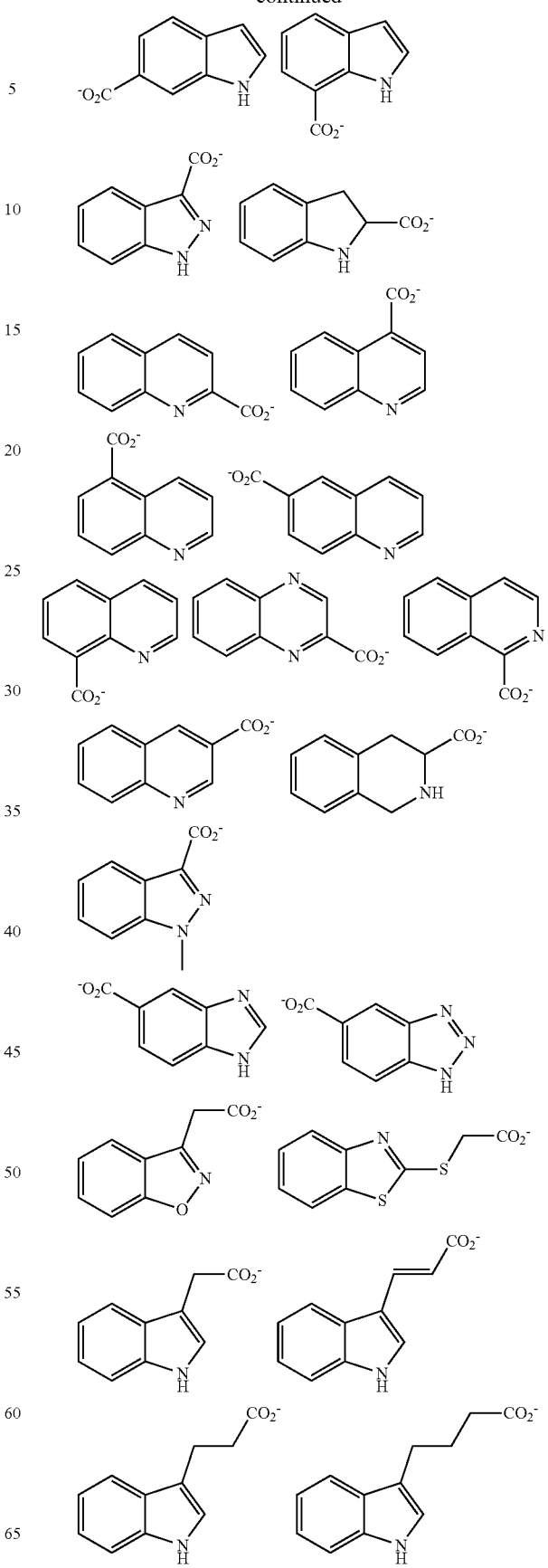

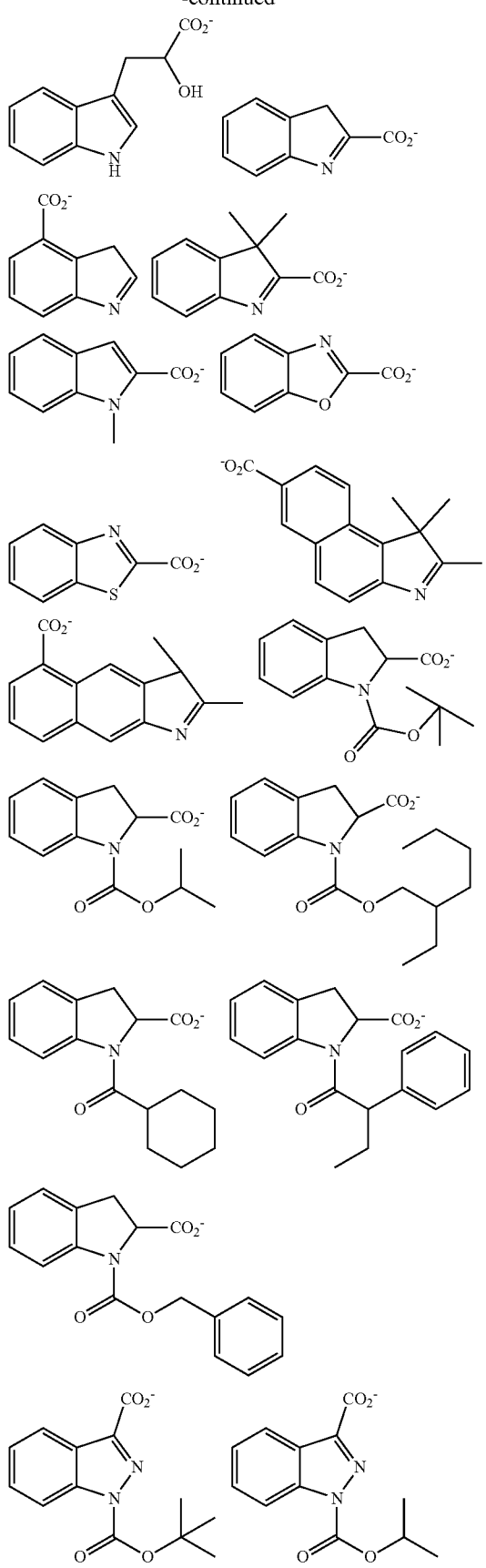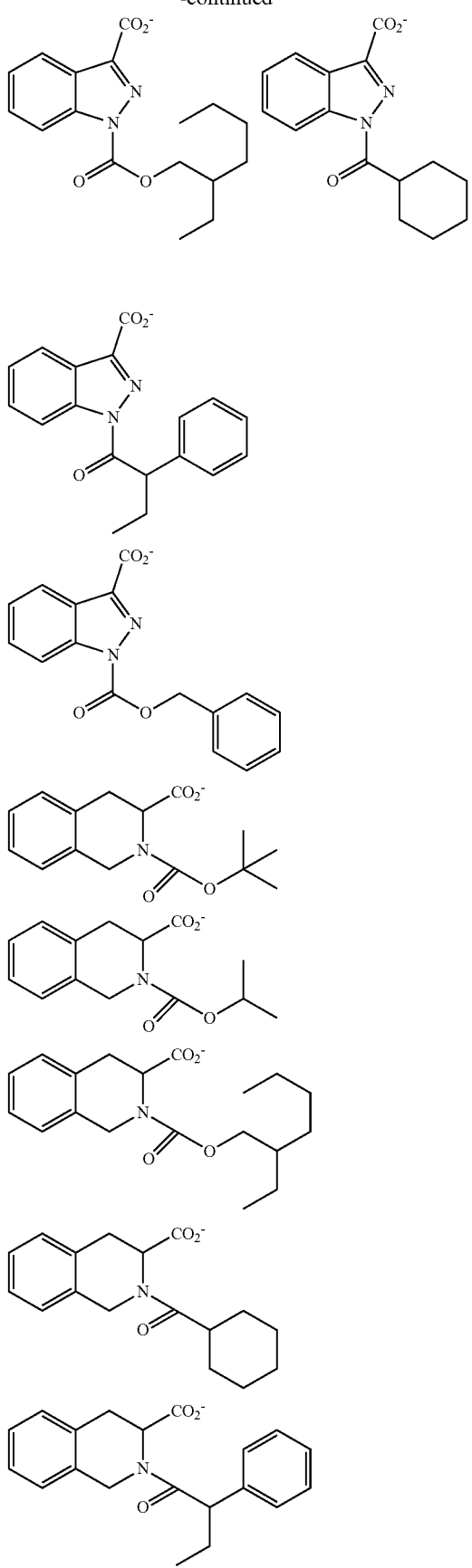

-continued

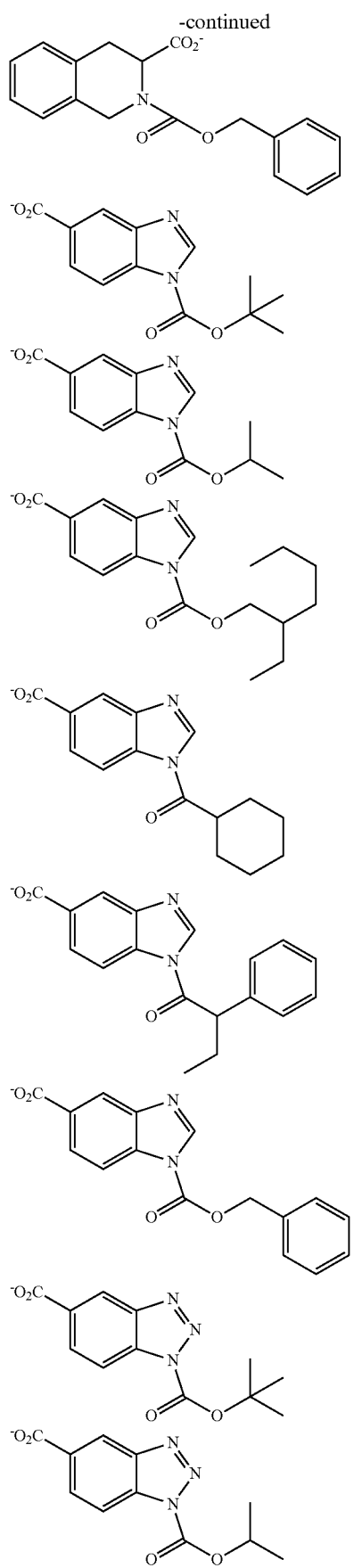

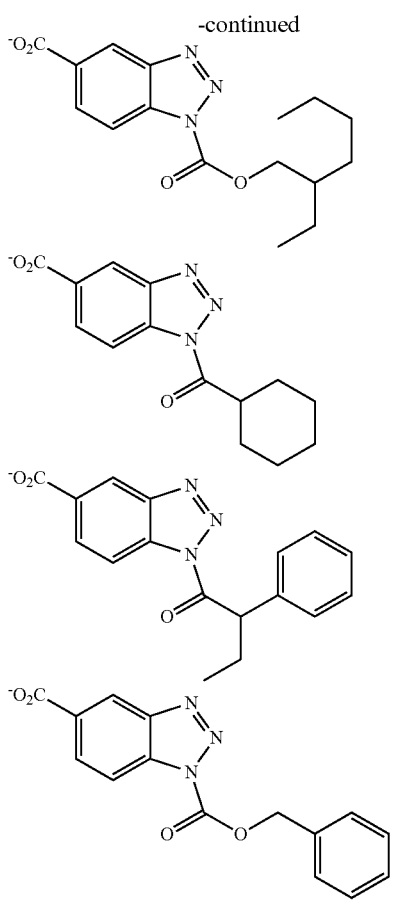

Also, a betaine type compound having the formula (4) is preferred as the quencher.

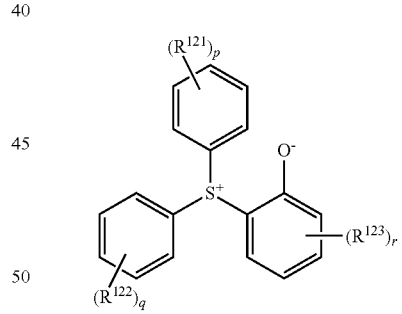

(4)

In formula (4), $R^{121}$, $R^{122}$ and $R^{123}$ are each independently a $C_1$-$C_{20}$ monovalent hydrocarbon group which may contain a heteroatom. In the hydrocarbon group, some hydrogen may be substituted by a moiety containing a heteroatom such as oxygen, sulfur, nitrogen or halogen, or some carbon may be replaced by a moiety containing a heteroatom such as oxygen, sulfur or nitrogen, or the carbon atom (in the hydrocarbon group) bonded to the benzene ring may be replaced by a moiety containing a heteroatom such as oxygen, sulfur or nitrogen, so that the group may contain a hydroxyl moiety, cyano moiety, carbonyl moiety, ether bond, thioether bond, ester bond, sulfonic acid ester bond, carbonate bond, carbamate bond, lactone ring, sultone ring, carboxylic anhydride or haloalkyl moiety.

In formula (4), p and q are each independently an integer of 0 to 5, and r is an integer of 0 to 4. From the standpoints of ease of synthesis and availability of reactants, p, q and r each are preferably 0, 1 or 2.

When p is 2 to 5, two adjoining $R^{121}$ may bond together to form a ring with the carbon atoms to which they are attached. When q is 2 to 5, two adjoining $R^{122}$ may bond together to form a ring with the carbon atoms to which they are attached. When r is 2 to 4, two adjoining $R^{123}$ may bond together to form a ring with the carbon atoms to which they are attached.

Examples of the compound having formula (4) are shown below, but not limited thereto.

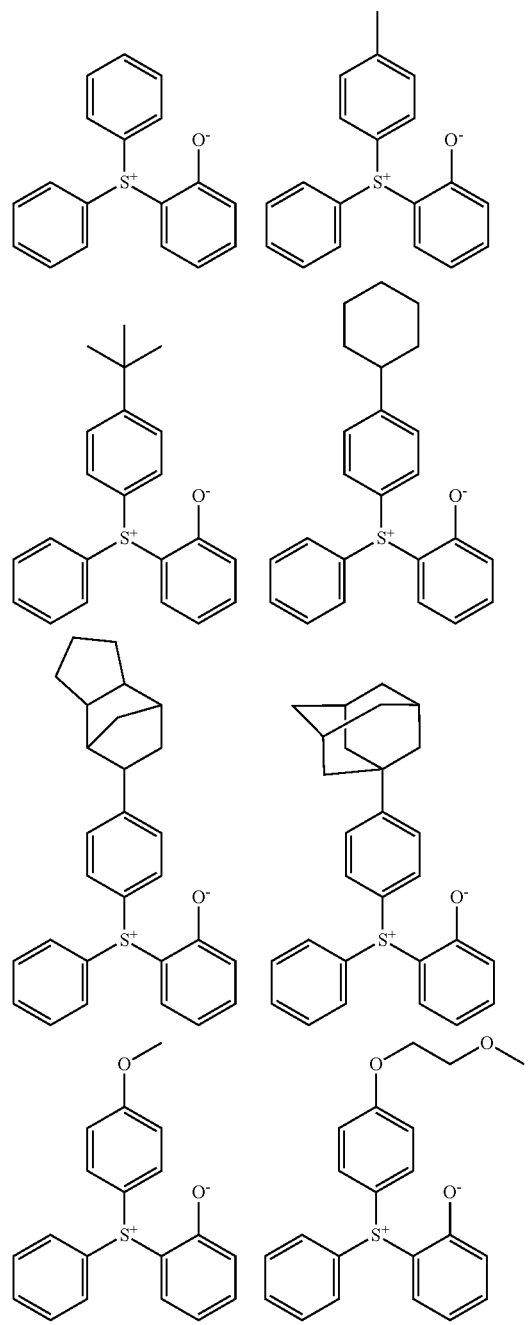

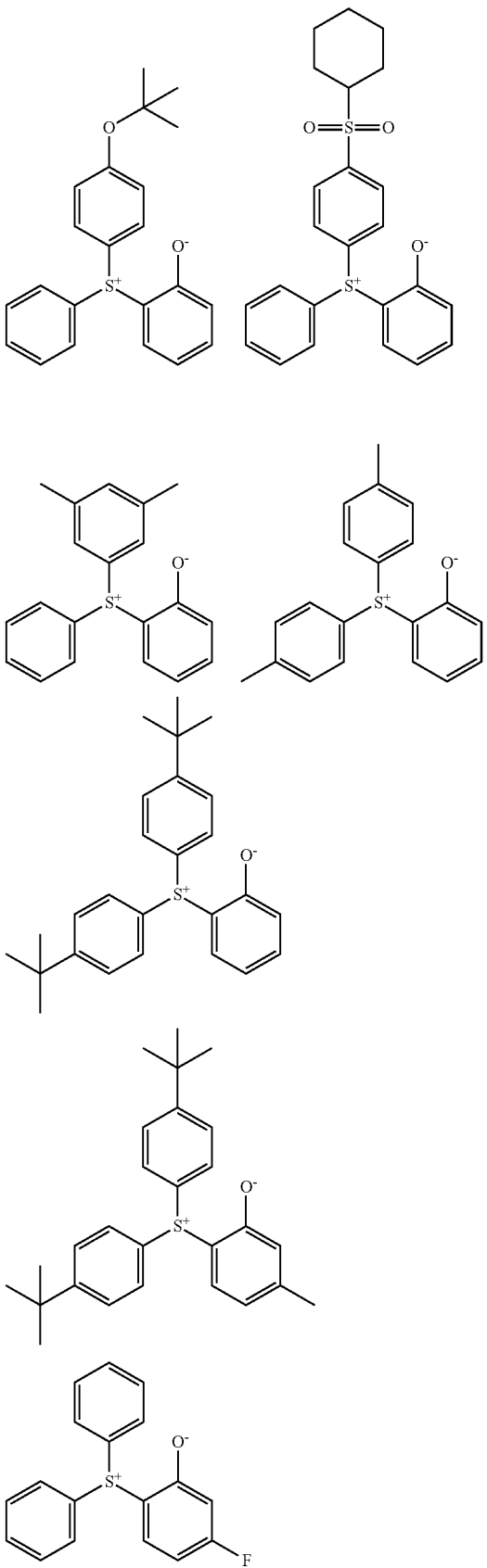

-continued

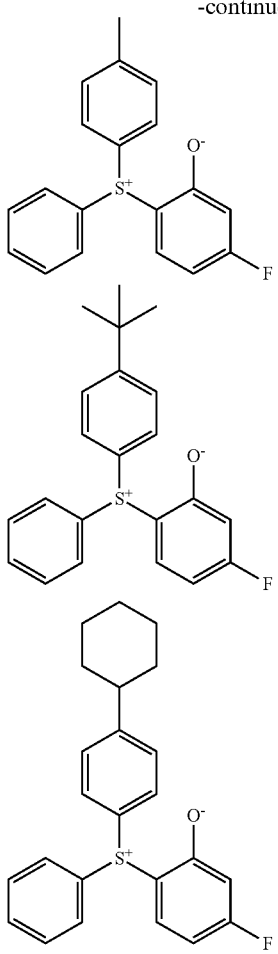

The content of the quencher is preferably 0.01 to 20 parts by weight, more preferably 0.05 to 15 parts by weight per 100 parts by weight of the base polymer. The quencher may be used alone or in admixture.

Generally, a crosslinker need not be added to the negative resist composition. When fine adjustment of resist performance is desired, a crosslinker may be added in an amount of 0.5 to 5 parts by weight per 100 parts by weight of the base polymer. The crosslinker may be selected from numerous well-known compounds as exemplified in Patent Documents 1 to 3.

Suitable crosslinkers used herein include alkoxymethylglycoluril compounds and alkoxymethylmelamine compounds, such as, for example, tetramethoxymethylglycoluril, 1,3-bismethoxymethyl-4,5-bismethoxyethylene urea, bismethoxymethyl urea, hexamethoxymethylmelamine, and hexaethoxymethylmelamine. The crosslinker may be used alone or in admixture.

In the resist composition, any of surfactants commonly used for improving coating characteristics may be added. The surfactant may be selected from numerous well-known compounds as exemplified in Patent Documents 1 to 5. Further, there may be added a fluorinated polymer as described in JP-A 2008-304590.

When added, an appropriate amount of the surfactant is at least 0.01 part and up to 2 parts, more preferably up to 1 part by weight per 100 parts by weight of the base polymer.

The resist composition may further contain an organic solvent. The organic solvent used herein is not particularly limited as long as the polymer, acid generator and other additives are soluble therein. Suitable organic solvents include ketones such as cyclohexanone and methyl n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Of the above organic solvents, it is recommended to use ethyl lactate, PGME, PGMEA, and mixtures thereof because the acid generator is most soluble therein.

An appropriate amount of the organic solvent used is 1,000 to 10,000 parts, more preferably 2,000 to 9,700 parts by weight per 100 parts by weight of the base polymer. From a resist composition solution which has been adjusted to such a concentration, a resist film of 10 to 300 nm thick having a high flatness can be formed in a consistent manner.

The negative resist composition may further comprise any suitable additives such as dissolution inhibitor.

Patterning Process

A still further embodiment of the invention is a resist pattern forming process comprising the steps of applying the resist composition defined above onto a substrate to form a resist film thereon, exposing the resist film patternwise to high-energy radiation, and developing the resist film in an alkaline developer to form a resist pattern.

Pattern formation using the negative resist composition of the invention may be performed by well-known lithography processes. In general, the resist composition is first applied onto a substrate such as a substrate for IC fabrication (e.g., silicon wafer having a surface layer of Si, $SiO_2$, SiN, SiON, TiN, WSi, BPSG, SOG, organic antireflective coating or the like) or a substrate for mask circuit fabrication (e.g., quartz substrate having a surface layer of Cr, CrO, CrON, $MoSi_2$, $SiO_2$ or the like, typically mask blank) by a suitable coating technique such as spin coating. The coating is prebaked on a hotplate at a temperature of 60 to 150° C. for 1 to 10 minutes, preferably at 80 to 140° C. for 1 to 5 minutes to form a resist film of 0.05 to 2.0 μm thick. As the substrate, especially photomask blank, a substrate having the outermost surface formed of a chromium-containing material is preferably used.

Then the resist film is exposed patternwise to high-energy radiation such as deep UV, excimer laser (KrF, ArF), EUV, or x-ray, through a mask having a desired pattern or directly by EB writing. The exposure dose is preferably 1 to 200 mJ/cm$^2$, more preferably 10 to 100 mJ/cm$^2$ in the case of deep UV, excimer laser, EUV or x-ray, or 1 to 300 μC/cm$^2$, more preferably 10 to 200 μC/cm$^2$ in the case of EB.

The exposure may be performed by conventional lithography whereas the immersion lithography of holding a liquid between the mask and the resist film may be employed if desired. When the immersion lithography is applied, a protective film which is insoluble in water may be formed on the resist film.

The resist film is then baked (PEB) on a hotplate at 60 to 150° C. for 1 to 10 minutes, preferably at 80 to 140° C. for 1 to 5 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

The negative resist composition has such etch resistance that it may withstand severe etching conditions and is effective when used under the conditions where a lower LER is required. The resist composition is effectively applicable to a substrate, specifically a substrate having a surface layer of material to which a resist film is less adherent and which is likely to invite pattern stripping or pattern collapse. The resist composition is advantageous in forming a pattern on a substrate having sputter deposited thereon metallic chromium or a chromium compound containing at least one light element selected from oxygen, nitrogen and carbon, especially a photomask blank.

EXAMPLES

Examples and Comparative Examples are given below by way of illustration and not by way of limitation. All parts are by weight (pbw); Mw is a weight average molecular weight as measured by GPC versus polystyrene standards. The copolymer compositional ratio is a molar ratio.

[1] Synthesis of Monomers

Example 1-1

Synthesis of Monomer 1

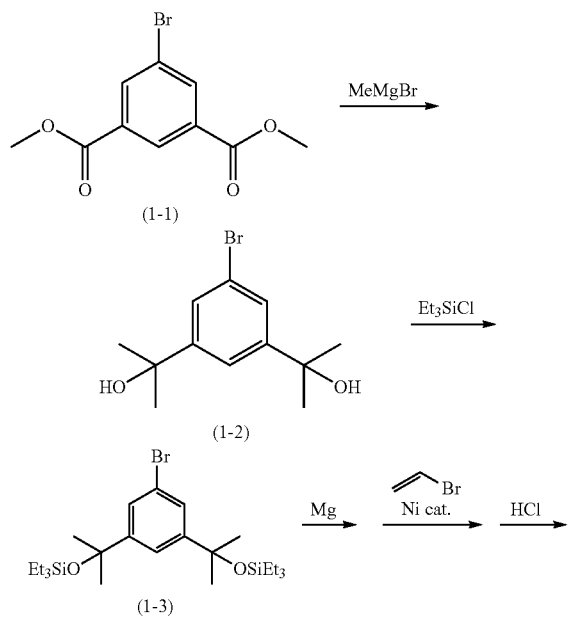

In a reactor, 440 g of dimethyl 3-bromoisophthalate (1-1) was dissolved in 3.5 kg of tetrahydrofuran (THF). Then 3.6 kg of a THF solution of 3 mol/L methylmagnesium chloride was added dropwise over 2 hours to the reactor in a water bath at 50° C. Under ice cooling, 5 kg of saturated ammonium chloride aqueous solution was added to the reaction solution. The organic layer was taken out and the water layer was extracted with 3 kg of ethyl acetate, followed by concentration under reduced pressure. Toluene was added to the concentrate, which was concentrated again. The precipitated solid was washed with hexane and dried under reduced pressure, obtaining 264 g of the desired compound, 3,5-bis(2-hydroxy-2-propyl)bromobenzene (1-2) as white solid (yield 60%).

Subsequently, 152 g of 3,5-bis(2-hydroxy-2-propyl)bromobenzene (1-2) and 94.6 g of imidazole were dissolved in 304 g of dimethylformamide (DMF). Under ice cooling, 168 g of triethylsilyl chloride was added dropwise to the solution, followed by stirring at room temperature for 24 hours. Under ice cooling, 152 g of water and 304 g of hexane were added. The organic layer was taken out, washed with water, and concentrated under reduced pressure, obtaining 3,5-bis(2-triethylsilyloxy-2-propyl)bromobenzene (1-3). Then a Grignard reagent was prepared by dissolving 3,5-bis(2-triethylsilyloxy-2-propyl)bromobenzene (1-3) in 390 g of THF, adding 18.7 g of magnesium to the solution, and heating the solution at 55° C. Under ice cooling, 1.4 g of dichloro[1,3-bis(diphenylphosphino)propane]nickel(II) was added to the Grignard reagent, after which 65.8 g of vinyl bromide was added dropwise. Under ice cooling, stirring was continued for 1 hour. To the reaction solution, 250 g of saturated ammonium chloride aqueous solution and 300 g of hexane were added. The organic layer was taken out, washed with water, and concentrated under reduced pressure. The resulting product was dissolved in 454 g of THF. Under ice cooling, 120 g of 35 wt % HCl aqueous solution was added to the THF solution, which was stirred for 6 hours. Thereafter, 900 g of ethyl acetate was added. The organic layer was taken out, washed with water, and concentrated under reduced pressure. The precipitated solid was dissolved in acetone and recrystallized from hexane. The resulting solid was dried under reduced pressure, obtaining 92.9 g of the target compound, 3,5-bis(2-hydroxy-2-propyl)styrene as white solid (yield 82%). It is designated Monomer 1.

Example 1-2

Synthesis of Monomer 2

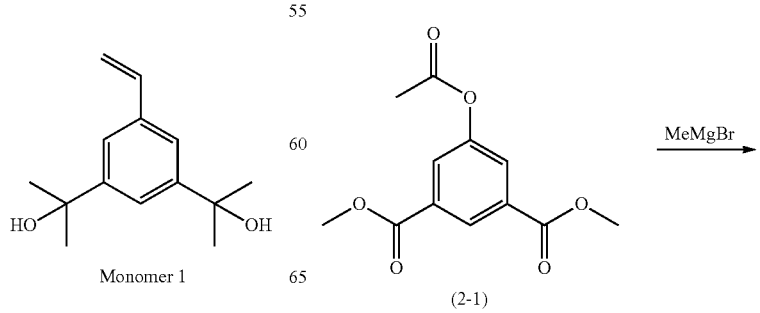

-continued

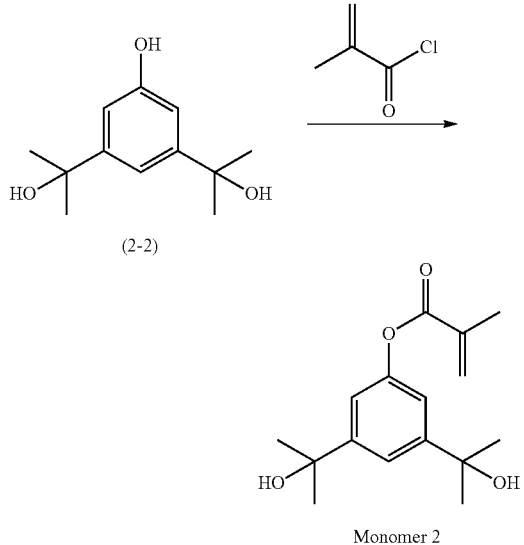

(2-2)

Monomer 2

In a reactor, 270 g of dimethyl 3-acetoxyisophthalate (2-1) was dissolved in 3.5 kg of THF. Then 3.6 kg of a THF solution of 3 mol/L methylmagnesium chloride was added dropwise over 2 hours to the reactor in a water bath at 50° C. Under ice cooling, 5 kg of saturated ammonium chloride aqueous solution was added to the reaction solution. The organic layer was taken out and the water layer was extracted with 3 kg of ethyl acetate, followed by concentration under reduced pressure. Toluene was added to the concentrate, which was concentrated again. The precipitated solid was washed with hexane and dried under reduced pressure, obtaining 187 g of the desired compound, 3,5-bis(2-hydroxy-2-propyl)phenol (2-2) as white solid (yield 73%).

Subsequently, 515 g of 3,5-bis(2-hydroxy-2-propyl)phenol (2-2) was mixed with 417 g of triethylamine and 1,500 g of THF. 282 g of methacryloyl chloride was added dropwise to the mixture over 1 hour, followed by stirring at room temperature for 3 hours. Under ice cooling, 750 g of 10 wt % HCl aqueous solution and 1,500 g of ethyl acetate were added to the reaction solution. The organic layer was taken out, washed with water, and concentrated under reduced pressure. The precipitated solid was dissolved in acetone and recrystallized from hexane. The solid was dried under reduced pressure, obtaining 486 g of the desired compound, 3,5-bis(2-hydroxy-2-propyl)phenyl methacrylate as white solid (yield 80%). It is designated Monomer 2.

[2] Synthesis of Polymers

Example 2-1

Synthesis of Polymer 1

A 500-mL dropping funnel under nitrogen blanket was charged with 62.5 g of a 50 wt % PGMEA solution of 4-hydroxystyrene, 8.51 g of acenaphthylene, 49.3 g of 3,5-bis(2-hydroxy-2-propyl)styrene, 11.0 g of triphenylsulfonium 1,1,3,3,3-pentafluoro-2-methacryloyloxypropane-1-sulfonate, 10.3 g of dimethyl2,2'-azobis(2-methylpropionate) (V601 by Wako Pure Chemical Industries, Ltd.), and 156 g of γ-butyrolactone and 24 g of PGMEA as solvent to form a solution A. A 1000-mL flask under nitrogen blanket was charged with 78 g of γ-butyrolactone, which was heated at 80° C. While the temperature was maintained, solution A was added dropwise to the flask over 4 hours. At the end of dropwise addition, the solution was continuously stirred for 18 hours while the temperature of 80° C. was maintained during polymerization. The polymerization solution was cooled to room temperature and added dropwise to 3,000 g of diisopropyl ether, whereupon a solid precipitated. The diisopropyl ether was removed by decantation, and the precipitated solid was dissolved in 200 g of acetone. The acetone solution was added dropwise to 3,000 g of diisopropyl ether whereupon a solid precipitated. The solid or copolymer was collected by filtration and dissolved in 200 g of acetone again. The acetone solution was added dropwise to 3,000 g of water whereupon a solid precipitated. The solid was collected by filtration and dried at 40° C. for 40 hours, obtaining 72 g of the desired polymer (Polymer 1) as white solid. Polymer 1 was analyzed by $^{13}$C-NMR and $^{1}$-NMR spectroscopy to determine a compositional ratio of recurring units and by GPC to determine Mw and Mw/Mn, with the results shown below.

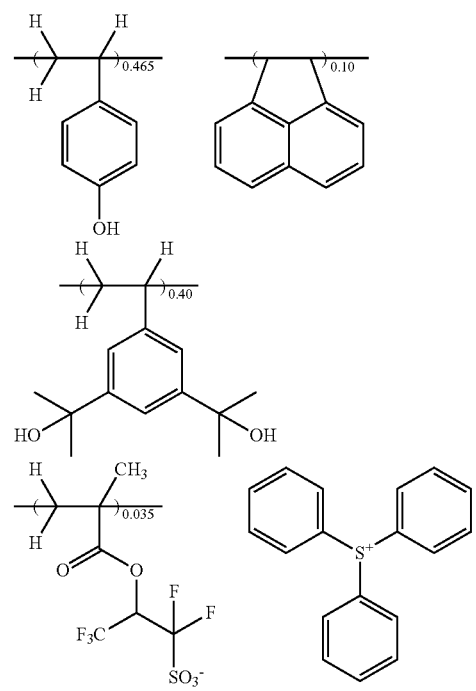

Mw = 14,600
Mw/Mn = 1.62

Examples 2-2 to 2-27 and Comparative Examples 1-1 to 1-4

Synthesis of Polymers 2 to 27 and Comparative Polymers 1 to 4

Polymers 2 to 27 and Comparative Polymers 1 to 4 shown in Tables 1 and 3 were synthesized by the same procedure as in Example 2-1 except that the type and amount of monomers were changed.

Example 2-28

Synthesis of Polymer 28

A 200-mL dropping funnel under nitrogen blanket was charged with 26.0 g of 4-acetoxystyrene, 9.31 g of acenaphthylene, 64.71 g of 3,5-bis(2-hydroxy-2-propyl)styrene, 9.8 g of dimethyl 2,2'-azobis(2-methylpropionate) (V601 by Wako Pure Chemical Industries, Ltd.), and 56 g of methyl ethyl ketone (MEK) as solvent to form a solution B. A 500-mL flask under nitrogen blanket was charged with 38 g of MEK, which was heated at 80° C. While the temperature was maintained, solution B was added dropwise to the flask over 4 hours. At the end of dropwise addition, the solution was continuously stirred for 18 hours while the temperature of 80° C. was maintained during polymerization. The polymerization solution was cooled to room temperature and added dropwise to 1,400 g of hexane, whereupon a solid precipitated. The solid was collected by filtration and washed twice with 280 g of hexane. In a 1-L flask under nitrogen blanket, the solid was dissolved in a mixture of 180 g THF and 60 g methanol. 29.4 g of ethanol amine was added to the solution, which was stirred at 60° C. for 3 hours. The reaction solution was concentrated under reduced pressure, and the concentrate was dissolved in a mixture of 300 g ethyl acetate and 90 g water. The resulting solution was transferred to a separatory funnel where 29 g of acetic acid was added, followed by separatory operation. After the lower layer was distilled off, 90 g of water and 39 g of pyridine were added to the organic layer, followed by separatory operation. After the lower layer was distilled off, 90 g of water was added to the organic layer, followed by water washing and separatory operation. The water washing and separatory operation was repeated 5 times in total. The organic layer after the separatory operation was concentrated and dissolved in 150 g of acetone again. The acetone solution was added dropwise to 3,000 g of water whereupon a crystal precipitated. The crystal precipitate was collected by filtration, washed with water, and suction filtered for 2 hours. The filter cake was dissolved in 150 g of acetone. The acetone solution was added dropwise to 3,000 g of water whereupon a crystal precipitated. The crystal precipitate was collected by filtration, washed with water, and dried, obtaining 58.0 g of the desired polymer (Polymer 28) as white solid. Polymer 28 was analyzed by $^{13}$C-NMR and $^1$H-NMR spectroscopy to determine a compositional ratio of recurring units and by GPC to determine Mw and Mw/Mn, with the results shown below.

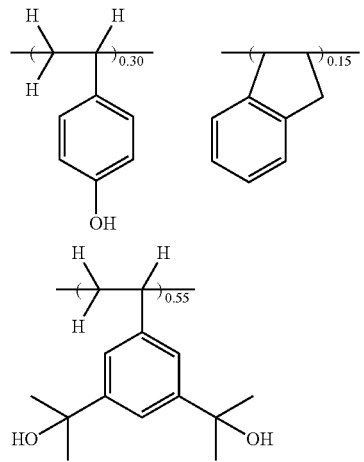

Mw = 3,900
Mw/Mn = 1.68

Example 2-34

Synthesis of Polymer 34

A 200-mL dropping funnel under nitrogen blanket was charged with 13.2 g of hydroquinone monomethacrylate, 5.51 g of acenaphthylene, 31.4 g of 3,5-bis(2-hydroxy-2-propyl)styrene, 4.85 g of dimethyl 2,2'-azobis(2-methylpropionate) (V601 by Wako Pure Chemical Industries, Ltd.), and 56 g of MEK as solvent to form a solution C. A 500-mL flask under nitrogen blanket was charged with 38 g of MEK, which was heated at 80° C. While the temperature was maintained, solution C was added dropwise to the flask over 4 hours. At the end of dropwise addition, the solution was continuously stirred for 18 hours while the temperature of 80° C. was maintained during polymerization. The polymerization solution was cooled to room temperature and added dropwise to 1,000 g of hexane, whereupon a solid precipitated. The solid precipitate was collected by filtration and washed twice with 200 g of hexane. The solid was collected by filtration and dried, obtaining 45.0 g of the desired polymer (Polymer 34) as white solid. Polymer 34 was analyzed by $^{13}$C-NMR and $^1$H-NMR spectroscopy to determine a compositional ratio of recurring units and by GPC to determine Mw and Mw/Mn, with the results shown below.

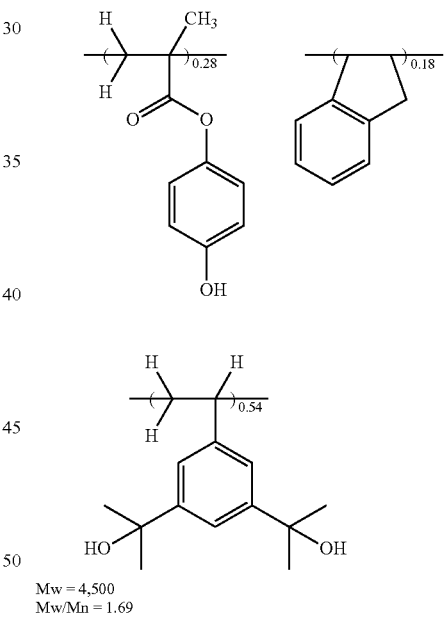

Mw = 4,500
Mw/Mn = 1.69

Examples 2-29 to 2-33, 2-35 to 2-47 and Comparative Examples 1-5 to 1-8

Synthesis of Polymers 29 to 33, 35 to 47 and Comparative Polymers 5 to 8

Polymers 29 to 33, 35 to 47 and Comparative Polymers 5 to 8 shown in Tables 2 and 3 were synthesized by the same procedure as in Example 2-28 in the case of polymers containing units A-1, or as in Example 2-34 in the case of polymers containing units A-2, except that the type and amount of monomers were changed.

TABLE 1

|  |  |  | Unit 1 | Compositional ratio (mol %) | Unit 2 | Compositional ratio (mol %) | Unit 3 | Compositional ratio (mol %) | Unit 4 | Compositional ratio (mol %) | Mw | Mw/Mn |
|---|---|---|---|---|---|---|---|---|---|---|---|---|
| Example | 2-1 | Polymer 1 | A-1 | 46.5 | B-1 | 10.0 | C-1 | 40.0 | P-1 | 3.5 | 14,600 | 1.62 |
|  | 2-2 | Polymer 2 | A-1 | 50.0 | B-1 | 10.0 | C-2 | 36.0 | P-1 | 4.0 | 13,500 | 1.61 |
|  | 2-3 | Polymer 3 | A-1 | 51.5 | B-2 | 10.0 | C-1 | 35.0 | P-1 | 3.5 | 14,200 | 1.63 |
|  | 2-4 | Polymer 4 | A-1 | 55.5 | B-2 | 10.0 | C-2 | 31.0 | P-1 | 3.5 | 14,100 | 1.62 |
|  | 2-5 | Polymer 5 | A-1 | 46.5 | B-3 | 12.0 | C-1 | 38.0 | P-1 | 3.5 | 15,100 | 1.62 |
|  | 2-6 | Polymer 6 | A-1 | 52.5 | B-3 | 12.0 | C-2 | 32.0 | P-1 | 3.5 | 14,800 | 1.62 |
|  | 2-7 | Polymer 7 | A-2 | 50.0 | B-1 | 10.0 | C-1 | 35.0 | P-1 | 5.0 | 15,700 | 1.62 |
|  | 2-8 | Polymer 8 | A-2 | 55.5 | B-1 | 10.0 | C-2 | 31.0 | P-1 | 3.5 | 13,400 | 1.61 |
|  | 2-9 | Polymer 9 | A-2 | 56.0 | B-2 | 10.0 | C-1 | 30.0 | P-1 | 4.0 | 13,900 | 1.63 |
|  | 2-10 | Polymer 10 | A-2 | 59.0 | B-2 | 10.0 | C-2 | 26.0 | P-1 | 5.0 | 13,800 | 1.55 |
|  | 2-11 | Polymer 11 | A-2 | 51.5 | B-3 | 12.0 | C-1 | 33.0 | P-1 | 3.5 | 13,700 | 1.64 |
|  | 2-12 | Polymer 12 | A-2 | 57.5 | B-3 | 12.0 | C-2 | 27.0 | P-1 | 3.5 | 14,100 | 1.62 |
|  | 2-13 | Polymer 13 | A-1 | 53.0 | B-2 | 11.0 | C-1 | 31.0 | P-2 | 5.0 | 14,200 | 1.60 |
|  | 2-14 | Polymer 14 | A-1 | 56.0 | B-2 | 10.0 | C-1 | 30.0 | P-3 | 4.0 | 15,000 | 1.60 |
|  | 2-15 | Polymer 15 | A-1 | 55.5 | B-2 | 12.0 | C-2 | 29.0 | P-4 | 3.5 | 14,200 | 1.61 |
|  | 2-16 | Polymer 16 | A-2 | 58.0 | B-2 | 12.0 | C-1 | 25.0 | P-5 | 5.0 | 14,700 | 1.67 |
|  | 2-17 | Polymer 17 | A-1 | 57.0 | B-2 | 11.0 | C-2 | 28.0 | P-6 | 4.0 | 14,400 | 1.65 |
|  | 2-18 | Polymer 18 | A-1 | 65.5 | B-3 | 10.0 | C-3 | 21.0 | P-1 | 3.5 | 13,900 | 1.63 |
|  | 2-19 | Polymer 19 | A-1 | 66.5 | B-1 | 11.0 | C-4 | 19.0 | P-1 | 3.5 | 14,700 | 1.62 |
|  | 2-20 | Polymer 20 | A-2 | 68.0 | B-3 | 11.0 | C-5 | 17.0 | P-2 | 4.0 | 14,600 | 1.61 |
|  | 2-21 | Polymer 21 | A-1 | 69.5 | B-2 | 11.0 | C-6 | 16.0 | P-4 | 3.5 | 13,900 | 1.61 |
|  | 2-22 | Polymer 22 | A-2 | 62.5 | B-1 | 11.0 | C-3 | 23.0 | P-1 | 3.5 | 9,700 | 1.58 |
|  | 2-23 | Polymer 23 | A-1 | 65.0 | B-2 | 10.0 | C-4 | 20.0 | P-3 | 5.0 | 9,800 | 1.57 |
|  | 2-24 | Polymer 24 | A-2 | 67.5 | B-1 | 10.0 | C-5 | 19.0 | P-1 | 3.5 | 10,200 | 1.58 |
|  | 2-25 | Polymer 25 | A-1 | 67.0 | B-3 | 10.0 | C-6 | 18.0 | P-1 | 5.0 | 11,300 | 1.56 |
|  | 2-26 | Polymer 26 | A-1 | 58.5 | B-2 | 12.0 | C-3 | 26.0 | P-2 | 3.5 | 14,200 | 1.57 |
|  | 2-27 | Polymer 27 | A-2 | 61.0 | B-2 | 11.0 | C-4 | 24.0 | P-1 | 4.0 | 14,200 | 1.59 |

TABLE 2

|  |  |  | Unit 1 | Compositional ratio (mol %) | Unit 2 | Compositional ratio (mol %) | Unit 3 | Compositional ratio (mol %) | Unit 4 | Compositional ratio (mol %) | Mw | Mw/Mn |
|---|---|---|---|---|---|---|---|---|---|---|---|---|
| Example | 2-28 | Polymer 28 | A-1 | 30.0 | B-1 | 15.0 | C-1 | 55.0 | — | — | 3,900 | 1.68 |
|  | 2-29 | Polymer 29 | A-1 | 46.0 | B-1 | 14.0 | C-2 | 40.0 | — | — | 4,200 | 1.67 |
|  | 2-30 | Polymer 30 | A-1 | 32.0 | B-2 | 10.0 | C-1 | 58.0 | — | — | 4,300 | 1.71 |
|  | 2-31 | Polymer 31 | A-1 | 47.0 | B-2 | 10.0 | C-2 | 43.0 | — | — | 4,200 | 1.65 |
|  | 2-32 | Polymer 32 | A-1 | 31.0 | B-3 | 19.0 | C-1 | 50.0 | — | — | 4,100 | 1.66 |
|  | 2-33 | Polymer 33 | A-1 | 47.0 | B-3 | 20.0 | C-2 | 33.0 | — | — | 4,200 | 1.68 |
|  | 2-34 | Polymer 34 | A-2 | 28.0 | B-1 | 18.0 | C-1 | 54.0 | — | — | 4,500 | 1.69 |
|  | 2-35 | Polymer 35 | A-2 | 44.0 | B-1 | 17.0 | C-2 | 39.0 | — | — | 4,400 | 1.67 |
|  | 2-36 | Polymer 36 | A-2 | 27.0 | B-2 | 12.0 | C-1 | 61.0 | — | — | 4,300 | 1.68 |
|  | 2-37 | Polymer 37 | A-2 | 46.0 | B-2 | 12.0 | C-2 | 42.0 | — | — | 4,500 | 1.69 |
|  | 2-38 | Polymer 38 | A-2 | 29.0 | B-3 | 21.0 | C-1 | 50.0 | — | — | 4,400 | 1.67 |
|  | 2-39 | Polymer 39 | A-2 | 45.0 | B-3 | 21.0 | C-2 | 34.0 | — | — | 4,200 | 1.68 |
|  | 2-40 | Polymer 40 | A-1 | 38.0 | B-3 | 12.0 | C-3 | 50.0 | — | — | 4,300 | 1.65 |
|  | 2-41 | Polymer 41 | A-1 | 43.0 | B-1 | 13.0 | C-4 | 44.0 | — | — | 4,100 | 1.66 |
|  | 2-42 | Polymer 42 | A-2 | 58.0 | B-3 | 11.0 | C-5 | 31.0 | — | — | 4,200 | 1.67 |
|  | 2-43 | Polymer 43 | A-1 | 60.0 | B-2 | 10.0 | C-6 | 30.0 | — | — | 4,300 | 1.68 |
|  | 2-44 | Polymer 44 | A-1 | 38.0 | B-3 | 12.0 | C-3 | 50.0 | — | — | 4,300 | 1.69 |
|  | 2-45 | Polymer 45 | A-1 | 46.0 | B-1 | 11.0 | C-4 | 43.0 | — | — | 4,400 | 1.68 |
|  | 2-46 | Polymer 46 | A-1 | 62.0 | B-3 | 10.0 | C-5 | 28.0 | — | — | 4,500 | 1.68 |
|  | 2-47 | Polymer 47 | A-1 | 62.0 | B-3 | 12.0 | C-6 | 26.0 | — | — | 4,000 | 1.69 |

TABLE 3

| | | Unit 1 | Compositional ratio (mol %) | Unit 2 | Compositional ratio (mol %) | Unit 3 | Compositional ratio (mol %) | Unit 4 | Compositional ratio (mol %) | Mw | Mw/Mn |
|---|---|---|---|---|---|---|---|---|---|---|---|
| Comparative Example | 1-1 Comparative Polymer 1 | A-1 | 69.5 | B-1 | 6.0 | C-7 | 21.0 | P-1 | 3.5 | 13,500 | 1.61 |
| | 1-2 Comparative Polymer 2 | A-1 | 69.5 | B-1 | 6.0 | C-7 | 21.0 | P-1 | 3.5 | 14,200 | 1.61 |
| | 1-3 Comparative Polymer 3 | A-1 | 72.5 | B-2 | 6.0 | C-8 | 18.0 | P-1 | 3.5 | 14,100 | 1.61 |
| | 1-4 Comparative Polymer 4 | A-1 | 72.5 | B-2 | 6.0 | C-8 | 18.0 | P-1 | 3.5 | 13,800 | 1.62 |
| | 1-5 Comparative Polymer 5 | A-1 | 72.0 | B-1 | 9.0 | C-7 | 19.0 | — | — | 3,900 | 1.65 |
| | 1-6 Comparative Polymer 6 | A-2 | 56.0 | B-1 | 14.0 | C-7 | 30.0 | — | — | 4,100 | 1.67 |
| | 1-7 Comparative Polymer 7 | A-1 | 72.0 | B-2 | 10.0 | C-8 | 18.0 | — | — | 4,000 | 1.68 |
| | 1-8 Comparative Polymer 8 | A-1 | 76.0 | B-2 | 8.0 | C-8 | 16.0 | — | — | 4,100 | 1.67 |

Tables 4 to 7 show the structure of recurring units in Tables 1 to 3.

TABLE 4

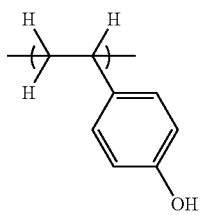

A-1

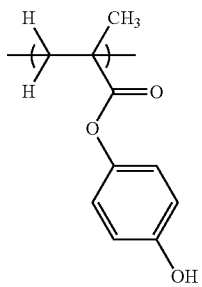

A-2

TABLE 5

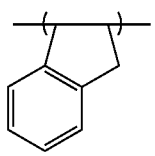

B-1

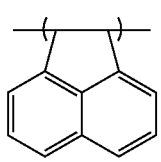

B-2

TABLE 5-continued

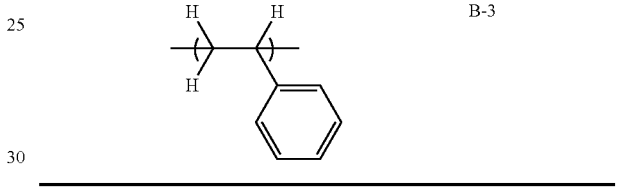

B-3

TABLE 6

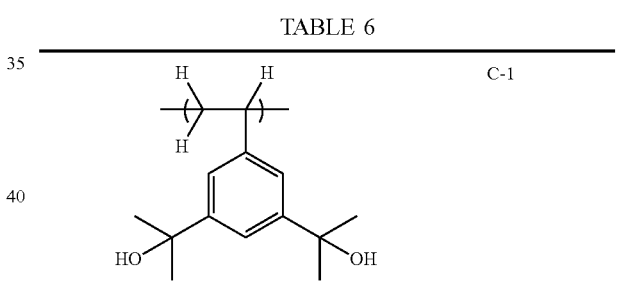

C-1

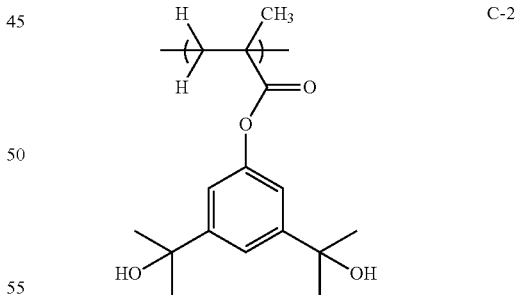

C-2

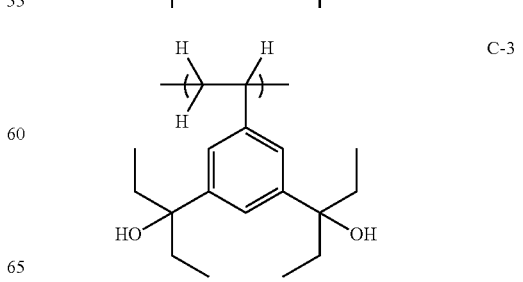

C-3

TABLE 6-continued
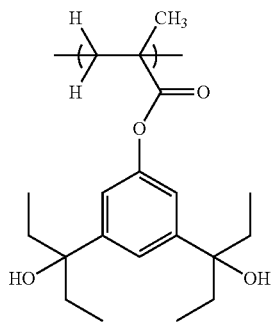  C-4
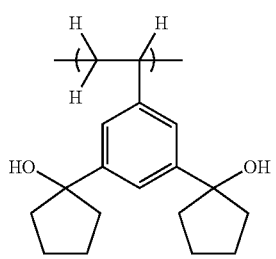  C-5
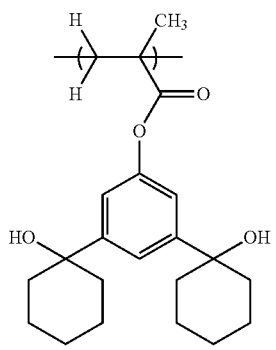  C-6
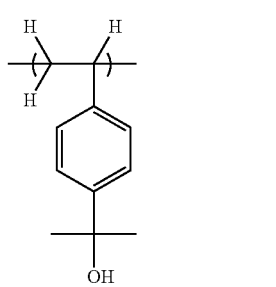  C-7
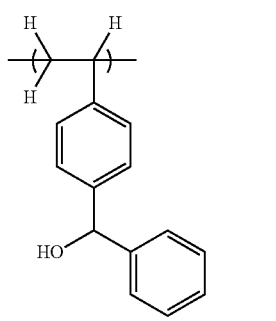  C-8
TABLE 7
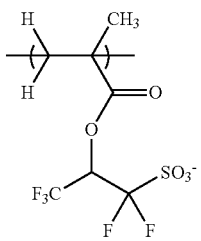  P-1
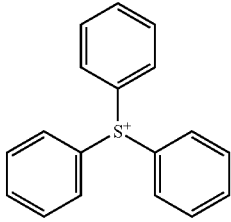 [SMILES: c1ccc([S+](c2ccccc2)c2ccccc2)cc1]
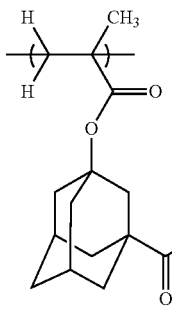  P-2
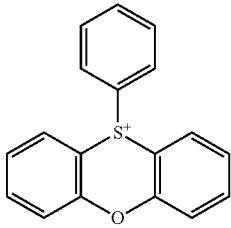 [SMILES: c1ccc([S+]2c3ccccc3Oc3ccccc32)cc1]
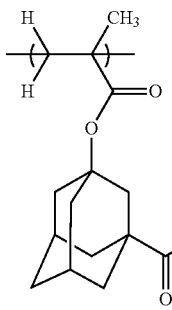  P-3
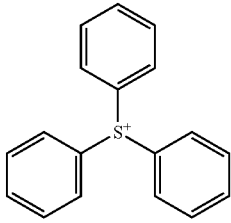 [SMILES: c1ccc([S+](c2ccccc2)c2ccccc2)cc1]

TABLE 7-continued

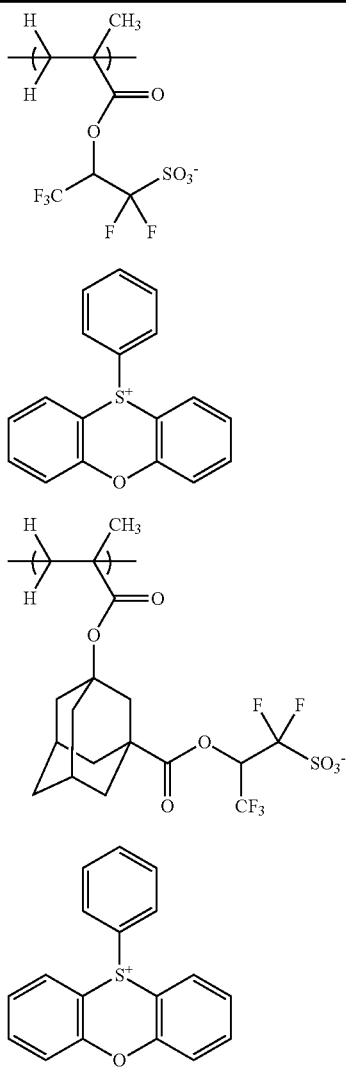

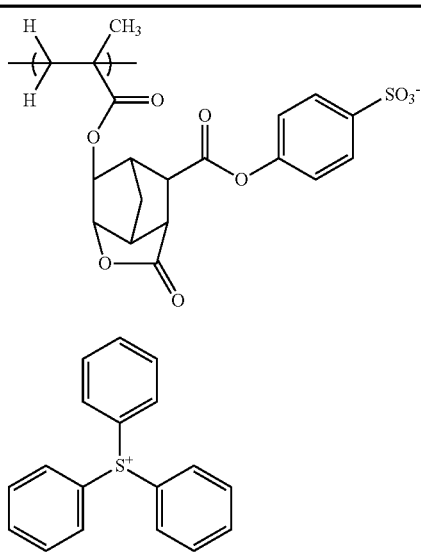

[3] Preparation of Negative Resist Compositions

Examples 3-1 to 3-75 and Comparative Examples 2-1 to 2-10

A negative resist composition in solution form was prepared by dissolving a polymer (Polymers 1 to 47 or Comparative Polymers 1 to 8), an acid generator (PAG-1 to PAG-4), a quencher (Q-1 to Q-4), and optionally a fluorinated polymer (FP-1) in an organic solvent in accordance with the recipe shown in Tables 8 to 11, and filtering through a Teflon® filter with a pore size of 0.2 μm. It is noted that each resist composition contained 0.075 part by weight of a surfactant PF-636 (Omnova Solutions) per 100 parts by weight of solids.

In Tables 8 to 11, PGMEA stands for propylene glycol monomethyl ether acetate, EL for ethyl lactate, and PGME for propylene glycol monomethyl ether.

TABLE 8

|  | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|
| Example 3-1 | R-1 | Polymer 1 (80) | — | Q-1 (4.0) | — | PGMEA (1,080) | EL (1,080) | PGME (1,440) |
| 3-2 | R-2 | Polymer 2 (80) | — | Q-1 (3.8) | — | PGMEA (1,080) | EL (1,080) | PGME (1,440) |
| 3-3 | R-3 | Polymer 3 (80) | — | Q-1 (4.1) | — | PGMEA (1,080) | EL (1,080) | PGME (1,440) |
| 3-4 | R-4 | Polymer 4 (80) | — | Q-1 (3.9) | — | PGMEA (1,080) | EL (1,080) | PGME (1,440) |
| 3-5 | R-5 | Polymer 5 (80) | — | Q-1 (4.0) | — | PGMEA (1,080) | EL (1,080) | PGME (1,440) |
| 3-6 | R-6 | Polymer 6 (80) | — | Q-1 (4.0) | — | PGMEA (1,080) | EL (1,080) | PGME (1,440) |
| 3-7 | R-7 | Polymer 7 (80) | — | Q-1 (4.2) | — | PGMEA (1,080) | EL (1,080) | PGME (1,440) |
| 3-8 | R-8 | Polymer 8 (80) | — | Q-1 (3.8) | — | PGMEA (1,080) | EL (1,080) | PGME (1,440) |
| 3-9 | R-9 | Polymer 9 (80) | — | Q-1 (4.3) | — | PGMEA (1,080) | EL (1,080) | PGME (1,440) |
| 3-10 | R-10 | Polymer 10 (80) | — | Q-1 (3.6) | — | PGMEA (1,080) | EL (1,080) | PGME (1,440) |

TABLE 8-continued

| | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|
| 3-11 | R-11 | Polymer 11 (80) | — | Q-1 (3.8) | — | PGMEA (1,080) | EL (1,080) | PGME (1,440) |
| 3-12 | R-12 | Polymer 12 (80) | — | Q-1 (3.9) | — | PGMEA (1,080) | EL (1,080) | PGME (1,440) |
| 3-13 | R-13 | Polymer 13 (80) | — | Q-1 (4.1) | — | PGMEA (1,080) | EL (1,080) | PGME (1,440) |
| 3-14 | R-14 | Polymer 14 (80) | — | Q-1 (4.0) | — | PGMEA (1,080) | EL (1,080) | PGME (1,440) |
| 3-15 | R-15 | Polymer 15 (80) | — | Q-1 (4.0) | — | PGMEA (1,080) | EL (1,080) | PGME (1,440) |
| 3-16 | R-16 | Polymer 16 (80) | — | Q-1 (4.2) | — | PGMEA (1,080) | EL (1,080) | PGME (1,440) |
| 3-17 | R-17 | Polymer 17 (80) | — | Q-1 (3.8) | — | PGMEA (1,080) | EL (1,080) | PGME (1,440) |
| 3-18 | R-18 | Polymer 18 (80) | — | Q-1 (3.9) | — | PGMEA (1,080) | EL (1,080) | PGME (1,440) |
| 3-19 | R-19 | Polymer 19 (80) | — | Q-1 (4.0) | — | PGMEA (1,080) | EL (1,080) | PGME (1,440) |
| 3-20 | R-20 | Polymer 20 (80) | — | Q-1 (4.1) | — | PGMEA (1,080) | EL (1,080) | PGME (1,440) |
| 3-21 | R-21 | Polymer 21 (80) | — | Q-1 (3.9) | — | PGMEA (1,080) | EL (1,080) | PGME (1,440) |
| 3-22 | R-22 | Polymer 22 (80) | — | Q-1 (4.2) | — | PGMEA (1,080) | EL (1,080) | PGME (1,440) |
| 3-23 | R-23 | Polymer 23 (80) | — | Q-1 (4.1) | — | PGMEA (1,080) | EL (1,080) | PGME (1,440) |
| 3-24 | R-24 | Polymer 24 (80) | — | Q-1 (3.9) | — | PGMEA (1,080) | EL (1,080) | PGME (1,440) |
| 3-25 | R-25 | Polymer 25 (80) | — | Q-1 (4.0) | — | PGMEA (1,080) | EL (1,080) | PGME (1,440) |

TABLE 9

| | | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|---|
| Example | 3-26 | R-26 | Polymer 26 (80) | — | Q-1 (3.9) | — | PGMEA (1,080) | EL (1,080) | PGME (1,440) |
| | 3-27 | R-27 | Polymer 27 (80) | — | Q-1 (3.9) | — | PGMEA (1,080) | EL (1,080) | PGME (1,440) |
| | 3-28 | R-28 | Polymer 28 (80) | PAG-1 (8.0) | Q-1 (4.2) | — | PGMEA (1,080) | EL (1,080) | PGME (1,440) |
| | 3-29 | R-29 | Polymer 29 (80) | PAG-1 (8.0) | Q-1 (3.8) | — | PGMEA (1,080) | EL (1,080) | PGME (1,440) |
| | 3-30 | R-30 | Polymer 30 (80) | PAG-1 (8.0) | Q-1 (3.9) | — | PGMEA (1,080) | EL (1,080) | PGME (1,440) |
| | 3-31 | R-31 | Polymer 31 (80) | PAG-1 (8.0) | Q-1 (3.9) | — | PGMEA (1,080) | EL (1,080) | PGME (1,440) |
| | 3-32 | R-32 | Polymer 32 (80) | PAG-1 (8.0) | Q-1 (4.1) | — | PGMEA (1,080) | EL (1,080) | PGME (1,440) |
| | 3-33 | R-33 | Polymer 33 (80) | PAG-1 (8.0) | Q-1 (4.2) | — | PGMEA (1,080) | EL (1,080) | PGME (1,440) |
| | 3-34 | R-34 | Polymer 34 (80) | PAG-1 (8.0) | Q-1 (4.0) | — | PGMEA (1,080) | EL (1,080) | PGME (1,440) |
| | 3-35 | R-35 | Polymer 35 (80) | PAG-1 (8.0) | Q-1 (3.9) | — | PGMEA (1,080) | EL (1,080) | PGME (1,440) |
| | 3-36 | R-36 | Polymer 36 (80) | PAG-1 (8.0) | Q-1 (3.9) | — | PGMEA (1,080) | EL (1,080) | PGME (1,440) |
| | 3-37 | R-37 | Polymer 37 (80) | PAG-1 (8.0) | Q-1 (3.8) | — | PGMEA (1,080) | EL (1,080) | PGME (1,440) |
| | 3-38 | R-38 | Polymer 38 (80) | PAG-1 (8.0) | Q-1 (4.1) | — | PGMEA (1,080) | EL (1,080) | PGME (1,440) |
| | 3-39 | R-39 | Polymer 39 (80) | PAG-1 (8.0) | Q-1 (3.9) | — | PGMEA (1,080) | EL (1,080) | PGME (1,440) |
| | 3-40 | R-40 | Polymer 40 (80) | PAG-1 (8.0) | Q-1 (4.0) | — | PGMEA (1,080) | EL (1,080) | PGME (1,440) |
| | 3-41 | R-41 | Polymer 41 (80) | PAG-1 (8.0) | Q-1 (3.9) | — | PGMEA (1,080) | EL (1,080) | PGME (1,440) |
| | 3-42 | R-42 | Polymer 42 (80) | PAG-1 (8.0) | Q-1 (4.2) | — | PGMEA (1,080) | EL (1,080) | PGME (1,440) |
| | 3-43 | R-43 | Polymer 43 (80) | PAG-1 (8.0) | Q-1 (4.3) | — | PGMEA (1,080) | EL (1,080) | PGME (1,440) |

TABLE 9-continued

| | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|
| 3-44 | R-44 | Polymer 44 (80) | PAG-1 (8.0) | Q-1 (4.1) | — | PGMEA (1,080) | EL (1,080) | PGME (1,440) |
| 3-45 | R-45 | Polymer 45 (80) | PAG-1 (8.0) | Q-1 (4.4) | — | PGMEA (1,080) | EL (1,080) | PGME (1,440) |
| 3-46 | R-46 | Polymer 46 (80) | PAG-1 (8.0) | Q-1 (4.3) | — | PGMEA (1,080) | EL (1,080) | PGME (1,440) |
| 3-47 | R-47 | Polymer 47 (80) | PAG-1 (8.0) | Q-1 (4.0) | — | PGMEA (1,080) | EL (1,080) | PGME (1,440) |
| 3-48 | R-48 | Polymer 1 (80) | PAG-1 (8.0) | Q-1 (4.1) | — | PGMEA (1,080) | EL (1,080) | PGME (1,440) |
| 3-49 | R-49 | Polymer 1 (80) | PAG-1 (8.0) | Q-1 (3.2) | — | PGMEA (1,080) | EL (1,080) | PGME (1,440) |
| 3-50 | R-50 | Polymer 1 (80) | PAG-1 (8.0) | Q-1 (2.9) | — | PGMEA (1,080) | EL (1,080) | PGME (1,440) |

TABLE 10

| | | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|---|
| Example | 3-51 | R-51 | Polymer 1 (80) | PAG-2 (8.0) | Q-1 (4.0) | — | PGMEA (1,080) | EL (1,080) | PGME (1,440) |
| | 3-52 | R-52 | Polymer 1 (80) | PAG-3 (8.0) | Q-1 (4.0) | — | PGMEA (1,080) | EL (1,080) | PGME (1,440) |
| | 3-53 | R-53 | Polymer 1 (80) | PAG-4 (8.0) | Q-1 (4.0) | — | PGMEA (1,080) | EL (1,080) | PGME (1,440) |
| | 3-54 | R-54 | Polymer 1 (40) Polymer 28 (40) | — | Q-1 (4.0) | — | PGMEA (1,080) | EL (1,080) | PGME (1,440) |
| | 3-55 | R-55 | Polymer 1 (40) Polymer 28 (40) | PAG-1 (5.0) | Q-1 (4.6) | — | PGMEA (1,080) | EL (1,080) | PGME (1,440) |
| | 3-56 | R-56 | Polymer 2 (40) Polymer 29 (40) | PAG-1 (5.0) | Q-2 (4.4) | — | PGMEA (1,080) | EL (1,080) | PGME (1,440) |
| | 3-57 | R-57 | Polymer 2 (40) Polymer 29 (40) | PAG-1 (5.0) | Q-3 (3.5) | — | PGMEA (1,080) | EL (1,080) | PGME (1,440) |
| | 3-58 | R-58 | Polymer 2 (40) Polymer 29 (40) | PAG-1 (5.0) | Q-4 (3.1) | — | PGMEA (1,080) | EL (1,080) | PGME (1,440) |
| | 3-59 | R-59 | Polymer 1 (40) Polymer 28 (40) | PAG-2 (5.0) | Q-1 (4.1) | — | PGMEA (1,080) | EL (1,080) | PGME (1,440) |
| | 3-60 | R-60 | Polymer 1 (40) Polymer 28 (40) | PAG-3 (5.0) | Q-1 (4.5) | — | PGMEA (1,080) | EL (1,080) | PGME (1,440) |
| | 3-61 | R-61 | Polymer 1 (40) Polymer 28 (40) | PAG-4 (5.0) | Q-1 (4.3) | — | PGMEA (1,080) | EL (1,080) | PGME (1,440) |
| | 3-62 | R-62 | Polymer 2 (40) Polymer 29 (40) | PAG-1 (5.0) | Q-1 (4.7) | — | PGMEA (1,080) | EL (1,080) | PGME (1,440) |
| | 3-63 | R-63 | Polymer 3 (40) Polymer 30 (40) | PAG-1 (5.0) | Q-1 (4.7) | — | PGMEA (1,080) | EL (1,080) | PGME (1,440) |
| | 3-64 | R-64 | Polymer 10 (40) Polymer 37 (40) | PAG-1 (5.0) | Q-1 (4.6) | — | PGMEA (1,080) | EL (1,080) | PGME (1,440) |

TABLE 10-continued

| | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|
| 3-65 | R-65 | Polymer 11 (40) Polymer 38 (40) | PAG-1 (5.0) | Q-1 (4.7) | — | PGMEA (1,080) | EL (1,080) | PGME (1,440) |
| 3-66 | R-66 | Polymer 12 (40) Polymer 39 (40) | PAG-1 (5.0) | Q-1 (4.9) | — | PGMEA (1,080) | EL (1,080) | PGME (1,440) |
| 3-67 | R-67 | Polymer 13 (40) Polymer 40 (40) | PAG-1 (5.0) | Q-1 (5.0) | — | PGMEA (1,080) | EL (1,080) | PGME (1,440) |
| 3-68 | R-68 | Polymer 14 (40) Polymer 41 (40) | PAG-1 (5.0) | Q-1 (5.2) | — | PGMEA (1,080) | EL (1,080) | PGME (1,440) |
| 3-69 | R-69 | Polymer 18 (40) Polymer 40 (40) | PAG-1 (5.0) | Q-1 (5.1) | — | PGMEA (1,080) | EL (1,080) | PGME (1,440) |
| 3-70 | R-70 | Polymer 19 (40) Polymer 41 (40) | PAG-1 (5.0) | Q-1 (4.9) | — | PGMEA (1,080) | EL (1,080) | PGME (1,440) |
| 3-71 | R-71 | Polymer 20 (40) Polymer 42 (40) | PAG-1 (5.0) | Q-1 (5.0) | — | PGMEA (1,080) | EL (1,080) | PGME (1,440) |
| 3-72 | R-72 | Polymer 21 (40) Polymer 43 (40) | PAG-1 (5.0) | Q-1 (5.0) | — | PGMEA (1,080) | EL (1,080) | PGME (1,440) |
| 3-73 | R-73 | Polymer 1 (80) | — | Q-1 (4.2) | FP-1 (3.0) | PGMEA (1,080) | EL (1,080) | PGME (1,440) |
| 3-74 | R-74 | Polymer 1 (40) Polymer 28 (40) | — | Q-1 (4.6) | FP-1 (3.0) | PGMEA (1,080) | EL (1,080) | PGME (1,440) |
| 3-75 | R-75 | Polymer 1 (40) Polymer 28 (40) | PAG-1 (5.0) | Q-1 (4.8) | FP-1 (3.0) | PGMEA (1,080) | EL (1,080) | PGME (1,440) |

TABLE 11

| | | Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|---|---|
| Comparative Example | 2-1 | CR-1 | Comparative Polymer 1 (80) | — | Q-1 (4.1) | — | PGMEA (1,080) | EL (1,080) | PGME (1,440) |
| | 2-2 | CR-2 | Comparative Polymer 2 (80) | — | Q-1 (4.1) | — | PGMEA (1,080) | EL (1,080) | PGME (1,440) |
| | 2-3 | CR-3 | Comparative Polymer 3 (80) | — | Q-1 (4.2) | — | PGMEA (1,080) | EL (1,080) | PGME (1,440) |
| | 2-4 | CR-4 | Comparative Polymer 4 (80) | — | Q-1 (4.4) | — | PGMEA (1,080) | EL (1,080) | PGME (1,440) |
| | 2-5 | CR-5 | Comparative Polymer 5 (80) | PAG-1 (5.0) | Q-1 (4.7) | — | PGMEA (1,080) | EL (1,080) | PGME (1,440) |
| | 2-6 | CR-6 | Comparative Polymer 6 (80) | PAG-1 (5.0) | Q-1 (4.5) | — | PGMEA (1,080) | EL (1,080) | PGME (1,440) |
| | 2-7 | CR-7 | Comparative Polymer 7 (80) | PAG-1 (5.0) | Q-1 (4.6) | — | PGMEA (1,080) | EL (1,080) | PGME (1,440) |

TABLE 11-continued

| Resist composition | Resin (pbw) | Acid generator (pbw) | Quencher (pbw) | Additive (pbw) | Solvent 1 (pbw) | Solvent 2 (pbw) | Solvent 3 (pbw) |
|---|---|---|---|---|---|---|---|
| 2-8 | CR-8 | Comparative Polymer 8 (80) | PAG-1 (5.0) | Q-1 (4.3) | — | PGMEA (1,080) | EL (1,080) | PGME (1,440) |
| 2-9 | CR-9 | Comparative Polymer 1 (40) Comparative Polymer 5 (40) | PAG-1 (5.0) | Q-1 (4.9) | — | PGMEA (1,080) | EL (1,080) | PGME (1,440) |
| 2-10 | CR-10 | Comparative Polymer 4 (40) Comparative Polymer 8 (40) | PAG-1 (5.0) | Q-1 (5.0) | — | PGMEA (1,080) | EL (1,080) | PGME (1,440) |

The acid generators (PAG-1 to PAG-4), quenchers (Q-1 to Q-4), and fluorinated polymer (FP-1) in Tables 8 to 11 are identified below.

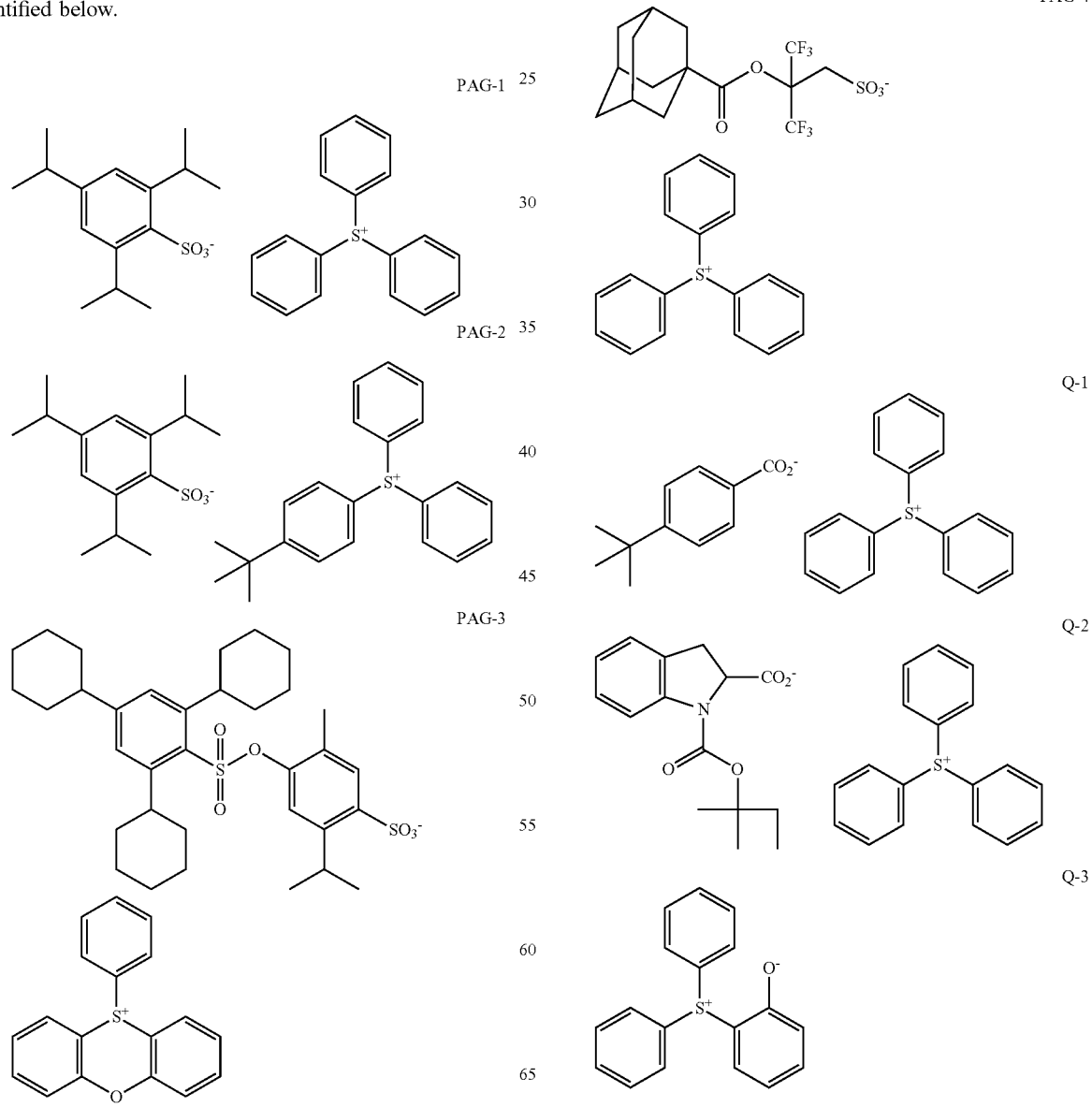

-continued

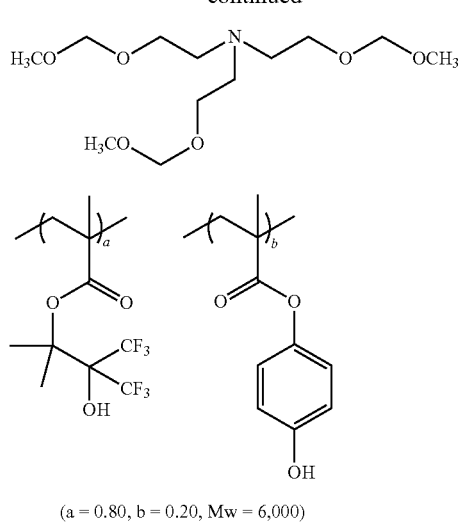

Q-4

FP-1

(a = 0.80, b = 0.20, Mw = 6,000)

[4] EB Writing Test

Examples 4-1 to 4-75 and Comparative Examples 3-1 to 3-10

(1) Evaluation of Resolution

Using a coater/developer system ACT-M (Tokyo Electron Ltd.), each of the negative resist compositions (R-1 to R-75 and CR-1 to CR-10) was spin coated onto a photomask blank of 152 mm squares having a chromium oxynitride film at the outermost surface and prebaked on a hot plate at 110° C. for 600 seconds to form a resist film of 75 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 kV), then baked (PEB) at 130° C. for 600 seconds, and developed in a 2.38 wt % TMAH aqueous solution, thereby yielding negative patterns.

The patterned mask blank was observed under a top-down scanning electron microscope (TD-SEM). The optimum exposure (Eop) was defined as the exposure dose ($\mu C/cm^2$) which provided a 1:1 resolution at the top and bottom of a 400-nm line-and-space (LS) pattern. The maximum resolution of the resist was defined as the minimum line width of a LS pattern that could be resolved at the optimum exposure. The LER of a 200-nm LS pattern was measured under SEM. Also, the resist film was exposed to an isolated line (IL) pattern and an isolated space (IS) pattern of EB in the dose (Eop) which provided a 1:1 resolution of a 400-nm LS pattern, and the minimum size is reported as resolution of IL and IS. The resolution of IL is that of an isolated single line, and the resolution of IS is that of an isolated single space. The results are shown in Tables 12 to 14. The optimum dose in Tables 12 to 14 is the value based on LS pattern.

TABLE 12

| | Resist composition | Optimum dose of LS ($\mu C/cm^2$) | Resolution of LS (nm) | Resolution of IL (nm) | Resolution of IS (nm) | LER (nm) |
|---|---|---|---|---|---|---|
| Example 4-1 | R-1 | 47 | 35 | 35 | 35 | 4.6 |
| 4-2 | R-2 | 49 | 35 | 35 | 35 | 4.7 |
| 4-3 | R-3 | 51 | 35 | 35 | 35 | 4.7 |
| 4-4 | R-4 | 46 | 35 | 35 | 35 | 4.6 |
| 4-5 | R-5 | 48 | 35 | 35 | 35 | 4.8 |
| 4-6 | R-6 | 46 | 35 | 35 | 35 | 4.7 |
| 4-7 | R-7 | 49 | 35 | 35 | 40 | 4.8 |
| 4-8 | R-8 | 48 | 35 | 40 | 40 | 4.9 |
| 4-9 | R-9 | 47 | 40 | 35 | 35 | 4.8 |
| 4-10 | R-10 | 51 | 40 | 35 | 35 | 4.7 |
| 4-11 | R-11 | 51 | 40 | 35 | 40 | 4.8 |
| 4-12 | R-12 | 51 | 35 | 40 | 35 | 4.7 |
| 4-13 | R-13 | 49 | 35 | 35 | 35 | 4.6 |
| 4-14 | R-14 | 48 | 35 | 40 | 35 | 4.9 |
| 4-15 | R-15 | 48 | 35 | 35 | 35 | 4.8 |
| 4-16 | R-16 | 49 | 40 | 40 | 35 | 4.7 |
| 4-17 | R-17 | 47 | 40 | 35 | 40 | 4.9 |
| 4-18 | R-18 | 47 | 35 | 40 | 35 | 4.8 |
| 4-19 | R-19 | 47 | 35 | 35 | 35 | 4.8 |
| 4-20 | R-20 | 47 | 40 | 35 | 40 | 4.9 |
| 4-21 | R-21 | 48 | 35 | 35 | 40 | 4.9 |
| 4-22 | R-22 | 46 | 35 | 40 | 35 | 4.9 |
| 4-23 | R-23 | 50 | 40 | 35 | 35 | 4.8 |
| 4-24 | R-24 | 49 | 40 | 35 | 35 | 4.7 |
| 4-25 | R-25 | 49 | 35 | 40 | 35 | 4.8 |
| 4-26 | R-26 | 48 | 35 | 40 | 40 | 4.8 |
| 4-27 | R-27 | 47 | 35 | 40 | 40 | 4.7 |
| 4-28 | R-28 | 49 | 35 | 40 | 35 | 4.7 |
| 4-29 | R-29 | 48 | 40 | 35 | 35 | 4.8 |
| 4-30 | R-30 | 49 | 35 | 35 | 40 | 4.8 |
| 4-31 | R-31 | 49 | 35 | 40 | 35 | 4.7 |
| 4-32 | R-32 | 48 | 35 | 40 | 40 | 4.7 |
| 4-33 | R-33 | 47 | 40 | 35 | 35 | 4.9 |
| 4-34 | R-34 | 46 | 40 | 35 | 35 | 4.8 |
| 4-35 | R-35 | 52 | 40 | 40 | 35 | 4.8 |
| 4-36 | R-36 | 48 | 35 | 40 | 35 | 4.9 |

TABLE 12-continued

|  | Resist composition | Optimum dose of LS (μC/cm$^2$) | Resolution of LS (nm) | Resolution of IL (nm) | Resolution of IS (nm) | LER (nm) |
|---|---|---|---|---|---|---|
| 4-37 | R-37 | 48 | 35 | 40 | 35 | 4.7 |
| 4-38 | R-38 | 49 | 35 | 35 | 40 | 4.8 |

TABLE 13

|  |  | Resist composition | Optimum dose of LS (μC/cm$^2$) | Resolution of LS (nm) | Resolution of IL (nm) | Resolution of IS (nm) | LER (nm) |
|---|---|---|---|---|---|---|---|
| Example | 4-39 | R-39 | 47 | 35 | 40 | 35 | 4.9 |
|  | 4-40 | R-40 | 48 | 40 | 35 | 35 | 4.7 |
|  | 4-41 | R-41 | 46 | 40 | 40 | 35 | 4.8 |
|  | 4-42 | R-42 | 49 | 35 | 40 | 35 | 4.9 |
|  | 4-43 | R-43 | 49 | 35 | 40 | 35 | 4.8 |
|  | 4-44 | R-44 | 48 | 35 | 35 | 40 | 4.7 |
|  | 4-45 | R-45 | 47 | 40 | 40 | 35 | 4.7 |
|  | 4-46 | R-46 | 46 | 40 | 35 | 35 | 4.7 |
|  | 4-47 | R-47 | 48 | 40 | 40 | 35 | 4.8 |
|  | 4-48 | R-48 | 48 | 35 | 40 | 35 | 4.9 |
|  | 4-49 | R-49 | 49 | 40 | 35 | 35 | 4.7 |
|  | 4-50 | R-50 | 50 | 40 | 40 | 35 | 4.8 |
|  | 4-51 | R-51 | 48 | 35 | 40 | 40 | 4.9 |
|  | 4-52 | R-52 | 49 | 35 | 35 | 35 | 4.7 |
|  | 4-53 | R-53 | 50 | 40 | 35 | 35 | 4.9 |
|  | 4-54 | R-54 | 48 | 35 | 35 | 35 | 4.8 |
|  | 4-55 | R-55 | 49 | 35 | 35 | 35 | 4.9 |
|  | 4-56 | R-56 | 48 | 35 | 35 | 35 | 4.8 |
|  | 4-57 | R-57 | 51 | 35 | 35 | 35 | 4.7 |
|  | 4-58 | R-58 | 50 | 40 | 35 | 35 | 4.7 |
|  | 4-59 | R-59 | 51 | 35 | 40 | 35 | 4.8 |
|  | 4-60 | R-60 | 49 | 40 | 40 | 35 | 4.8 |
|  | 4-61 | R-61 | 48 | 40 | 35 | 35 | 4.9 |
|  | 4-62 | R-62 | 47 | 35 | 40 | 35 | 4.9 |
|  | 4-63 | R-63 | 49 | 35 | 40 | 40 | 4.8 |
|  | 4-64 | R-64 | 46 | 35 | 35 | 35 | 4.8 |
|  | 4-65 | R-65 | 51 | 40 | 35 | 35 | 4.9 |
|  | 4-66 | R-66 | 49 | 40 | 35 | 40 | 4.9 |
|  | 4-67 | R-67 | 50 | 40 | 35 | 40 | 4.8 |
|  | 4-68 | R-68 | 49 | 35 | 40 | 35 | 4.9 |
|  | 4-69 | R-69 | 48 | 35 | 40 | 35 | 4.7 |
|  | 4-70 | R-70 | 50 | 40 | 35 | 35 | 4.8 |
|  | 4-71 | R-71 | 51 | 40 | 35 | 35 | 4.9 |
|  | 4-72 | R-72 | 47 | 40 | 35 | 35 | 4.7 |
|  | 4-73 | R-73 | 48 | 35 | 40 | 40 | 4.8 |
|  | 4-74 | R-74 | 49 | 40 | 40 | 35 | 4.9 |
|  | 4-75 | R-75 | 50 | 40 | 40 | 35 | 4.7 |

TABLE 14

|  |  | Resist composition | Optimum dose of LS (μC/cm$^2$) | Resolution of LS (nm) | Resolution of IL (nm) | Resolution of IS (nm) | LER (nm) |
|---|---|---|---|---|---|---|---|
| Comparative Example | 3-1 | CR-1 | 49 | 40 | 40 | 45 | 4.8 |
|  | 3-2 | CR-2 | 49 | 45 | 40 | 40 | 4.8 |
|  | 3-3 | CR-3 | 48 | 45 | 40 | 40 | 4.7 |
|  | 3-4 | CR-4 | 50 | 45 | 40 | 40 | 4.7 |
|  | 3-5 | CR-5 | 50 | 50 | 50 | 50 | 4.9 |
|  | 3-6 | CR-6 | Si | 50 | 50 | 50 | 4.9 |
|  | 3-7 | CR-7 | 48 | 40 | 40 | 45 | 4.8 |
|  | 3-8 | CR-8 | 48 | 45 | 40 | 45 | 4.7 |
|  | 3-9 | CR-9 | 49 | 45 | 40 | 40 | 4.8 |
|  | 3-10 | CR-10 | 50 | 40 | 45 | 40 | 4.8 |

Examples 5-1 to 5-7 and Comparative Examples 4-1 to 4-5

(2) Evaluation of Defects

Using the negative resist composition (R-1, R-3, R-15, R-17, R-54, R-55, R-58, CR-1, CR-2, CR-5, CR-6 and CR-9), a resist pattern was formed at a center area of the substrate through exposure and development under the same conditions as in (1) Evaluation of resolution. The unexposed area was inspected by a mask process monitoring system (M2351 by Lasertec Corp.) to see whether or not radial development residues were present on the chromium film. The results are shown in Table 15.

TABLE 15

| | | Resist composition | Radial defects |
|---|---|---|---|
| Example | 5-1 | R-1 | nil |
| | 5-2 | R-3 | nil |
| | 5-3 | R-15 | nil |
| | 5-4 | R-17 | nil |
| | 5-5 | R-54 | nil |
| | 5-6 | R-55 | nil |
| | 5-7 | R-58 | nil |
| Comparative Example | 4-1 | CR-1 | found |
| | 4-2 | CR-2 | found |
| | 4-3 | CR-5 | found |
| | 4-4 | CR-6 | found |
| | 4-5 | CR-9 | found |

As seen from Tables 12 to 14, the negative resist compositions of Examples mark better values of resolution and LER than the negative resist compositions of Comparative Examples.

As seen from Table 15, the negative resist compositions of Examples are improved in defect performance because no radial defects are found. The negative resist compositions of Comparative Examples are not so low in resolution, but reveal radial residues on defect inspection. The polymer used in Comparative Examples induces crosslinking under the action of acid in the exposed region and forms a dehydrated polymer. Since the dehydrated polymer has a low solubility in developer, the dehydrated polymer dissolving out of the exposed region is not completely removed during development and left on the substrate at the end of development. As a result, radial residues are formed.

It has been demonstrated that using the negative resist composition of the invention, a resist pattern with a high resolution and minimal LER is formed. These improvements combined with the advantage of elimination of development defects ensure that the pattern forming process using the negative resist composition is useful in photolithography in the manufacture of semiconductor devices, especially in the processing of photomask blanks where a reduced number of defects is desirable.

Japanese Patent Application No. 2018-100615 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. A polymer consisting of
recurring units having the formula (a),
recurring units having the formula (b1'),
recurring units of at least one type selected from recurring units having the formula (c), recurring units having the formula (d), and recurring units having the formula (e), and
optionally recurring units of at least one type selected from recurring units having the formula (f1), recurring units having the formula (f2), and recurring units having the formula (f3):

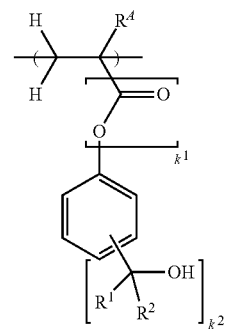

(a)

wherein $R^A$ is hydrogen or methyl, $R^1$ and $R^2$ are each independently a $C_1$-$C_{15}$ primary or secondary alkyl group in which some hydrogen may be substituted by a hydroxyl or $C_1$-$C_6$ alkoxy moiety, or $R^1$ and $R^2$ may bond together to form a ring with the carbon atom to which they are attached, $k^1$ is 0 or 1, and $k^2$ is an integer of 2 to 4,

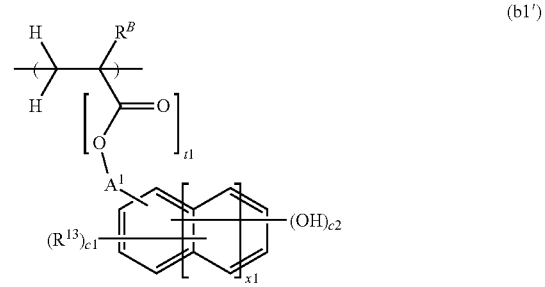

(b1')

wherein $R^B$ is hydrogen, fluorine, methyl or trifluoromethyl,
$A^1$ is a single bond or a $C_1$-$C_{10}$ alkanediyl group which may contain an ether bond,
$R^{13}$ is a halogen atom, optionally halogenated $C_2$-$C_8$ acyloxy group, optionally halogenated $C_1$-$C_6$ alkyl group, or optionally halogenated $C_1$-$C_6$ alkoxy group,
t1 is 0 or 1, x1 is an integer of 0 to 2, c1 is an integer satisfying 0≤c1≤5+2(x1)−c2, c2 is an integer of 1 to 3,

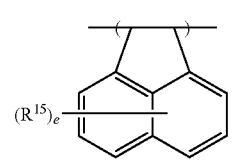

(c)

-continued (d)

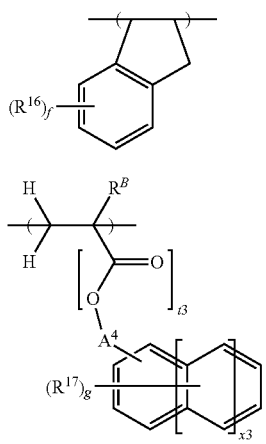

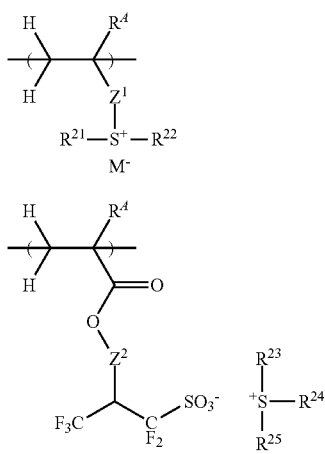

wherein $R^B$ is hydrogen, fluorine, methyl or trifluoromethyl, $R^{15}$ and $R^{16}$ are each independently a halogen atom, optionally halogenated $C_2$-$C_8$ acyloxy group, optionally halogenated $C_1$-$C_6$ alkyl group, or optionally halogenated $C_1$-$C_6$ alkoxy group, $R^{17}$ is an acetyl, acetoxy, $C_1$-$C_{20}$ alkyl, $C_1$-$C_{20}$ primary alkoxy, $C_2$-$C_{20}$ secondary alkoxy, $C_2$-$C_{20}$ acyloxy, $C_2$-$C_{20}$ alkoxyalkyl, $C_2$-$C_{20}$ alkylthioalkyl, halogen, nitro or cyano group, $A^4$ is a single bond or a $C_1$-$C_{10}$ alkanediyl group which may contain an ether bond, e is an integer of 0 to 5, f is an integer of 0 to 3, g is an integer of 0 to 5, t3 is 0 or 1, and x3 is an integer of 0 to 2,

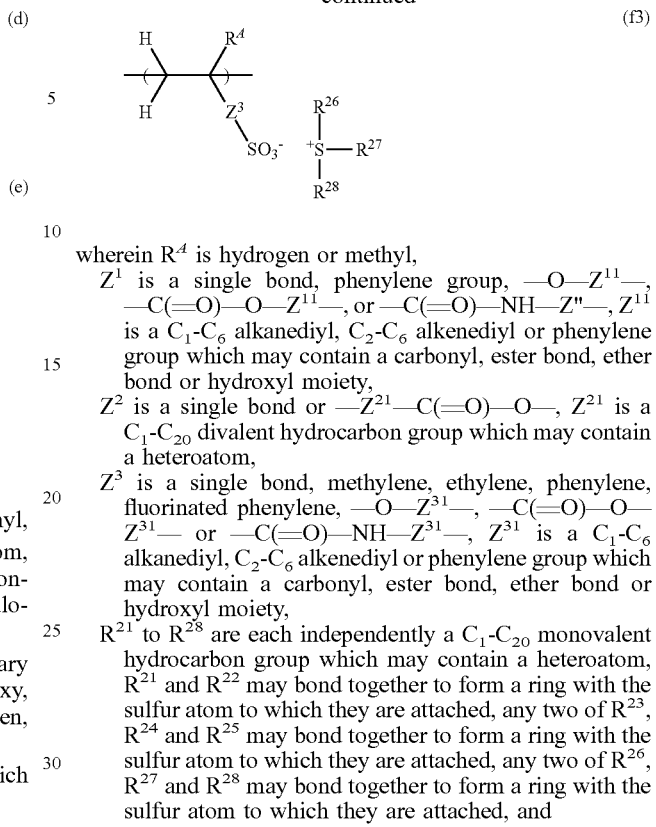

-continued wherein $R^A$ is hydrogen or methyl, $Z^1$ is a single bond, phenylene group, —O—$Z^{11}$—, —C(=O)—O—$Z^{11}$—, or —C(=O)—NH—$Z''$—, $Z^{11}$ is a $C_1$-$C_6$ alkanediyl, $C_2$-$C_6$ alkenediyl or phenylene group which may contain a carbonyl, ester bond, ether bond or hydroxyl moiety, $Z^2$ is a single bond or —$Z^{21}$—C(=O)—O—, $Z^{21}$ is a $C_1$-$C_{20}$ divalent hydrocarbon group which may contain a heteroatom, $Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl, $C_2$-$C_6$ alkenediyl or phenylene group which may contain a carbonyl, ester bond, ether bond or hydroxyl moiety, $R^{21}$ to $R^{28}$ are each independently a $C_1$-$C_{20}$ monovalent hydrocarbon group which may contain a heteroatom, $R^{21}$ and $R^{22}$ may bond together to form a ring with the sulfur atom to which they are attached, any two of $R^{23}$, $R^{24}$ and $R^{25}$ may bond together to form a ring with the sulfur atom to which they are attached, any two of $R^{26}$, $R^{27}$ and $R^{28}$ may bond together to form a ring with the sulfur atom to which they are attached, and $M^-$ is a non-nucleophilic counter ion.

2. A negative resist composition comprising a base polymer containing the polymer of claim 1.

3. The negative resist composition of claim 2, further comprising an acid generator.

4. The negative resist composition of claim 2, further comprising a quencher.

5. A photomask blank comprising a resist film formed of the negative resist composition of claim 2.

6. A resist pattern forming process comprising the steps of applying the negative resist composition of claim 2 onto a substrate to form a resist film thereon, exposing patternwise the resist film to high-energy radiation, and developing the resist film in an alkaline developer to form a resist pattern.

7. The pattern forming process of claim 6 wherein the high-energy radiation is EUV or EB.

8. The pattern forming process of claim 6 wherein the substrate has an outermost surface formed of a chromium-containing material.

9. The pattern forming process of claim 6 wherein the substrate is a photomask blank.

10. The polymer of claim 1 wherein both $R^1$ and $R^2$ are $C_1$-$C_{15}$ primary or secondary alkyl groups.

* * * * *